(12) United States Patent
Dominguez-Bello

(10) Patent No.: US 11,564,667 B2
(45) Date of Patent: Jan. 31, 2023

(54) DEVICE AND METHOD OF RESTORING MICROBIOTA OF NEWBORNS

(71) Applicant: New York University, New York, NY (US)

(72) Inventor: Maria Gloria Dominguez-Bello, New York, NY (US)

(73) Assignee: New York University, New York, NY (US)

( * ) Notice: Subject to any disclaimer, the term of this patent is extended or adjusted under 35 U.S.C. 154(b) by 754 days.

(21) Appl. No.: 16/064,110

(22) PCT Filed: Dec. 27, 2016

(86) PCT No.: PCT/US2016/068735
§ 371 (c)(1),
(2) Date: Jun. 20, 2018

(87) PCT Pub. No.: WO2017/117142
PCT Pub. Date: Jul. 6, 2017

(65) Prior Publication Data
US 2019/0021703 A1 Jan. 24, 2019

Related U.S. Application Data

(60) Provisional application No. 62/271,692, filed on Dec. 28, 2015.

(51) Int. Cl.
*A61B 10/00* (2006.01)
*C12Q 1/24* (2006.01)
(Continued)

(52) U.S. Cl.
CPC ........ *A61B 10/0045* (2013.01); *A61K 35/742* (2013.01); *C12Q 1/24* (2013.01);
(Continued)

(58) Field of Classification Search
CPC ........ A61B 10/0045; A61B 2010/0074; C12Q 1/24
(Continued)

(56) References Cited

U.S. PATENT DOCUMENTS 3,640,268 A * 2/1972 Davis ............... B01L 3/5029
600/572
3,877,464 A * 4/1975 Vermes ............ A61B 10/0291
600/572
(Continued)

FOREIGN PATENT DOCUMENTS

EP 433299 B1 6/1991
EP 888118 B1 1/1999
(Continued)

OTHER PUBLICATIONS

International Preliminary Report on Patentability issued in International Application No. PCT/US2016/068735 dated Jul. 3, 2018, 7 pages.
(Continued)

*Primary Examiner* — Daniel L Cerioni
*Assistant Examiner* — Raymond P Dulman
(74) *Attorney, Agent, or Firm* — Troutman Pepper Hamilton Sanders LLP

(57) ABSTRACT

The invention relates to methods and compositions for restoring normal microbiota in pre-term newborns or newborns delivered by Cesarean section and methods for preventing or ameliorating diseases associated with delivery by Cesarean section or pre-term birth comprising administering to said newborns at the time of birth or shortly thereafter an effective amount of a vaginal microbiota inoculum obtained from the newborn's mother or a donor or an effective amount of a probiotic composition. The invention also relates to a device for collecting maternal vaginal microbiota
(Continued)

from the vaginal canal of a patient. The device can have a housing forming a cavity, an absorbent material removable disposed within the cavity, and a deployment element disposed in the housing and movable along a length of the housing. The movement of the deployment element can displace the absorbent material out of the cavity and in to the vaginal canal.

15 Claims, 21 Drawing Sheets

Specification includes a Sequence Listing.

(51) Int. Cl.
    *A61K 35/742* (2015.01)
    *A61K 35/745* (2015.01)
    *A61K 35/747* (2015.01)
(52) U.S. Cl.
    CPC ..... *A61B 2010/0074* (2013.01); *A61K 35/745* (2013.01); *A61K 35/747* (2013.01)
(58) Field of Classification Search
    USPC .................................. 600/572–574, 582
    See application file for complete search history.

(56) References Cited

U.S. PATENT DOCUMENTS

| | | | | |
|---|---|---|---|---|
| 4,157,709 | A * | 6/1979 | Schuster | A61B 10/0291 600/572 |
| 4,257,427 | A * | 3/1981 | Bucalo | A61B 10/0045 435/309.1 |
| 4,312,950 | A | 1/1982 | Snyder et al. | |
| 4,485,824 | A * | 12/1984 | Koll | A61B 10/0291 600/569 |
| 5,445,164 | A * | 8/1995 | Worthen | A61B 10/0045 600/572 |
| 5,599,795 | A | 2/1997 | McCann et al. | |
| 6,080,401 | A | 6/2000 | Reddy et al. | |
| 6,262,019 | B1 | 7/2001 | Keller et al. | |
| 6,540,728 | B2 * | 4/2003 | Zadini | A61B 17/12099 600/573 |
| 6,589,216 | B1 | 7/2003 | Abbott et al. | |
| 6,645,530 | B1 | 11/2003 | Borody | |
| 6,723,326 | B1 | 4/2004 | Farmer | |
| 7,037,275 | B1 * | 5/2006 | Marshall | A61B 10/02 600/562 |
| 7,374,924 | B2 | 5/2008 | Connolly et al. | |
| 7,507,402 | B1 | 3/2009 | Farmer et al. | |
| 7,629,155 | B2 | 12/2009 | Sato et al. | |
| 7,834,061 | B2 | 11/2010 | Sato et al. | |
| 8,025,911 | B2 | 9/2011 | Uchida et al. | |
| 8,110,607 | B2 | 2/2012 | Sato et al. | |
| 8,241,684 | B2 | 8/2012 | Uchida et al. | |
| 8,309,073 | B2 | 11/2012 | Mäyrä-Mäkinen et al. | |
| 8,398,606 | B2 | 3/2013 | Fleming | |
| 8,460,648 | B2 | 6/2013 | Borody | |
| 8,604,005 | B2 | 12/2013 | Kajander et al. | |
| 8,691,213 | B2 | 4/2014 | Langford et al. | |
| 8,691,235 | B2 | 4/2014 | Shalaby et al. | |
| 8,734,364 | B1 | 5/2014 | Mantzaris et al. | |
| 8,734,823 | B2 | 5/2014 | Amodei et al. | |
| 8,758,842 | B2 | 6/2014 | Furuichi et al. | |
| 9,040,036 | B2 | 5/2015 | Borody | |
| 9,050,358 | B2 | 6/2015 | Borody | |
| 2002/0032389 | A1 * | 3/2002 | Fournier | A61B 10/0291 600/572 |
| 2002/0087096 | A1 * | 7/2002 | Anderson | A61B 10/0291 600/572 |
| 2002/0123697 | A1 * | 9/2002 | Ishizaka | A61B 10/0045 600/572 |
| 2003/0028123 | A1 * | 2/2003 | Pevoto | A61B 10/0045 600/562 |
| 2003/0138476 | A1 | 7/2003 | Van Leeuwen et al. | |
| 2004/0005304 | A1 | 1/2004 | Brudnak | |
| 2004/0062757 | A1 | 4/2004 | Finegold | |
| 2004/0076614 | A1 | 4/2004 | Schur | |
| 2004/0170617 | A1 | 9/2004 | Finegold | |
| 2004/0185032 | A1 | 9/2004 | Burrell | |
| 2005/0288606 | A1 * | 12/2005 | Alter | A61D 1/00 600/572 |
| 2006/0062773 | A1 | 3/2006 | Davis et al. | |
| 2006/0062774 | A1 | 3/2006 | Davis et al. | |
| 2007/0298013 | A1 | 12/2007 | Altman | |
| 2008/0069861 | A1 | 3/2008 | Brown et al. | |
| 2008/0311097 | A1 | 12/2008 | Israelsen | |
| 2009/0053756 | A1 | 2/2009 | Virkki et al. | |
| 2009/0324547 | A1 | 12/2009 | Wikström et al. | |
| 2010/0028449 | A1 | 2/2010 | Prakash et al. | |
| 2010/0086527 | A1 | 4/2010 | Huber-Haag et al. | |
| 2010/0111915 | A1 | 5/2010 | Isolauri et al. | |
| 2010/0119488 | A1 | 5/2010 | Huber-Haag et al. | |
| 2010/0166721 | A1 | 7/2010 | Masri | |
| 2010/0226899 | A1 | 9/2010 | Osborn et al. | |
| 2010/0247489 | A1 | 9/2010 | Saur-Brosch | |
| 2010/0284979 | A1 | 11/2010 | O'Mahony et al. | |
| 2011/0052538 | A1 | 3/2011 | Brown et al. | |
| 2011/0064707 | A1 | 3/2011 | Rochat et al. | |
| 2011/0087133 | A1 | 4/2011 | Ching et al. | |
| 2011/0110905 | A1 | 5/2011 | Ritchie | |
| 2011/0117077 | A1 | 5/2011 | Schmitt et al. | |
| 2011/0150851 | A1 | 6/2011 | Schmitt et al. | |
| 2011/0165127 | A1 | 7/2011 | Masri | |
| 2011/0189132 | A1 | 8/2011 | Garner et al. | |
| 2011/0223137 | A1 | 9/2011 | Darmaun et al. | |
| 2012/0034198 | A1 | 2/2012 | Garner et al. | |
| 2012/0121562 | A1 | 5/2012 | Bergonzelli Degonda et al. | |
| 2012/0121564 | A1 | 5/2012 | Connolly et al. | |
| 2012/0128726 | A1 | 5/2012 | Marcenier et al. | |
| 2012/0134973 | A1 | 5/2012 | Kekkonen | |
| 2012/0230956 | A1 | 9/2012 | McLean et al. | |
| 2012/0269789 | A1 | 10/2012 | Mercenier et al. | |
| 2013/0189236 | A1 | 7/2013 | Ware | |
| 2013/0273015 | A1 | 10/2013 | Klassen et al. | |
| 2013/0280239 | A1 | 10/2013 | Klassen et al. | |
| 2013/0316922 | A1 | 11/2013 | Balashov et al. | |
| 2013/0330307 | A1 | 12/2013 | Millan | |
| 2013/0330308 | A1 | 12/2013 | Millan et al. | |
| 2014/0037603 | A1 | 2/2014 | Bolster et al. | |
| 2014/0093479 | A1 | 4/2014 | Mogna et al. | |
| 2014/0112985 | A1 | 4/2014 | Bochenek et al. | |
| 2014/0193542 | A1 | 7/2014 | Langford et al. | |
| 2014/0234279 | A1 | 8/2014 | Millan | |
| 2014/0255351 | A1 | 9/2014 | Brestad et al. | |
| 2014/0286920 | A1 | 9/2014 | Mayra-Makinen et al. | |
| 2014/0363397 | A1 | 12/2014 | Allen-Vercoe et al. | |
| 2015/0174080 | A1 | 6/2015 | Schiffrin et al. | |
| 2015/0181916 | A1 | 7/2015 | Klassen et al. | |
| 2015/0209383 | A1 | 7/2015 | Boileau et al. | |
| 2015/0246081 | A1 | 9/2015 | Morris | |
| 2015/0283144 | A1 | 10/2015 | Harmsen et al. | |
| 2015/0284781 | A1 | 10/2015 | Klumpp et al. | |
| 2015/0290261 | A1 | 10/2015 | Chichlowski et al. | |
| 2015/0344940 | A1 | 12/2015 | Savidge et al. | |
| 2015/0352162 | A1 | 12/2015 | Chassard et al. | |
| 2016/0000838 | A1 | 1/2016 | Harmsen et al. | |
| 2016/0017409 | A1 | 1/2016 | Flavell et al. | |
| 2016/0022592 | A1 | 1/2016 | Kabadi et al. | |
| 2016/0030494 | A1 | 2/2016 | Henn et al. | |
| 2016/0074505 | A1 | 3/2016 | Kovarik et al. | |
| 2016/0110515 | A1 | 4/2016 | Apte et al. | |

FOREIGN PATENT DOCUMENTS

| | | | |
|---|---|---|---|
| EP | 1374878 | A1 | 1/2004 |
| EP | 1513541 | B1 | 3/2005 |
| EP | 1531841 | B1 | 5/2005 |
| EP | 1776877 | A1 | 4/2007 |
| EP | 1782818 | B1 | 5/2007 |
| EP | 1869161 | B1 | 12/2007 |
| EP | 1974743 | A1 | 10/2008 |
| EP | 1978979 | B1 | 10/2008 |

(56) References Cited

FOREIGN PATENT DOCUMENTS

| | | |
|---|---|---|
| EP | 1987835 A2 | 11/2008 |
| EP | 2040722 B1 | 4/2009 |
| EP | 2110133 B1 | 10/2009 |
| EP | 2124972 B1 | 12/2009 |
| EP | 2129386 B1 | 12/2009 |
| EP | 2131680 B1 | 12/2009 |
| EP | 2147678 A1 | 1/2010 |
| EP | 2164349 B1 | 3/2010 |
| EP | 2169050 B1 | 3/2010 |
| EP | 2585085 B1 | 5/2013 |
| EP | 2609814 A1 | 7/2013 |
| WO | 2009144137 A1 | 12/2009 |
| WO | 2010002241 A1 | 1/2010 |
| WO | 2011005756 A1 | 1/2011 |
| WO | 2011022542 A2 | 2/2011 |
| WO | 2013122931 A2 | 8/2013 |
| WO | 2013166031 A1 | 11/2013 |
| WO | 2014165810 A2 | 10/2014 |
| WO | 2014182632 A1 | 11/2014 |
| WO | 2015004270 A1 | 1/2015 |
| WO | 2015026235 A2 | 2/2015 |
| WO | 2015099753 A1 | 7/2015 |
| WO | 2015099754 A1 | 7/2015 |
| WO | 2015153841 A1 | 10/2015 |
| WO | 2015168534 A1 | 11/2015 |
| WO | 2015189472 A1 | 12/2015 |
| WO | 2016011335 A1 | 1/2016 |
| WO | 2016033439 A2 | 3/2016 |
| WO | 2016049920 A1 | 4/2016 |
| WO | 2016049932 A1 | 4/2016 |

OTHER PUBLICATIONS

Aagaard, K. et al., "A Metagenomic Approach to Characterization of the Vaginal Microbiome Signature in Pregnancy" PLOS One (2012) vol. 7, Issue 6, 15 pages total.

Aagaard, K. et al., "The Placenta Harbors a Unique Microbiome" Sci. Transl. Med. (2014) vol. 6, No. 237, pp. 1-22.

Abele-Horn M. et al. "Ureaplasma urealyticum in newborn and premature infants. Its association with bronchopulmonary dysplasia" Deutsche Medizinische Wochenschrift (1946) [1992, 117(11):408-414], Abstract—Europe PubMed Central, p. 1-3, http://europepmc.org/abstractfmed/1544343.

Ajslev, Ta et al., "Childhood Overweight After Establishment of the Gut Microbiota: The Role of Delivery Mode, Pre-Pregnancy Weight and Early Administration of Antibiotics" International Journal of Obesity (2011) vol. 35, pp. 522-529.

Algert, C.S. et al., "Perinatal Risk Factors for Early Onset of Type 1 Diabetes in a 2000-2005 Birth Cohort" Diabetic Medicine (2009) vol. 26, pp. 1193-1197.

Alicea-Serrano, A. M. et al., "Tetracycline resistance genes acquired at birth" Arch. Microbial. (2013) vol. 195, pp. 447-451.

Ankirskaia, As, et al., "Specific features of normal vaginal microflora in girls of preschool age", Zhurnal Mikrobiologii, Epidemiologii, i Immunobiologii [2004(4):54-58], Abstract—Europe PubMed Central., http://europepmc.org/abstract/med/15481922.

Aumeunier, A. et al., "Systemic Toll-Like Receptor Stimulation Suppresses Experimental Allergic Asthma and Autoimmune Diabetes in NOD Mice" PLoS ONE (2010) vol. 5, Issue 7, 14 pages total.

Avershina, E., et al., "Bifidobacterial Succession and Correlation Networks in a Large Unselected Cohort of Mothers and Their Children" Applied and Environmental Microbiology (2013) vol. 79, No. 2, pp. 497-507, doi:10.1128/AEM.02359-12.

Azad, M. B. et al., "Gut microbiota of healthy Canadian infants: profiles by mode of delivery and infant diet at 4 months" Canadian Medical Association Journal (2013) vol. 185, No. 5, pp. 385-394.

Bach, J-F. et al., "The Effect of Infections on Susceptibility to Autoimmune and Allergic Diseases" The New England Journal of Medicine: Mechanisms of Disease (2002) vol. 347, No. 12, pp. 911-920.

Bager, P. et al., "Cesarean Section and Offspring's Risk of Inflammatory Bowel Disease: A National Cohort Study" Inflamm Bowel Dis (2012) vol. 18, pp. 857-862.

Bakken, J.S. et al., "Treating Clostridium difficile Infection With Fecal Microbiota Transplantation," Clinical Gastroenterology and Hepatology (2011) vol. 9, pp. 1044-1049.

Balassanian, N. et al., "Epidemiologic and Serologic Studies of E. Coli 04:H5 in a Premature Nursery" (1968) vol. 41, No. 2., p. 463-472.

Barker, D.J.P., "Human Growth and Chronic Disease: A Memorial to Kim Tanner" Annals of Human Biology (2012) vol. 39, No. 5, pp. 335-341.

Biasucci, G. et al., "Cesarean Delivery May Affect the Early Biodiversity of Intestinal Bacterial ,2" The Journal of Nutrition (2008) pp. 1796S-1800S.

Biasucci, G. et al., "Mode of delivery affects the bacterial community in the newborn gut" Science Direct Early Human Development (2010) pp. 513-515.

Bird, J. A. et al., "Endocrine and metabolic adaptation following caesarean section or vaginal delivery" Archives of Disease in Childhood (1996) vol. 74, pp. F132-F134.

Bisanz, J. E. et al.,"The microbiota at multiple body sites during pregnancy in a rural Tanzanian population and the effects of Moringa supplemented probiotic yogurt", AEM Accepted Manuscript Posted Online May 15, 2015, Appl. Enviorn. Microbiol. (2015) doi:10.1128/AEM.00780-15, pp. 1-39.

Blustein, J. et al., "Association of Caesarean Delivery with Child Adiposity from Age 6 Weeks to 15 Years" Int J Obes (Lond) (2013) vol. 37, No. 7, pp. 900-906.

Buddington, R. K. et al., "Maternal-to-Infant Transmission of Probiotics: Concept Validation in Mice, Rats, and Pigs" Neonatology (2010) vol. 97, pp. 250-256, DOI: 10.1159/000253756—Abstract.

Cabrera-Rubio, R. et al., "The human milk microbiome changes over lactation and is shaped by maternal weight and mode of delivery" The American Journal of Clinical Nutrition (2012) vol. 96, pp. 544-551.

Caporaso, J. G. et al., "QIIME Allows Analysis of High-Throughput Community Sequencing Data" Nat Methods (2010) vol. 7, No. 5, pp. 335-336.

Caporaso, J.G. et al., "Ultra-High Throughput Microbial Community Analysis on the Illumina HiSeq and MiSeq Platforms" The ISME Journal (2012) vol. 6, pp. 1621-1624.

Chen, G. et al., "Nonfermentative Gram-negative bacilli encountered in specimens of obstetric patients: characterization, antibiotic sensitivity and clinical Significance" Chinese Journal of Microbiology and Immunology (1981) vol. 14 No. 2, pp. 14-27.

Cho, I. et al., "Antibiotics in Early Life Alter the Murine Colonic Microbiome and Adiposity" Nature (2012) vol. 488, No. 7413, pp. 621-626.

Costello, E. K. et al., "Bacterial Community Variation in Human Body Habitats Across Space and Time" National Institutes of Health (2009) vol. 326(5960): doi: 10.1126/science.1177486, pp. 1-8.

Couzin-Frankel, J., "Bacteria and Asthma: Untangling the Links" Science: NewsFocus (2010) vol. 330, pp. 1168-1169.

Cox, L.M. et al., "Altering the Intestinal Microbiota During a Critical Developmental Window has Lasting Metabolic Consequences" Cell (2014) vol. 158, No. 4, pp. 705-721.

Cox, L.M. et al., "Antibiotics in Early Life and Obesity" Nat Rev Endocrinol. (2015) vol. 11, No. 3, pp. 182-190.

Cox, L.M. et al., "Pathways in Microbe-Induced Obesity" Cell Metab. (2013) vol. 17, No. 6, pp. 883-894.

De Jesus-Laboy, K. M. et al.,"Restoring the Normal Microbiota of Cesarean-section Born Infants", American Society for Microbiology, ASM2014 Abstracts (2014) Abstract No. 1-741, 114th General Meeting—American Society for Microbiology, http://www.asmonlineeducation.com/php/asm2014abstractsidata/index/htm, 1 page total.

De Jesus-Laboy, K. M. et al.,"Restoring The Normal Microbiota of Cesarean-Section Born Infants", ASM Poster Board No. 741, 114th General Meeting-American Society for Microbiology (2014), 2 pages total.

(56) References Cited

OTHER PUBLICATIONS

Decker, E. et al., "Cesarean Delivery is Associated with Celiac Disease but Not Inflammatory Bowel Disease in Children" Pediatrics (2010) vol. 125, Issue 6, pp. e1433-1440, published online EpubJun (10.1542/peds.2009-2260).

Dimmitt, R.A. et al., "The Role of Postnatal Acquisition of the Intestinal Microbiome in the Early Development of Immune Function" J. Periatr Gastroenterol Nutr. (2010) vol. 51, No. 3, pp. 262-273.

Ding, T. et al., "Dynamics and associations of microbial community types across the human body", Nature (2014), vol. 509, doi:10.1038/nature13178, p. 357-367.

Dominguez-Bello M.G. et al., "Reply to Putignani et al.: Vagina as a major source of natural inoculum for the newborn" PNAS (2010) vol. 107:42, p. E160.

Dominguez-Bello M.G. et al.,"Delivery mode shapes the acquisition and structure of the initial microbiota across multiple body habitats in newborns" PNAS (2010) vol. 107, No. 26, pp. 11971-11975S.

Dominguez-Bello M.G. et al.,"Partial restoration of the microbiota of cesarean-born infants via vaginal microbial transfer" Nature Medicine—Brief Communications (2016) doi:10.1038/nm.4039, pp. 1-5.

Dominguez-Bello M.G. et al.,"Partial restoration of the microbiota of cesarean-born infants via vaginal microbial transfer" Nature Medicine: doi:10.1038/nm.4039 (2016) Supplemental Material, pp. 1-15.

Dong, X-D. et al. "Bacterial communities in neonatal feces are similar to mothers' placentae" Can. J. Infect Dis. Med. Microbiol. (2015) vol. 26, No. 2, pp. 90-94.

Ducluzeau, R., "Implantation and Development of the Gut Flora in the Newborn Animal" Annales de Recherches Veterinaires (1983) vol. 14:04, pp. 354-359, HAL Id: hal-00901435, https://hal.archives-ouvertes.fr/hal-00901435.

Eder, M. et al., "Normal ocular flora in newborns delivered in two hospital centers in Argentina and Paraguay" Graefe's Arch Clin Exp Ophthalmol (2005) vol. 243, pp. 1098-1107.

Ege, M.J. et al., "Exposure to Environmental Microorganisms and Childhood Asthma" (2011) vol. 364, No. 8, pp. 701-709.

Finger, C., "Caesarean Section Rates Skyrocket in Brazil. Many Women Are Opting for Caesareans in the Belief That it is a Practical Solution" Lancet (2003) vol. 362, No. 9384, p. 628.

Fisher, A et al., "Infant Gut Microbial Colonization and Health: Recent Findings from Metagenomics Studies" Journal of Integrated Omics (2012) vol. 2. Issue 1, pp. 1-16.

Gaskins, H.R. et al., "Impact of the Intestinal Microbiota on the Development of Mucosal Defense" Intestinal Microbiota and Mucosal Defense (2008) vol. 46 (Suppl 2), pp. S80-S86.

Gitig, D., "Hats Off to Bacteria!" The New York Academy of Sciences, Presented by Science & the City and the Sackler Institute of Nutrition Science, Academy eBriefings (2014), http://www.nyas.org/publications/Ebriefings/Detail.aspx?cid=82f, 3 pages total.

Goldberg, C., "Research: Could Birth-Canal Bacteria Help C-Section Babies?" Wbur's Common Health Reform and Reality (2014}, http://commonhealth.wbur.org/2014/06/birth-canal-bacteria-c-section, 4 pages total.

Graber, G.D., et al., "T Mycoplasma in Human Reproductive Failure" Obstetrics & Gynecology (1979) vol. 54, No. 5, pp. 558-561.

Hakansson, S. et al., "Caesarean Section Increases the Risk of Hospital Care in Childhood for Asthma and Gastroenteritis" Clinical and Experimental Allergy (2003) vol. 33, No. 6, pp. 757-764.

Hällstrom, M. et al., "Effects of mode of delivery and necrotising enterocolitis on the intestinal microflora in preterm infants" Eur J Clin Microbiol Infect Dis (2004) vol. 23, pp. 463-470, DOI: 10.1007/s10096-004-1146-0.

Heasman,L. et al. "Plasma prolactin concentrations after caesarean section or vaginal delivery" Archives of Disease in Childhood (1997) vol. 77, pp. F237-F238.

Hegde, S. et al.,"Influence of the maternal vaginal microbiota on the oral microbiota of the newborn" Europe PubMed Central Abstract, The Journal of Clinical Pediatric Dentistry (1998) vol. 22(4), pp. 317-321, http://europepmc.org/abstract/med/9796502.

Hesselmar, B. et al., "Pacifier Cleaning Practices and Risk of Allergy Development" Pediatrics Official Journal of The 32 American Academy of Pediatrics (2013) vol. 131, No. 6, DOI: 10.1542/peds.2012-3345, http://pediatrics.appublications.org/content/early/2013/04/30/peds.2012-3345, 12 pages total.

Huh, S.Y. et al., "Delivery by Caesarean Section and Risk of Obesity in Preschool Age Children: A Prospective Cohort Study" Arch Dis Child (2012) vol. 97, No. 7, pp. 610-616.

International Preliminary Report on Patentability Issued in International Application No. PCT/US2016/032576 dated Nov. 14, 2017, 8 pages.

International Search Report and Written Opinion Issued in PCT/US2016/068735 dated Mar. 31, 2017, 10 pages.

International Search and Written Opinion of the International Searching Authority Issued in International Application No. PCT/US2016/032576, dated Sep. 1, 2016 issued, 9 pages.

Jasarevic, E. et al., "A novel role for maternal stress and microbial transmission in early life programming and neurodevelopment" Neurobiology of Stress 1 (2015) pp. 81-88.

Kero, J. et al., "Mode of Delivery and Asthma—Is There a Connection?" Pediatric Research (2002) vol. 52, No. 1, pp. 7-11.

Kim, SW., "Treatment of Refractory or Recurrent Clostridium Difficile Infection" Korean J. Gastroenterol (2012) vol. 60, No. 2, pp. 71-78.

Koenig, J.E. et al., "Succession of Microbial Consortia in the Developing Infant Gut Microbiome" PNAS (2011) vol. 108, Suppl. 1, pp. 4578-4585.

Koren, O. et al., "Host Remodeling of the Gut Microbiome and Metabolic Changes During Pregnancy" Cell (2012) vol. 150, No. 3, pp. 470-480.

Lee, J. W. et al., "Lactobacillus colonization status in infants with urinary tract infection" Pediatr. Nephrol, (2009) vol. 24, pp. 135-139, DOI: 10.1007/s00467-008-0974-z.

Lee, P. W. et al., "A Study of Microbial Flora of Conjunctival Sac in Newborns" Kor. J. Ophthalmol. (1989) vol. 3, pp. 38-41.

Liakopoulos, A. et al. "Molecular characterization of *Streptococcus agalactiae* from vaginal colonization and neonatal infections: a 4-year multicenter study in Greece" Diagnostic Microbiology and Infectious Disease 78 (2014) pp. 487-490.

Litiaeva, LA. et al., "The effect of a combination of immune and bacterial preparations on the microbial ecology of pregnant women in a risk group" Europe PubMed Central Abstract, Akusherstvo i Ginekologiia [1993(1):19-22], http://europepmc.org/abstract/med/8317620, abstract.

Liu, D. et al., "Bacterial Community Structure Associated With Elective Cesarean Section Versus Vaginal Delivery in Chinese Newborns" JPGN (2015) vol. 60, pp. 240-246.

Iroha, EO et al., "Bacterial eye infection in neonates, a prospective study in a neonatal unit" Europe PubMed Central Abstract, West African Journal of Medicine (1998) vol. 17(3) pp. 168-172, http://europepmc.org/abstract/med/9814086.

Makino, H. et al., "Mother-to-Infant Transmission of Intestinal Bifidobacterial Strains Has an Impact on the Early Development of Vaginally Delivered Infant's Microbiota" PLoS ONE (2013) vol. 8, No. 11, pp. e78311-e78331.

Mandar, R. et al., "Transmission of Mother's Microflora to the Newborn at Birth" Biol Neonate. (1996) vol. 69, No. 1, pp. 30-35.

Marild, K. et al., "Pregnancy Outcome and Risk of Celiac Disease in Offspring: A Nationwide Case-Control Study" Gastroenterology (2012) vol. 142, No. 1, pp. 39-45.

Martin, R. et al., "Cultivation-independent assessment of the bacterial diversity of breast milk among healthy women" Res Microbiol. (2007) vol. 158, No. 1, pp. 31-37.

Martin, R. et al., "Human milk is a source of lactic acid bacteria for the infant gut" Journal of Pediatrics (2004) vol. 143, No. 6, pp. 754-758.

Mestquita, D.N. et al., "Cesarean Section is Associated with Increased Peripheral and Central Adiposity in Young Adulthood: Cohort Study" PLOS One (2013) vol. 8, No. 6, 8 pages total.

(56) References Cited

OTHER PUBLICATIONS

Mitsuda, T., "Demonstration of mother-to-infant transmission of *Staphylococcus aureus* by pulsed-field gel electrophoresis" European Journal of Pediatrics (1996) col. 155, No. 3, pp. 194-199.
Mshvildadze, M. et al., "Intestinal Microbial Ecology in Premature Infants Assessed Using Non-Culture Based Techniques" J. Pediatr. (2010) vol. 156, No. 1, pp. 20-25.
Mueller, NT et al., "The infant microbiome development: mom matters" Trends Mol. Med. (2015) vol. 21, No. 02, doi:10.1016/j.molmed.2014.12.002., pp. 109-117.
Mueller, NT et al., "Prenatal Exposure to Antibiotics, Cesarean Section and Risk of Childhood Obesity" Int J Obes (Lond) (2015) vol. 39, No. 4, pp. 665-670.
Naboka, I. et al, "Formation of digestive tract microflora of neonates in dynamics", Zh Mikrobiol Epidemiol Immunobiol, Abstract (2012) vol. 3. pp. 65-70, http://europepmc.org/abstract/med/22830277.
Neigh, A.S., "Microbes in Gastrointestinal Health and Disease" Gastroenterology (2009) vol. 136, No. 1, pp. 65-80.
Neu. J. et al., "Cesarean versus Vaginal Delivery: Long Term Infant Outcomes and the Hygiene Hypothesis" Clin Perinatol. (2011) vol. 38, No. 2, pp. 321-331, doi: 10.1016/j.clp.2011.03.008.
Ochman, H. et al., "Evolutionary Relationships of Wild Hominids Recapitulated by Gut Microbial Communities" PLOS Biology (2010) vol. 8, No. 11, 8 pages total.
OECD, "Health at a Glance 2011: OECD Indicators" OECD Publishing (2011) 204 pages total.
Palmer, C. al., "Development of the Human Infant Intestinal Microbiota" PLoS Biology (2007) vol. 05, No. 07, e177, pp. 1556-1573.
Pantoja-Feliciano, I.G. et al., "Biphasic Assembly of the Murine Intestinal Microbiota During Early Development" The ISME Journal (2013) vol. 7, pp. 1112-1115.
Pistiner, M. et al., "Birth by Cesarean Section, Allergic Rhinitis, and Allergic Sensitization among Children with Parental History of Atopy" J. Allergy Clin Immunol (2008) vol. 122, No. 2, pp. 274-279.
Pithva, S. et al., "Probiotic Attributes of Autochthonous Lactobacillus rhamnosus Strains of Human Origin" Appl Biochem Biotechnol. (2014) vol. 173, pp. 259-277, DOI 10.1007/S12010-014-0839-9.
Putignani, L. et al., "Additional maternal and nonmaternal factors contribute to microbiota shaping in newborns" PNAS (2010) vol. 107, No. 42, E159, 2 pages total.
Reed, R., "The Human Microbiome: considerations for pregnancy, birth and early mothering", Midwife Thinking (posted on Jan. 15, 2014), http://web.archive.org/web/20141101000800/http://midwifethinking.com, 8 pages total.
Reid, G. et al., "Microbiota Restoration: Natural and Supplemented Recovery of Human Microbial Communities," Nature Reviews Microbiology (2011) vol. 9, pp. 27-38.
Renz-Polster, H. et al., "Caesarean section delivery and the risk of allergic disorders in childhood" Clin. exp. Allergy (2005) vol. 35, No. 11, pp. 1466-1472, doi: 10.1111/j.1365-2222.2005.02356.x.
Roduit, C. et al., "Asthma at 8 years of age in children born by caesarean section" Thorax (2009) vol. 64, pp. 107-113, doi: 10.1136/thx.2008.100875.
Segata, N. et al., "Metagenomic Biomarker Discovery and Explanation" Genome Biology (2011) vol. 12, No. R60, pp. 1-18.
Sevelsted, A. et al., "Cesarean Section and Chronic Immune Disorders" Pediatrics (2014) vol. 135, No. 1, 9 pages total.
Siggers, R.H. et al., "Elective cesarean delivery affects gut maturation and delays microbial colonization but does not increase necrotizing enterocolitis in preterm pigs" Am J Physiol Regul Integr Comp Physiol (2008) vol. 294, R929-R938, doi:10.1152/ajpregu.00705.2007, 10 pages total.
Sima, "Can Missing Birth Canal Bacteria Be Restored to Cesarean Birth Babies?" Lacto Bacto (2015), pp. 1-6, http://lactobacto.com/2015/01 / 16/c an-missing-birth-canal-bacteria-be-restored-in-cesarean-births/.
Soares, P. et al., "Correcting for Purifying Selection: An Improved Human Mitochondrial Molecular Clock" The American Journal of Human Genetics (2009) vol. 84, pp. 740-759.
Thavagnanam, S. et al., "A Meta-Analysis of the Association Between Caesarean Section and Childhood Asthma" Clinical and Experimental Allergy (2007) vol. 38, pp. 629-633.
European Communication (Communication Pursuant to Rule 164(1) EPC) issued by the European Patent Office in European Application No. 16793665.7, dated Oct. 31, 2018, 17 pages total.
European Communication (Extended European Search Report) issued by the European Patent Office in European Application No. 16793665.7, dated Feb. 4, 2019, 14 pages total.
Van de Wijgert, J.H.H.M. et al., "The Vaginal Microbiota: What Have We Learned after a Decade of Molecular Characterization?" PLOS One (2014) vol. 9, Issue 8, e105998, 10 pages total.
Trosvik, P. et al., "Convergent temporal dynamics of the human infant gut microbiota" The ISME Journal (2010) vol. 04, pp. 151-158.
Turner, P., "The latest Trend After C-Section Delivery?" Seeding Baby's Microbiome, Shutterberg (2015), http://pattiturner.com/seeding-babys-microbiome/, 7 pages total.
Turroni, F. et al., "Diversity of Bifidobacteria within the Infant Gut Microbiota" PLOS one (2012) vol. 7, Issue 05, pp. 1-12.
Veleminsky, T. M. et al., "Relationship of vaginal microflora to PROM. pPROM and the risk of early-onset neonata sepsis" Neuro Endocrinology Letters (2008) vol. 29, No. 2, pp. 205-221, Europe PubMed Central—Abstract, 4 pages total.
Costello, E. K. et al., "Microbiome Assembly Across Multiple Body Sites in Low-Birthweight Infants" mBio (2013) vol. 4, Issue 6, pp. 1-12.

* cited by examiner

US 11,564,667 B2

DEVICE AND METHOD OF RESTORING MICROBIOTA OF NEWBORNS

CROSS-REFERENCE TO RELATED APPLICATIONS

This application is a U.S. National Phase of International Patent Application No. PCT/US16/68735, filed Dec. 27, 2016, which published as WO 2017/117142 A1 on Jul. 6, 2017, which claims priority to U.S. Provisional Application No. 62/271,692, filed on Dec. 28, 2015, the disclosure of which are herein incorporated by reference in their entirety.

STATEMENT AS TO FEDERALLY SPONSORED RESEARCH

This invention was made with government support under grant DK090989 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 22, 2016, is named 243735.000163_SL.txt and is 5,816 bytes in size.

FIELD OF THE INVENTION

The application relates to methods and devices for restoring normal microbiota in pre-term infants or infants delivered by Cesarean section and methods for preventing or ameliorating diseases associated with delivery by Cesarean section or pre-term birth comprising administering to said infants at the time of birth or shortly thereafter an effective amount of a vaginal microbiota inoculum obtained from the infant's mother or a donor during the third trimester of pregnancy before or at the time of giving birth or an effective amount of a probiotic composition, wherein said probiotic composition (i) stimulates growth and/or activity of bacteria which are under-represented in microbiota of said newborn as compared to vaginally delivered full-term newborns, and/or (ii) inhibits growth and/or activity of bacteria which are over-represented in microbiota of said newborn as compared to vaginally delivered full-term newborns. Also provided are methods for diagnosing abnormal microbiota development in a newborn, comprising determining a relative abundance of one or more bacterial taxa in a microbiota sample obtained from said newborn. Also provided are methods of using devices to assist in restoring normal natural maternal vaginal microbiota in newborns under non-natural vaginal delivery, and/or in pre-term or premature infants or infants delivered by Cesarean section.

BACKGROUND

Maternal vaginal microbes provide the natural seeding to the newborn microbiota (1). Whether vaginal microbes can reach the placenta and the fetus before labor initiates, still unclear (2, 3), but mode of delivery overwhelms any other possible previous signal, and C-section-born babies are microbiologically different from vaginally born infants (1). The maternal vaginal (4) and intestinal (5) microbiota change during the third trimester of pregnancy, but the significance of these changes for the fitness of the baby has not been understood. Early interaction with indigenous microbes is essential for healthy immunological and metabolic programming, and contact with bacterial populations in the vagina during birth marks the beginning of eventual massive bacterial colonization of the newborn's mucosal surfaces. Mucosal immunity is strongly influenced by the microbiota (6), which in the gut mucosa, is subject to continuous surveillance by M cells—from the Peyer's patches of the gut-associated lymphoid tissue (GALT)—for processing by local dendritic cells and subsequently modulate CD4+ to produce Tregs and induce tolerance.

The "education" of the immune system by the microbiota starts at the very first microbial exposure and pioneer bacteria probably play a determinant role. Few studies have focused on the development of the intestinal microbiota and immunity (7-10), but the assembly in multiple body sites, the fate of vaginal lactic acid bacterial populations, and the ecological dynamics between maternal and infant communities that interact are not known. Despite the vast descriptive knowledge about the microbiota of American adults generated by the HMP project (NIH), little is known about developmental aspects of the microbiota.

The incidence of immune, inflammatory, and metabolic disorders is increasing in industrialized countries (11, 12). Early life events and aberrant microbial colonization has been associated with these diseases (12, 13). Epidemiological associations show C-section delivery increased risk of asthma and allergies (14-21), intestinal inflammatory conditions (19, 22-24). Obesity and diabetes (type I) is also increased by C-section birthing (19, 25-29) and by antibiotic consumption (19, 27-30) even as early as during gestation (25).

The phenomenon of decreased oral and gut microbial diversity in the first days after birth, previously reported in mice (36), is of unknown functional significance, but might be reflecting the selective effect of milk on the gut microbiota. Bacteroides, Clostridiales and Bifidobacterium are bacteria that are enriched in the gut during the first weeks of life, during strict lactation.

Cesarean section birthing without maternal membrane rupture, as in the case of scheduled Cesarean, impedes the seeding of the babies with vaginal microbes. C-section is medically indicated in 13-15% of the births, saving many lives of mothers and babies. However, scheduled C-section is becoming the standard of birthing in many countries of the world, with over 50% of births in Brazil, Dominican Republic, and Iran and many other countries approaching these rates (Health at a Glance 2011: OECD Indicators; WHO Global Health Observatory; (31); (37)). C-section birthing is associated with short health risks for the mother and baby and with long term health risks for the babies, including celiac disease (23, 24), asthma (16, 20, 21, 38), type 1 diabetes (39, 40), and obesity (32, 41, 42).

Thus, there is a great need in the art for a device and method to capture and deliver, restoring, and/or improving normal microbiota from a mother to their newborn, particularly those under non-naturally vaginal delivery, and/or born in pre-term or premature.

SUMMARY OF THE INVENTION

As specified in the Background section above, there is a great need in the art for preventing or ameliorating diseases associated with delivery by Cesarean section or pre-term birth. The present application addresses these and other needs by providing methods for restoring normal microbiota in pre-term newborns or newborns delivered by Cesarean section and methods for treating (e.g., preventing or ameliorating) diseases associated with delivery by Cesarean section or pre-term birth comprising administering to said newborns at the time of birth or shortly thereafter an effective amount of maternal vaginal microbiota inoculum or an effective amount of a probiotic composition, wherein said probiotic composition (i) stimulates growth and/or activity of bacteria which are under-represented in microbiota of said newborn as compared to vaginally delivered full-term newborns, and/or (ii) inhibits growth and/or activity of bacteria which are over-represented in microbiota of said newborn as compared to vaginally delivered full-term newborns.

In one aspect, the invention provides a method for restoring normal microbiota in an infant delivered by Cesarean section, said method comprising administering to said infant at the time of birth and/or within the first 4 months of life (preferably, within the first 24 hours of life, most preferably within the first hour of life) an effective amount of a vaginal microbiota inoculum, wherein said inoculum is obtained from the subject's mother or from a donor during the third trimester of pregnancy before or at the time of giving birth.

In a related aspect, the invention provides a method for restoring normal microbiota in a pre-term infant, said method comprising administering to said infant at the time of birth and/or within the first 4 months of life (preferably, within the first 24 hours of life, most preferably, within the first hour of life) an effective amount of a vaginal microbiota inoculum, wherein said inoculum is obtained from the subject's mother or from a donor during the third trimester of pregnancy before or at the time of giving birth.

In a further aspect, the invention provides a method for treating (e.g., preventing or ameliorating) a disease in a subject associated with the subject's delivery by Cesarean section or with the subject's pre-term birth, said method comprising administering to said subject at the time of birth and/or within the first 4 months of life an effective amount of a vaginal microbiota inoculum, wherein said inoculum is obtained from the subject's mother or from a donor during the third trimester of pregnancy before or at the time of giving birth. In one embodiment, said disease is an inflammatory or an autoimmune disorder. In one embodiment, said disease is selected from the group consisting of autoimmune diseases, allergic diseases, infectious diseases, and rejection in organ transplantations. In one specific embodiment, said disease is selected from the group consisting of asthma, allergy, celiac disease, type 1 diabetes, obesity, necrotizing enterocolitis, inflammatory bowel disease (IBD), ulcerative colitis, Crohn's disease, sprue, autoimmune arthritis, rheumatoid arthritis, multiple sclerosis, graft vs. host disease following bone marrow transplantation, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, and atherosclerosis.

In one embodiment of any of the above methods of the invention, the vaginal microbiota inoculum is delivered to the mouth, nose, or skin of the infant. In one embodiment of any of the above methods of the invention, the vaginal microbiota is inoculum administered to the infant by a route selected from the group consisting of oral, topical, rectal, mucosal, sublingual, nasal, and via naso/oro-gastric gavage. In one embodiment of any of the above methods of the invention, the vaginal microbiota is administered to the infant by placing it on the maternal breast and/or chest.

In one embodiment of any of the above methods of the invention, the vaginal microbiota inoculum is delivered to the infant in a form of a liquid, foam, cream, spray, powder, or gel. In one embodiment of any of the above methods of the invention, the vaginal microbiota inoculum is delivered to the infant in a form of a composition which comprises (i) a carrier and/or excipient and/or (ii) one or more prebiotic agents which stimulate growth and/or activity of one or more bacteria present in the composition. In one specific embodiment, said composition comprises a buffering agent to adjust pH to the natural vaginal pH at the time of labor or to a pH of 3.5 to 7. In one specific embodiment, said composition comprises an excipient or a carrier that optimizes the seeding of the transferred microbiota.

In one embodiment of any of the above methods of the invention, the vaginal microbiota inoculum is delivered using an absorbent material or device (e.g., gauze, sponge, or tampon). In one specific embodiment, the vaginal microbiota inoculum is transferred to said absorbent material or device by introducing said absorbent material or device (e.g., for at least 5 minutes) in vagina prior to the birth or at the time of Cesarean section.

In one embodiment of any of the above methods, the vaginal microbiota inoculum, after it is obtained from the subject's mother or the donor, is stored in a frozen form.

In one embodiment of any of the above methods, the vaginal microbiota inoculum, after it is obtained from the subject's mother or the donor, is processed to isolate desired bacteria as single or mixed cultures and such mixed or single cultures are then administered to the infant.

In one embodiment of any of the above methods, the vaginal microbiota inoculum is lyophilized after it is obtained from the subject's mother or the donor and reconstituted prior to the administration to the infant.

In one embodiment of any of the above methods, prior to obtaining vaginal microbiota from the newborn's mother or the donor, it is verified that said mother or donor does not have Group B *Streptococcus* (GBS) and/or sexually transmitted diseases such as, e.g., human immunodeficiency virus (HIV) and/or *Chlamydia*. In one embodiment of any of the above methods, prior to obtaining vaginal microbiota from the newborn's mother or the donor, it is verified that said mother's or donor's vaginal pH is less than 4.5.

In one embodiment of any of the above methods of the invention, the newborn's mother or the donor has not been administered antibiotic compounds within a certain period prior to the collection of the microbiota (preferably, for at least one month prior to the collection of the microbiota), is not obese or overweight (preferably has body mass index (BMI) scores of below 25, most preferably between 18.5 and 24.9), and does not have irritable bowel disease, Crohn's disease, ulcerative colitis, irritable bowel syndrome, celiac disease, colorectal cancer, and a family history of these diseases.

In one embodiment of any of the above methods, the method further comprises monitoring the infant's microbiota after the administration of the vaginal microbiota by: (a) determining a relative abundance of one or more bacterial taxa in a microbiota sample obtained from the infant (e.g., isolated from feces, skin, oral mucosa, conjunctive mucosa, or nasal mucosa), and (b) comparing the relative abundance(s) determined in step (a) to (i) a predetermined standard value or (ii) to the abundance(s) of the same taxa in a control subject (e.g., a vaginally delivered full-term healthy infant) or (iii) to the average value of abundances of the same taxa in several control subjects. Non-limiting examples of the methods which can be used for determining the relative abundance of the bacterial taxa include, e.g., quantitative polymerase chain reaction (qPCR), sequencing of bacterial 16S rRNA, shotgun metagenome sequencing, and metabolomics. In one specific embodiment, the method involves determining a relative abundance of one or more bacteria from the taxa selected from the group consisting of *Lactobacillus, Bacteriodales, Bacteroides, Parabacteroides, Bacteroidacea, Porphyromonadaceae, Coriobacteriales, Bifidobacterium, Clostridiaceae, Stenotrophomonas,* and *Gemella*. In one specific embodiment, the method involves determining a relative abundance of one or more bacteria from the taxa recited in Table 1A. In one specific embodiment, the method involves determining a relative abundance of bacterial species recited in Table 1B. In one specific embodiment, the method involves determining a relative abundance of one or more bacteria from the family Neisseriaceae.

In a separate aspect, the invention provides a method for restoring normal microbiota in an infant delivered by Cesarean section, said method comprising administering to said infant at the time of birth and/or within the first 4 months of life an effective amount of a probiotic composition, wherein said probiotic composition (i) stimulates growth and/or activity of bacteria which are under-represented in microbiota of said infant as compared to vaginally delivered full-term infants, and/or (ii) inhibits growth and/or activity of bacteria which are over-represented in microbiota of said infant as compared to vaginally delivered full-term infants.

In a related aspect, the invention provides a method for restoring normal microbiota in a pre-term infant, said method comprising administering to said infant at the time of birth and/or within the first 4 months of life an effective amount of a probiotic composition, wherein said probiotic composition (i) stimulates growth and/or activity of bacteria which are under-represented in microbiota of said infant as compared to vaginally delivered full-term infants, and/or (ii) inhibits growth and/or activity of bacteria which are over-represented in microbiota of said infant as compared to vaginally delivered full-term infants.

In another aspect, the invention provides a method for treating (e.g., preventing or ameliorating) a disease in a subject associated with the subject's delivery by Cesarean section or with the subject's pre-term birth, said method comprising administering to said subject at the time of birth and/or within the first 4 months of life a therapeutically effective amount of a probiotic composition, wherein said probiotic composition (i) stimulates growth and/or activity of bacteria which are under-represented in microbiota of said infant as compared to vaginally delivered full-term infants, and/or (ii) inhibits growth and/or activity of bacteria which are over-represented in microbiota of said infant as compared to vaginally delivered full-term infants. In one embodiment, said disease is an inflammatory or an autoimmune disorder. In one embodiment, said disease is selected from the group consisting of autoimmune diseases, allergic diseases, infectious diseases, and rejection in organ transplantations. In one embodiment, said disease is selected from the group consisting of asthma, allergy, celiac disease, type 1 diabetes, obesity, necrotizing enterocolitis, inflammatory bowel disease (IBD), ulcerative colitis, Crohn's disease, sprue, autoimmune arthritis, rheumatoid arthritis, multiple sclerosis, graft vs. host disease following bone marrow transplantation, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, and atherosclerosis.

In one embodiment of any of the above methods involving administration of a probiotic composition, said probiotic composition comprises one or more bacterial strains from one or more taxa selected from the group consisting of *Lactobacillus, Bacteriodales, Bacteroides, Parabacteroides, Bacteroidacea, Porphyromonadaceae, Coriobacteriales Bifidobacterium, Clostridiaceae, Stenotrophomonas,* and *Gemella*. In one embodiment of any of the above methods involving administration of a probiotic composition, said probiotic composition comprises one or more bacterial strains from one or more taxa recited in Table 1A. In one embodiment of any of the above methods involving administration of a probiotic composition, said probiotic composition comprises one or more bacterial strains from one or more species recited in Table 1B. In one embodiment of any of the above methods involving administration of a probiotic composition, said probiotic composition comprises one or more OTUs which are independently characterized by, i.e., at least 95%, 96%, 97%, 98%, 99% or including 100% sequence identity to sequences listed in SEQ ID NOS 1-12 or 16S rRNA sequences of the bacterial species recited in Table 4 or Table 1B. In another embodiment, the OTUs may be characterized by one or more of the variable regions of the 16S rRNA sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. In one embodiment of any of the above methods involving administration of a probiotic composition, said probiotic composition comprises one or more bacterial strains which are independently characterized by, i.e., at least 95%, 96%, 97%, 98%, or 99% sequence identity to 16S rRNA sequences of the bacterial species recited in Table 1B or Table 4. In one embodiment of any of the above methods involving administration of a probiotic composition, said probiotic composition comprises one or more bacterial strains from the family Neisseriaceae. In one embodiment of any of the above methods involving administration of a probiotic composition, said probiotic composition augments the growth of at least one type of bacteria not detected in the probiotic or in the newborn's gastrointestinal (GI) tract, skin, mouth or any body site, prior to administration. In one embodiment of any of the above methods involving administration of a probiotic composition, said probiotic composition comprises one or more bacterial strains which can be found in a healthy vaginal microbiota from a pregnant woman in the third trimester of pregnancy before or at the time of giving birth. In one specific embodiment, said pregnant woman has not been administered antibiotic compounds within a certain period prior to the collection of the microbiota (preferably, for at least one month prior to the collection of the microbiota), is not obese or overweight (preferably has body mass index (BMI) scores of below 25, most preferably between 18.5 and 24.9), and does not have irritable bowel disease, Crohn's disease, ulcerative colitis, irritable bowel syndrome, celiac disease, colorectal cancer, and a family history of these diseases.

The probiotic composition useful in any of the above methods can comprise, without limitation, e.g., live bacterial cells, conditionally lethal bacterial cells, inactivated bacterial cells, killed bacterial cells, spores (e.g., germination-competent spores), recombinant carrier strains, cell extract, and bacterially-derived products (natural or synthetic bacterially-derived products such as, e.g., bacterial antigens or bacterial metabolic products).

In one embodiment of any of the above methods involving administration of a probiotic composition, said probiotic composition comprises (i) a carrier and/or excipient and/or (ii) one or more prebiotic agents which stimulate growth and/or activity of one or more bacteria present in the composition. In one specific embodiment, the probiotic composition comprises an excipient or a carrier that optimizes the seeding of one or more bacterial strains contained in said probiotic composition.

In one embodiment of any of the above methods involving administration of a probiotic composition, said probiotic composition is reconstituted from a lyophilized preparation. In one embodiment of any of the above methods involving administration of a probiotic composition, said probiotic composition comprises a buffering agent to adjust pH to the natural vaginal pH at the time of labor or to a pH of 3.5 to 7.

In one embodiment of any of the above methods involving administration of a probiotic composition, the probiotic composition is delivered to the mouth, nose, and/or skin of the infant and/or by placing it on the maternal breast and/or chest. In one embodiment, the probiotic composition is administered to the infant by a route selected from the group consisting of oral, topical, rectal (e.g., by enema), mucosal, sublingual, nasal, and via naso/oro-gastric gavage. In one embodiment, the probiotic composition is delivered to the infant in a form of a liquid, foam, cream, spray, powder, or gel. In one embodiment, the probiotic composition is delivered using an absorbent material or device (e.g., gauze, sponge, tampon, or other applicators). In one embodiment, the probiotic composition comprises a buffering agent (e.g., sodium bicarbonate, infant formula or sterilized human milk).

In one embodiment of any of the above methods involving administration of a probiotic composition, the probiotic composition is administered conjointly with a prebiotic which stimulates growth and/or activity of bacteria contained in the probiotic composition. Non-limiting examples of useful prebiotics include, e.g., fructooligosaccharides (FOS), galactooligosaccharides (GOS), human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, arabinose, maltose, lactose, sucrose, cellobiose, amino acids, alcohols, resistant starch (RS), and any mixtures thereof. In one specific embodiment, the prebiotic is derived from microorganisms that show stimulation by human milk components. In one specific embodiment, the probiotic and prebiotic are administered in one composition, or simultaneously as two separate compositions, or sequentially.

In a separate embodiment, the invention provides a method for diagnosing abnormal microbiota development in an infant, comprising: (a) determining a relative abundance of one or more bacterial taxa in a microbiota sample obtained from the infant, and (b) comparing the relative abundance(s) determined in step (a) to (i) a predetermined standard value or (ii) to the abundance(s) of the same taxa in a control subject or (iii) to the median value of abundances of the same taxa in several control subjects, wherein the control subject is a vaginally delivered full-term healthy infant. Non-limiting examples of the methods which can be used for determining the relative abundance of the bacterial taxa include, e.g., quantitative polymerase chain reaction (qPCR), sequencing of bacterial 16S rRNA, shotgun metagenome sequencing, and metabolomics. In one embodiment, the diagnostic method involves determining a relative abundance of one or more bacteria from one or more taxa selected from the group consisting of *Lactobacillus, Bacteriodales* (e.g., S24-7), *Bacteroides, Parabacteroides, Bacteroidacea, Porphyromonadaceae, Coriobacteriales Bifidobacterium, Clostridiaceae, Stenotrophomonas,* and *Gemella*. In one embodiment, the diagnostic method involves determining a relative abundance of one or more bacteria from one or more taxa present in a healthy vaginal microbiota from a pregnant woman in the third trimester of pregnancy before or at the time of giving birth. In one embodiment, the diagnostic method involves determining a relative abundance of one or more bacteria from one or more taxa recited in Table 1A. In one embodiment, the diagnostic method involves determining a relative abundance of one or more bacteria from one or more species recited in Table 1B. In one embodiment, the diagnostic method involves determining a relative abundance of one or more bacteria from the family Neisseriaceae.

In one embodiment of any of the above methods, the infant (or subject) is human. In one embodiment of any of the above methods, the infant is a newborn.

In another aspect, the invention provides a composition comprising (i) a vaginal microbiota inoculum and (ii) a carrier and/or excipient and/or one or more prebiotic agents which stimulate growth and/or activity of one or more bacteria present in the inoculum.

In a further aspect, the invention provides a probiotic composition comprising (a) one or more bacterial strains and (b) a carrier and/or excipient and/or one or more prebiotic agents which stimulate growth and/or activity of one or more of said bacterial strains, wherein said probiotic composition (i) stimulates growth and/or activity of bacteria which are under-represented in microbiota of an infant delivered by Cesarean section or born prematurely as compared to vaginally delivered full-term healthy infants, and/or (ii) inhibits growth and/or activity of bacteria which are over-represented in microbiota of said infant as compared to vaginally delivered full-term healthy infants. In one embodiment, the composition comprises two or more different bacterial strains.

Non-limiting examples of bacteria which can be present in any of the compositions of the invention comprise
(i) bacteria from one or more taxa selected from the group consisting of *Lactobacillus, Bacteriodales* (e.g., S24-7), *Bacteroides, Parabacteroides, Bacteroidacea, Porphyromonadaceae, Coriobacteriales, Bifidobacterium, Clostridiaceae, Stenotrophomonas,* and *Gemella;*
(ii) bacteria from one or more taxa recited in Table 1A;
(iii) bacteria from one or more species recited in Table 1B;
(iv) bacteria from family Neisseriaceae.

In one embodiment of any of the compositions of the invention, the composition comprises one or more OTUs which are independently characterized by, i.e., at least 95%, 96%, 97%, 98%, 99% or including 100% sequence identity to sequences listed in SEQ ID NOS 1-12 or 16S rRNA sequences of the bacterial species recited in Table 4 or Table 1B. In another embodiment, the OTUs may be characterized by one or more of the variable regions of the 16S rRNA sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. In one embodiment of any of the compositions of the invention, the composition comprises one or more bacterial strains which are independently characterized by, i.e., at least 95%, 96%, 97%, 98%, or 99% sequence identity to 16S rRNA sequences of the bacterial species recited in Table 1B or Table 4. In one embodiment of any of the compositions of the invention, the composition augments the growth of at least one type of bacteria not detected in the probiotic or in the newborn's gastrointestinal (GI) tract, skin, mouth, or any body site, prior to administration.

In one embodiment of any of the compositions of the invention, said composition comprises one or more bacterial strains which can be found in a healthy vaginal microbiota from a pregnant woman in the third trimester of pregnancy before or at the time of giving birth. In one specific embodiment, the woman has not been administered antibiotic compounds within a certain period prior to isolation of bacteria (preferably, for at least one month prior to isolation of bacteria), has body mass index (BMI) between 18.5 and 24.9, does not have Group B *Streptococcus* (GBS), human immunodeficiency virus (HIV), *Chlamydia*, and/or sexually transmitted diseases, has vaginal pH less than 4.5, and does not have irritable bowel disease, Crohn's disease, ulcerative colitis, irritable bowel syndrome, celiac disease, colorectal cancer or a family history of these diseases.

In one embodiment of any of the compositions of the invention, the composition comprises a buffering agent to adjust pH to the natural vaginal pH at the time of labor or to a pH of 3.5 to 7. In one embodiment of any of the compositions of the invention, the composition comprises an excipient or a carrier that optimizes the seeding of one or more bacterial strains contained in the composition. In one embodiment of any of the compositions of the invention, the composition is formulated for storage in a frozen form. In one embodiment of any of the compositions of the invention, said composition is a lyophilized composition. Any of the compositions of the invention can contain, e.g., live bacterial cells, conditionally lethal bacterial cells, inactivated bacterial cells, killed bacterial cells, spores (e.g., germination-competent spores), recombinant carrier strains, cell extract, or bacterially-derived products (natural or synthetic bacterially-derived products such as, e.g., bacterial antigens or metabolic products). In one embodiment of any of the compositions of the invention, the composition is formulated for delivery to the mouth, nose, and/or skin of the infant and/or for placing it on the maternal breast and/or chest. In one embodiment of any of the compositions of the invention, the composition is formulated for delivery by a route selected from the group consisting of oral, topical, rectal, mucosal, sublingual, nasal, and via naso/oro-gastric gavage. In one embodiment of any of the compositions of the invention, the composition is in a form of a liquid, foam, cream, spray, powder, or gel. In one embodiment of any of the compositions of the invention, the composition comprises a buffering agent (e.g., sodium bicarbonate, infant formula or sterilized human milk). In one embodiment of any of the compositions of the invention, the composition comprises a prebiotic which stimulates growth and/or activity of one or more bacteria contained in the composition. Non-limiting examples of useful prebiotics include, e.g., fructooligosaccharides (FOS), galactooligosaccharides (GOS), human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, arabinose, maltose, lactose, sucrose, cellobiose, amino acids, alcohols, resistant starch (RS), and any mixtures thereof.

In a related aspect, the invention provides an absorbent material or device (e.g., gauze, sponge, or tampon) comprising any of the compositions of the invention.

In another related aspect, the invention provides a method for restoring normal microbiota in an infant delivered by Cesarean section or a method for restoring normal microbiota in a pre-term infant, said method comprising administering to said infant at the time of birth and/or within the first 4 months of life an effective amount of any of the compositions of the invention.

In another related aspect, the invention provides a method for treating a disease in a subject associated with the subject's delivery by Cesarean section or with the subject's pre-term birth, said method comprising administering to said subject at the time of birth and/or within the first 4 months of life a therapeutically effective amount of any of the compositions of the invention.

It is also contemplated that when used to treat various diseases, the compositions and methods of the present invention can be utilized in combination with other therapeutic methods/agents suitable for the same or similar diseases. Such other therapeutic methods/agents can be co-administered (simultaneously or sequentially) to generate additive or synergistic effects. Suitable effective dosages for each agent may be lowered due to the additive action or synergy.

In one embodiment of any of the above methods, the infant (or subject) is human. In one embodiment of any of the above methods, the infant is a newborn.

As also specified in the Background Section above, there is a great need in the art for a device and method for capturing, delivering, restoring, and/or improving normal microbiota from a mother to their newborn. The present application addresses these and other needs by providing a device and method of using the device for collecting and restoring viable, bioactive, and diverse normal natural microbiota, in infants, particularly those under non-naturally vaginal delivery, such as through cesarean section, and/or those born in pre-term and/or premature conditions.

In one embodiment, a medium sterile pad gauze (J&J, 7.6×7.6 cm) folded like a fan and then in half, was wet with sterile saline solution and introduced in the maternal birth canal in the hour prior to the C-section, at the time antibiotics were administered. In certain embodiments, surgeon can extract the gauze prior to the procedure or any time before the surgical procedure, incubating the gauze in the birth canal for the time it takes to insert and extract, or for as long as 1 hour.

The invention contemplates in a broad scope any carriers, container, and/or devices suitable for holding the maternal vaginal fluids and/or microbiota in a suitable condition that is optionally a sterile condition. The invention also contemplates in a broad scope of devices for transferring, including but not limited to various absorbent materials in the form of gauze, sponge, tampon, etc., and/or via needle, tube, catheter, etc.

Certain embodiments of the invention can include a device to collect maternal vaginal microbiota from the vaginal canal of a patient. The device can have a housing forming a cavity, an absorbent removable material disposed within the cavity, and a deployment element disposed in the housing and movable along a length of the housing. The movement of the deployment element can displace the absorbent material out of the cavity and in to the vaginal canal.

Other embodiments of the device comprise an absorbent material that is not a material such as, but not limited to, a menstrual pad, a tampon, or a urine pad. Further, the housing and the deployment element can be sized to deliver the absorbent material within the lower ⅓ of the vaginal canal.

In a further embodiment, the absorbent. In other embodiments, the full length of the retrieval interface does not extend beyond the vaginal canal. Further, the retrieval interface can have a retrieval element capturing the deployed absorbent material followed by removal of the absorbent material from the vaginal canal. In some embodiments, the deployment element acts as the retrieval element. In other embodiments, the absorbent material has the retrieval interface. In certain embodiments, the retrieval element captures the deployed absorbent material by interacting with the retrieval interface. The retrieval element can also be disposed within the housing and capture and return the deployed absorbent material to the cavity for the removal of the absorbent material from the vaginal canal. Alternate embodiments have a second housing forming a second cavity and the retrieval element is disposed within the second housing and captures the deployed absorbent material and returns the absorbent material to the second cavity for the removal of the absorbent material from the vaginal canal.

In addition to the above embodiments, at least one of the housing, the cavity, the absorbent material and the deployment element can be sterile. Also, the housing can include a seal around at least one of the cavity and the absorbent material to maintain sterility. The deployment element can break the seal when deploying the absorbent material.

These and other aspects of the present invention will be apparent to those of ordinary skill in the art in the following description, claims and drawings.

BRIEF DESCRIPTION OF THE DRAWINGS

The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

The drawing figures depict one or more implementations in accord with the present teachings, by way of example only, not by way of limitation. In the figures, like reference numerals refer to the same or similar elements.

DETAILED DESCRIPTION

Figure 1:
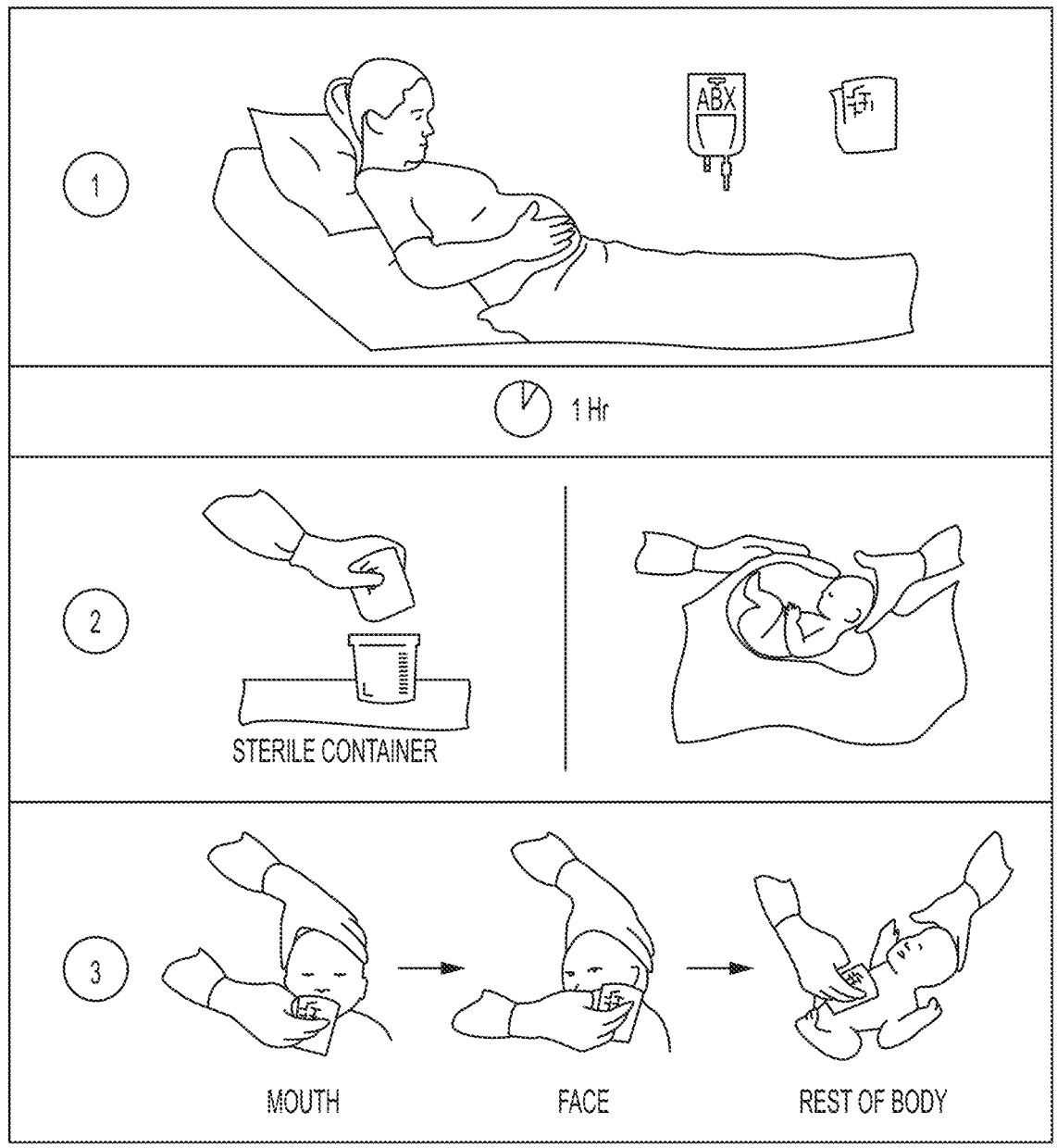
FIG. 1. Restoring the maternal microbiota in C-section born infants. When antibiotics are administered 1 hour prior to the C-section procedure, a gauze is inserted in the mothers' vagina, and extracted when the procedure starts. The gauze, kept in a sterile container, is used to swab the newborn as soon as possible after birth, starting with the mouth, face and rest of the body.

The present invention provides methods for restoring bioactivity and diversity of normal microbiota in pre-term newborns and/or newborns delivered by Cesarean section and methods for treating (e.g., preventing or ameliorating) diseases associated with delivery by Cesarean section or pre-term birth comprising administering to said newborns at the time of birth or shortly thereafter an effective amount of a vaginal microbiota inoculum obtained from the newborn's mother or a donor during the third trimester of pregnancy before or at the time of giving birth or an effective amount of a probiotic composition, wherein said probiotic composition (i) stimulates growth and/or activity of bacteria which are under-represented in microbiota of said newborn as compared to vaginally delivered full-term newborns, and/or (ii) inhibits growth and/or activity of bacteria which are over-represented in microbiota of said newborn as compared to vaginally delivered full-term newborns. Also provided are methods for diagnosing abnormal microbiota development in a newborn, comprising determining a relative abundance of one or more bacterial taxa in a microbiota sample obtained from said newborn Definitions As used herein, the terms "microbe" or "microorganism" encompass both prokaryotic organisms including bacteria and archaea, and eukaryotic organisms, including fungi, present in mammalian microbiota.

The terms "vaginal microbiota" or "vaginal flora" or "vaginal microbiome" are used interchangeably and refer to the microorganisms that colonize the vagina.

The term "restoring normal microbiota" is used herein to refer to restoring microbiota of an infant (e.g., skin, oral, nasal, gastrointestinal, or any other mucosal microbiota) to the level of bioactivity and diversity of corresponding microbiota of a healthy infant delivered naturally, i.e., through labor and vaginal exposure. This may also be considered as normalizing the microbiota, populating the microbiota, populating normal microbiota, preventing the onset of dysbiosis, or augmenting the growth of at least one type of bacteria in an infant. Preferably, such healthy naturally delivered "control" infant was born to a mother who has not been administered antibiotic compounds within a certain period prior to the delivery (preferably, for at least one month prior to the delivery), is not obese or overweight (preferably has body mass index (BMI) scores of below 25, most preferably between 18.5 and 24.9), does not have Group B *Streptococcus* (GBS), human immunodeficiency virus (HIV), *Chlamydia*, and/or sexually transmitted diseases, has vaginal pH less than 4.5, and does not have irritable bowel disease, Crohn's disease, ulcerative colitis, irritable bowel syndrome, celiac disease, colorectal cancer and a family history of these diseases.

Specific taxa and changes in microbiota discussed herein can be detected using various methods, including without limitation quantitative PCR (qPCR) or high-throughput sequencing (e.g., shotgun metagenome sequencing) methods which detect over- and under-represented genes in the total bacterial population (e.g., 454-sequencing for community analysis; screening of microbial 16S ribosomal RNAs (16S rRNA), etc.), or transcriptomic or proteomic studies that identify lost or gained microbial transcripts or proteins within total bacterial populations, or metabolomics. See, e.g., U.S. Patent Publication No. 2010/0074872; Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703.

As used herein, the term "16S rRNA sequencing" refers to the sequencing of 16S ribosomal RNA (rRNA) gene sequences by using primers such as universal primers and/or species-specific primers to identify the bacteria present in a sample. 16S rRNA genes contain both highly conserved sites and hypervariable regions that can provide species-specific signature sequences useful for identification of bacteria. Such universal primers are well known in the art.

As used herein, the term "operational taxonomic unit" or "OTU" refers to group of bacterial sequences that differ among each other in <97% identity. A "type" or a plurality of "types" of bacteria includes an OTU or a plurality of different OTUs, and also encompasses differences in species, genus, family or order of bacteria. The specific genetic sequence may be the 16S rRNA sequence or a portion of the 16S rRNA sequence or it may be a functionally conserved housekeeping gene found broadly across the eubacterial kingdom.

As used herein, the term "pre-term" as in pre-term newborn/infant or pre-term birth refers to any pre-term birth, including delivery before the 37-week gestation period. In some embodiments, pre-term includes any birth on or before about 37 weeks. In some embodiments, delivery is from about 37 weeks to 39 weeks. In some embodiments, delivery is from about 32 weeks to 37 weeks. In some embodiments, delivery is from about 32 weeks to 28 weeks. In some embodiments, delivery is from about 23 weeks to 28 weeks. References to weeks of gestation include part weeks, such that a reference to 32 weeks includes both 32 weeks and 0 days through 32 weeks and 6 days.

As used herein, the term "probiotic" refers to a substantially pure bacteria (i.e., a single isolate, of, e.g., live bacterial cells, conditionally lethal bacterial cells, inactivated bacterial cells, killed bacterial cells, spores, recombinant carrier strains), or a mixture of desired bacteria, bacteria components or bacterial extract, or bacterially-derived products (natural or synthetic bacterially-derived products such as, e.g., bacterial antigens or metabolic products) and may also include any additional components that can be administered to a mammal. Such compositions are also referred to herein as a "bacterial inoculant."

As used herein, the term "prebiotic" refers to an agent that increases the number and/or activity of one or more desired bacteria, enhancing their growth. Non-limiting examples of prebiotics useful in the methods of the present invention include fructooligosaccharides (e.g., oligofructose, inulin, inulin-type fructans), galactooligosaccharides, human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, other five- and six-carbon sugars (such as arabinose, maltose, lactose, sucrose, cellobiose, etc.), amino acids, alcohols, resistant starch (RS), and mixtures thereof. See, e.g., Ramirez-Farias et al., Br J Nutr (2008) 4:1-10; Pool-Zobel and Sauer, J Nutr (2007), 137:2580S-2584S.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "therapeutically effective amount" refers to the amount of a microbiota inoculum or probiotic that, when administered to a subject for treating (e.g., preventing or ameliorating) a state, disorder or condition, is sufficient to effect such treatment. The "therapeutically effective amount" will vary depending, e.g., on the bacteria or analogues administered as well as the disease and physical conditions and responsiveness of the subject to be treated.

As used herein, the phrase "pharmaceutically acceptable" refers to molecular entities and compositions that are generally regarded as physiologically tolerable.

As used herein, the term "combination" of a microbiota inoculum or probiotic and at least a second pharmaceutically active ingredient means at least two, but any desired combination of compounds can be delivered simultaneously or sequentially (e.g., within a 24 hour period).

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject (e.g., infant) is a human.

As used herein, the term "infant" refers to subjects from birth until the age when microbiome development is completed and encompasses newborn subjects. For humans, "infant" refers to subjects from birth to 3 years of age. In some embodiments, an infant treated using any of the methods or compositions of the invention is treated during the stage of development relevant (or critical) to microbiome development.

As used herein, the term "stimulate" when used in connection with growth and/or activity of bacteria encompasses the term "enhance".

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The terms "a," "an," and "the" do not denote a limitation of quantity, but rather denote the presence of "at least one" of the referenced item.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J. Additional techniques are explained, e.g., in U.S. Pat. No. 7,912,698 and U.S. Patent Appl. Pub. Nos. 2011/0202322 and 2011/0307437

Methods, Devices, and Compositions of the Invention

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The vertical transmission of microbiota from mother to child during labor and birth is highly conserved in mammals, suggesting evolutionary fitness (35). The present invention provides that major microbiota deficiencies at birth in preterm newborns or newborns delivered by Cesarean section can be restored by the exposure to maternal (or third trimester donor) vaginal microbiota or probiotics derived therefrom.

Microbiota donor subjects are generally of good health and have microbiota consistent with such good health. Often, the donor subjects have not been administered antibiotic compounds within a certain period prior to the collection of the microbiota (preferably, for at least one month prior to the collection of the microbiota). In certain embodiments, the donor subjects are not obese or overweight, and may have body mass index (BMI) scores of below 25, such as between 18.5 and 24.9. In other embodiments, the donor subjects do not have irritable bowel disease, Crohn's disease, ulcerative coliti), irritable bowel syndrome, celiac disease, colorectal cancer and a family history of these diseases. In other embodiments, donors have been screened for pathogens using standard techniques known to one in the art (e.g. nucleic acid testing, serological testing, antigen testing, culturing techniques, enzymatic assays, assays of cell free fecal filtrates looking for toxins on susceptible cell culture substrates).

In some embodiments, donors are also selected for the presence of certain genera and/or species that provide increased efficacy of therapeutic compositions containing these genera or species. In other embodiments, donors are preferred that produce relatively higher concentrations of spores than other donors. In further embodiments, donors are preferred that provide spores having increased efficacy; this increased efficacy can be measured using in vitro or animal studies. In some embodiments, the donor may be subjected to one or more pre-donation treatments in order to reduce undesired material in the collected microbiota, and/or increase desired spore populations.

It is advantageous to screen the health of the donor subject prior to and optionally, one or more times after, the collection of the microbiota material. Such screening identifies donors carrying pathogenic materials such as viruses (e.g., HIV, hepatitis, polio) and pathogenic bacteria. Post-collection, donors are screened about one week, two weeks, three weeks, one month, two months, three months, six months, one year or more than one year, and the frequency of such screening may be daily, weekly, bi-weekly, monthly, bi-monthly, semi-yearly or yearly. Donors that are screened and do not test positive, either before or after donation or both, are considered "validated" donors.

Methods for collection and preparation of vaginal microbiota are well known in the art. The vaginal microbiota can be stored, e.g., as frozen or lyophilized preparations (said lyophilized preparations can be reconstituted prior to the administration to the infant) or can be processed to isolate desired bacteria as single or mixed cultures and then stored. Vaginal microbiota and probiotics can be administered in various forms, including but not limited to, solid (e.g., powder), liquid, gel, cream, spray, foam, etc. The invention contemplates the use of various carriers, containers, and devices suitable for holding the vaginal microbiota in a suitable condition. For vaginal microbiota and live bacteria probiotic preparations, the carrier should preferably contain an ingredient that promotes viability of the bacteria during storage. The formulations can include added ingredients to improve palatability, improve shelf-life, impart nutritional benefits, and the like. In certain embodiments, the microbiota and probiotic preparations used in the methods of the invention comprise a buffering agent to adjust pH to the natural vaginal pH at the time of labor (pH of 3.5-7) or to a pH (3.5-7) that optimizes the seeding of the transferred microbiota.

The invention also contemplates in a broad scope any means for transferring, including but not limited to various absorbent materials (e.g., in the form of gauze, sponge, tampon, etc.), and/or needle, tube, catheter, etc. The vaginal microbiota can be transferred to absorbent material or device, e.g., by introducing said absorbent material or device in vagina prior to the birth or at the time of Cesarean section (e.g., for at least 5 minutes).

The invention provides that the collected vaginal microbiota or probiotics can be administered to any body part colonized in the newborns, including but not limited to, mouth, nasal mucosa, skin, etc. Alternatively (or in addition), vaginal microbiota or probiotics can be placed on the maternal breast and/or chest. Non-limiting examples of suitable routes of administration of vaginal microbiota and probiotics include oral (e.g., swabbing or via feeding tube or baby bottle), topical, rectal (e.g., by enema), mucosal, sublingual, nasal, and via naso/oro-gastric gavage. If a reproducible and measured dose is desired, the bacteria can be administered by a rumen cannula.

The dosages of the microbiota inoculum or probiotic administered in the methods of the invention will vary widely, depending upon the newborn's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization, e.g. $10^6$, $10^7$, $10^8$, $10^9$, and $10^{10}$ CFU for example, can be administered in a single dose. Lower doses can also be effective, e.g., $10^4$, and $10^5$ CFU.

Bacterial strains administered in probiotics according to the methods of the present invention can comprise live bacteria. One or several different bacterial inoculants can be administered simultaneously or sequentially (including administering at different times). Such bacteria can be isolated from vaginal microbiota and grown in culture using known techniques. However, many bacterial species are very difficult to culture and administration of others may lead to various undesirable side-effects. The present invention also comprises administering "bacterial analogues", such as recombinant carrier strains expressing one or more heterologous genes derived from the relevant bacterial species. The use of such recombinant bacteria may allow the use of lower therapeutic amounts due to higher protein expression. In certain embodiments, spores, killed bacterial cells and bacterial cell extracts can be utilized as the probiotics of the invention (see, e.g., Round et al., Proc. Natl. Acad. Sci. USA, 2010, 107: 12204). Bacteria in the compositions of the invention can be from one or more different species and can be, e.g., in the form of live bacterial cells, conditionally lethal bacterial cells, inactivated bacterial cells, killed bacterial cells, spores (e.g., germination-competent spores), recombinant carrier strains, cell extract, or bacterially-derived products (natural or synthetic bacterially-derived products such as, e.g., bacterial antigens or metabolic products).

In one specific embodiment, the composition comprises at least two different bacterial strains.

In one specific embodiment, the composition comprises bacteria from at least two different bacterial species. In some embodiments, the compositions comprise bacteria from at least 2, 3, 4, 5, 6, 7, 8, 9, 10, 50, 100, 200, 500, or 1000 different bacterial species.

In some embodiments, the composition comprises bacteria from at least one of the taxa provided in Table 1A. In some embodiments, the composition comprises bacteria from at least 2, 3, 4, 5, 6, 7, 8, 9, 10, 20, or 50 different taxa in Table 1A. In some embodiments, only nonpathogenic species within the taxa qualify for use in the compositions or methods herein.

TABLE 1A

Taxa for Inclusion in Compositions and Methods or for Microbiota Monitoring

| Family | | |
|---|---|---|
| Neisseriacea | | |
| | Genera | |
| Acinetobacter | Actinomyces | Aerococcus |
| Alloscardovia | Anaerococcus | Anaerostipes |
| Anoxybacillus | Asticcacaulis | Atopobium |
| Bacillus | Bacteroides | Bifidobacterium |
| Blastomonas | Bradyrhizobium | Brevibacterium |
| Campylobacter | Clavibacter | Cloacibacterium |
| Clostridium | Comamonas | Corynebacterium |
| Dermabacter | Devriesea | Dialister |
| Dorea | Enterococcus | Eremococcus |
| Erysipelatoclostridium | Escherichia | Ezakiella |
| Facklamia | Fastidiosipila | Fenollaria |
| Finegoldia | Fusobacterium | Gardnerella |
| Gemella | Haemophilus | Helcococcus |
| Herbaspirillum | Jonquetella | Kocuria |
| Kytococcus | Lactobacillus | Lactococcus |
| Leptotrichia | Levyella | Megasphaera |
| Methylobacillus | Methylobacterium | Micrococcus |
| Mobiluncus | Mycoplasma | Negativicoccus |
| Novosphingobium | Oceanitalea | Parabacteroides |
| Paracoccus | Parvimonas | Pelistega |
| Peptococcus | Peptoniphilus | Peptostreptococcus |
| Polaromonas | Porphyromonas | Prevotella |
| Pseudoclavibacter | Pseudomonas | Rothia |
| Rubrobacter | Ruminococcus | Sneathia |
| Sphingobium | Sphingopyxis | Staphylococcus |
| Stenotrophomonas | Streptococcus | Sutterella |
| Ureaplasma | Varibaculum | Veillonella |
| Veillonella | 1-68 | |
| Bacteroidacea | Porphyromonadaceae | Coriobacteriales |
| Clostridiaceae | Bacteriodales | |

In some embodiments, the composition comprises bacteria from at least one of the species provided in Table 1B. In some embodiments, the composition comprises bacteria from at least 2, 3, 4, 5, 6, 7, 8, 9, 10, 20, 50, 100, or 150 different bacterial species in Table 1B. In some embodiments, at least some of the bacteria chosen from Table 1B are in different genera, including, but not limited to 2, 3, 4, 5, 6, 7, 8, 9, 10, 20, or 50 different genera. In other embodiments, at least some of the bacteria chosen from Table 1B are in the same genera.

TABLE 1B

Species for Inclusion in Compositions and Methods or for Microbiota Monitoring

| | | |
|---|---|---|
| *Acinetobacter baumannii* | *Acinetobacter gerneri* | *Acinetobacter johnsonii* |
| *Acinetobacter radioresistens* | *Acinetobacter schindleri* | *Acinetobacter seifertii* |
| *Acinetobacter variabilis* | *Actinomyces europaeus* | *Actinomyces neuii* |
| *Aerococcus christensenii* | *Alloscardovia omnicolens* | *Anaerococcus lactolyticus* |
| *Anaerococcus murdochii* | *Anaerococcus obesiensis* | *Anaerococcus octavius* |
| *Anaerococcus prevotii* | *Anaerococcus provenciensis* | *Anaerococcus vaginalis* |
| *Anaerostipes hadrus* | *Anoxybacillus flavithermus* | *Asticcacaulis excentricus* |
| *Atopobium deltae* | *Atopobium vaginae* | *Bacillus vireti* |
| *Bacteroides finegoldii* | *Bacteroides vulgatus* | *Bifidobacterium breve,* |
| *Bifidobacterium pseudolongum* | *Blastomonas natatoria* | *Bradyrhizobium lupini* |
| *Brevibacterium paucivorans* | *Campylobacter coli* | *Campylobacter hominis* |
| *Campylobacter ureolyticus* | *Clavibacter michiganensis* | *Cloacibacterium rupense* |
| *Clostridium clostridioforme* | *Clostridium perfringens* | *Comamonas serinivorans* |
| *Comamonas testosterone* | *Corynebacterium amycolatum* | *Corynebacterium appendicis* |
| *Corynebacterium argentoratense* | *Corynebacterium aurimucosum* | *Corynebacterium canis* |
| *Corynebacterium casei* | *Corynebacterium coyleae* | *Corynebacterium freneyi* |
| *Corynebacterium imitans* | *Corynebacterium jeikeium* | *Corynebacterium kroppenstedtii* |
| *Corynebacterium lactis* | *Corynebacterium matruchotii* | *Corynebacterium mycetoides* |
| *Corynebacterium mycetoides* | *Corynebacterium pilbarense* | *Corynebacterium pyruviciproducens* |
| *Corynebacterium spheniscorum* | *Corynebacterium striatum* | *Corynebacterium terpenotabidum* |
| *Corynebacterium thomssenii* | *Corynebacterium tuberculostearicum* | *Corynebacterium tuscaniense* |
| *Dermabacter hominis* | *Devriesea agamarum* | *Dialister micraerophilus* |
| *Dialister propionicifaciens* | *Dialister succinatiphilus* | *Dorea longicatena* |
| *Enterococcus hirae* | *Eremococcus coleocola* | *Erysipelatoclostridium ramosum* |
| *Escherichia marmotae* | *Ezakiella peruensis* | *Facklamia hominis* |
| *Facklamia ignava* | *Fastidiosipila sanguinis* | *Fenollaria massiliensis* |
| *Finegoldia magna* | *Fusobacterium equinum* | *Fusobacterium nucleatum* |
| *Fusobacterium periodonticum* | *Fusobacterium simiae* | *Gardnerella vaginalis* |
| *Gemella asaccharolytica,* | *Gemella taiwanensis* | *Haemophilus pittmaniae* |
| *Helcococcus sueciensis* | *Herbaspirillum chlorophenolicum* | *Jonquetella anthropic* |
| *Kocuria flava* strain HO-9041 | *Kocuria kristinae* strain DSM 20032 | *Kytococcus schroeteri* strain Muenster 2000 |
| *Lactobacillus coleohominis* | *Lactobacillus crispatus* | *Lactobacillus hominis* |
| *Lactobacillus iners* | *Lactobacillus intestinalis* | *Lactobacillus jensenii* |
| *Lactobacillus psittaci* | *Lactobacillus reuteri* | *Lactobacillus rodentium* |
| *Lactococcus lactis* | *Levyella massiliensis* | *Methylobacillus flagellates* |
| *Methylobacterium aerolatum* | *Methylobacterium phyllostachyos* | *Micrococcus aloeverae* strain AE-6 |
| *Mobiluncus curtisii* | *Mycoplasma hominis* | *Negativicoccus succinicivorans* |
| *Oceanitalea nanhaiensis* | *Parabacteroides faecis* | *Parabacteroides merdae* |
| *Paracoccus communis* | *Parvimonas micra* | *Pelistega indica* |
| *Peptococcus niger* | *Peptoniphilus coxii* | *Peptoniphilus duerdenii* |
| *Peptoniphilus grossensis* | *Peptoniphilus koenoeneniae* | *Peptoniphilus lacrimalis* |
| *Peptoniphilus obesi* strain ph1 | *Peptoniphilus senegalensis* | *Peptoniphilus tyrrelliae* |
| *Peptostreptococcus anaerobius* | *Polaromonas sp* | *Porphyromonas bennonis* |
| *Porphyromonas somerae* | *Porphyromonas uenonis* | *Prevotella amnii* |
| *Prevotella bergensis* | *Prevotella bivia* | *Prevotella buccalis* |
| *Prevotella copri* | *Prevotella corporis* | *Prevotella disiens* |
| *Prevotella timonensis* | *Pseudoclavibacter bifida* strain IAM 14848 | *Pseudomonas brenneri* |
| *Pseudomonas helmanticensis* | *Pseudomonas lini* | *Pseudomonas syringae* |
| *Rothia amarae* strain J18 | *Rothia mucilaginosa* | *Rubrobacter calidifluminis* |
| *Ruminococcus bromii* | *Ruminococcus gnavus* | *Sneathia sanguinegens* |
| *Sphingobium yanoikuyae* | *Sphingopyxis macrogoltabida* | *Staphylococcus carnosus* |
| *Staphylococcus chromogenes* | *Staphylococcus petrasii* | *Staphylococcus pseudintermedius* |
| *Staphylococcus saprophyticus* | *Stenotrophomonas maltophilia* | *Streptococcus agalactiae* |
| *Streptococcus anginosus* | *Streptococcus constellatus* | *Streptococcus dentisani* |
| *Streptococcus lactarius* | *Streptococcus thermophiles* | *Sutterella stercoricanis* |
| *Ureaplasma urealyticum* | *Varibaculum cambriense* | *Veillonella dispar* |
| *Veillonella ratti* | *Bacteriodales S24-7* | |

Within a given composition, different bacterial strains can be contained in equal amounts (even combination) or in various proportions (uneven combinations) needed for achieving the maximal biological activity. For example, in a bacterial composition with two bacterial strains, the strains may be present in from a 1:10,000 ratio to a 1:1 ratio, from a 1:10,000 ratio to a 1:1,000 ratio, from a 1:1,000 ratio to a 1:100 ratio, from a 1:100 ratio to a 1:50 ratio, from a 1:50 ratio to a 1:20 ratio, from a 1:20 ratio to a 1:10 ratio, from a 1:10 ratio to a 1:1 ratio. For bacterial compositions comprising at least three bacterial strains, the ratio of strains may be chosen pairwise from ratios for bacterial compositions with two strains. For example, in a bacterial composition comprising bacterial strains A, B, and C, at least one of the ratios between strain A and B, the ratio between strain B and C, and the ratio between strain A and C may be chosen, independently, from the pairwise combinations above. In one embodiment, two or more bacterial strains in the composition produce synergistic activity. In one specific embodiment, the invention encompasses administering two or more bacteria-containing compositions to the same subject. Such compositions can be administered simultaneously or sequentially.

Spores used in the compositions of the invention can me isolated, for example, by solvent treatments (e.g., using partially miscible, fully miscible or an immiscible solvent), chromatographic treatments (e.g., using hydrophobic interaction chromatography (HIC) or an affinity chromatography), mechanical treatments (e.g., blending, mixing, shaking, vortexing, impact pulverization, and sonication), filtration treatments, thermal treatments (e.g., 30 seconds in a 100° C. environment followed by 10 minutes in a 50° C.), irradiation treatments (e.g., with ionizing radiation, typically gamma irradiation, ultraviolet irradiation or electron beam irradiation provided at an energy level sufficient to kill pathogenic materials while not substantially damaging the desired spore populations), centrifugation and density separation treatments (e.g., using density or mobility gradients or cushions (e.g., step cushions), such as, e.g., CsCl, Percoll, Ficoll, Nycodenz, Histodenz or sucrose gradients). It is generally desirable to retain the spore populations under non-germinating and non-growth promoting conditions and media, in order to minimize the growth of pathogenic bacteria present in the spore populations and to minimize the germination of spores into vegetative bacterial cells.

The compositions of the invention can comprise a carrier and/or excipient. While it is possible to use a bacterial inoculant or compound of the present invention for therapy as is, it may be preferable to administer it in a pharmaceutical formulation, e.g., in admixture with a suitable pharmaceutical excipient and/or carrier selected with regard to the intended route of administration and standard pharmaceutical practice. The excipient and/or carrier must be "acceptable" in the sense of being compatible with the other ingredients of the formulation and not deleterious to the recipient thereof. Acceptable excipients and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient and carrier can be selected with regard to the intended route of administration and standard pharmaceutical practice. Oral formulations readily accommodate additional mixtures, such as, e.g., milk, yogurt, and infant formula. Solid dosage forms for oral administration can also be used and can include, e.g., capsules, tablets, caplets, pills, troches, lozenges, powders, and granules. Non-limiting examples of suitable excipients include, e.g., diluents, buffering agents (e.g., sodium bicarbonate, infant formula, sterilized human milk, or other agents which allow bacteria to survive and grow [e.g., survive in the acidic environment of the stomach and to grow in the intestinal environment]), preservatives, stabilizers, binders, compaction agents, lubricants, dispersion enhancers, disintegration agents, antioxidants, flavoring agents, sweeteners, and coloring agents. Those of relevant skill in the art are well able to prepare suitable solutions.

The bacteria-containing formulations of the invention may comprise one or more prebiotics which promote growth and/or activity of the bacteria in the formulation.

Non-limiting examples of prebiotic agents useful in the methods of the present invention include fructooligosaccharides (e.g., oligofructose, inulin, inulin-type fructans), galactooligosaccharides, human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, other five and six-carbon sugars (e.g., arabinose, maltose, lactose, sucrose, cellobiose, etc.), amino acids, alcohols, resistant starch (RS), and mixtures thereof. Additional prebiotic agents can be selected based on the knowledge of particular bacteria.

Methods for producing bacterial compositions of the invention may include three main processing steps, combined with one or more mixing steps. The steps are: organism banking, organism production, and preservation. For banking, the strains included in the bacterial compositions of the invention may be (1) isolated directly from a specimen or taken from a banked stock, (2) optionally cultured on a nutrient agar or broth that supports growth to generate viable biomass, and (3) the biomass optionally preserved in multiple aliquots in long-term storage. The bacterial suspension can be freeze-dried to a powder and titrated. After drying, the powder may be blended to an appropriate potency, and mixed with other cultures and/or a filler such as microcrystalline cellulose for consistency and ease of handling, and the bacterial composition formulated as provided herein.

Additional methods include methods of evaluating the microbiota population in a subject or diagnosing an abnormal microbiota development. Methods include monitoring the infant's microbiota after the administration of the vaginal microbiota inoculum or probiotic by: (a) determining a relative abundance of one or more bacterial taxa in a microbiota sample obtained from the infant, and (b) comparing the relative abundance(s) determined in step (a) to (i) a predetermined standard value or (ii) to the abundance(s) of the same taxa in a control subject or (iii) to the average value of abundances of the same taxa in several control subjects. The newborn's sample may be isolated from feces, skin, oral mucosa, conjunctival mucosa, or nasal mucosa. It may be compared to a control subject who is a vaginally delivered full-term healthy infant. The control subject may be born to a mother who has not been administered antibiotic compounds within a certain period prior to giving birth (preferably, for at least one month prior to giving birth), has body mass index (BMI) between 18.5 and 24.9, and does not have irritable bowel disease, Crohn's disease, ulcerative colitis, irritable bowel syndrome, celiac disease, colorectal cancer, and a family history of these diseases.

The relative abundance of the taxa may comprise a method selected from the group consisting of quantitative polymerase chain reaction (qPCR), sequencing of bacterial 16S rRNA, shotgun metagenome sequencing, and metabolomics.

In accordance with the present invention there may be numerous tools and techniques within the skill of the art, such as those commonly used in molecular biology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

In some non-limiting embodiments, the compositions of the invention are formulated as pharmaceutical preparations for oral, topical, nasal, rectal, mucosal, sublingual, or nasal administration. In some embodiments, the formulation is a slow release formulation. In some embodiments, the compositions are formulated as medical foods, nutritional or dietary supplements, food products or beverage products The invention also contemplates in a broad scope any means for transferring, including but not limited to, various absorbent materials (e.g., in the form of gauze, sponge, tampon, etc.), and/or needle, tube, catheter, etc. The vaginal microbiota can be transferred to an absorbent material or device, e.g., by introducing said absorbent material or device into the vagina prior to the birth or at the time of Cesarean section (e.g., for at least 1 second, at least 3 seconds, at least 5 seconds, at least 10 seconds, at least 20 seconds, at least 30 seconds, at least 40 seconds, at least 50 seconds, at least 1 minute, at least 2 minutes, at least 3 minutes, at least 4 minutes, or at least 5 minutes).

The examples of devices and methods of using the devices of the present invention enable a physician to collect and restore the maternal microbiota in C-section born infants. This primary example is illustrated in FIG. 1. Prior to the C-section procedure, the absorbent material or device is inserted in the mother's vagina and extracted when the procedure starts. This is illustrated in step 1. The absorbent material or device is kept in a sterile container, for example, either in a separate container or in the original housing as described below. The absorbent material or device with the collected vaginal microbiota is stored during the delivery procedure. See, step 2. As soon as possible after birth the absorbent material or device is retrieved and is used to swab the infant, starting with the mouth, face, and rest of the body. This is illustrated in step 3.

Storage, as used in some examples, can involve differing ranges of temperatures depending on the when the collected microbiota is used. In some circumstances when the microbiota can be swabbed onto the infant within a short amount of time after collection (e.g., 1 to 2 hours) the absorbent material or device with the collected vaginal microbiota can be stored at a temperature between the vaginal temperature and room temperature. For longer term storage, typically for future use (i.e. not to be used with child being born at the time of collection), the maternal microbiota can be stored at temperatures that will preserve the maternal microbiota for long periods. In some examples, the storage temperature can be below freezing. These freezing temperatures can range from just below the freezing point to deep freezing tens or even hundred degrees below the freezing point. The temperature used can be dictated by the need for long term preservation and harmful effects to the stored maternal microbiota. In certain embodiments, the microbiota is stored at ultralow temperatures. In additional embodiments, the microbiota is stored in a media containing 15% glycerol. In certain embodiments, the 15% glycerol helps to preserve cell viability.

Figure 6:
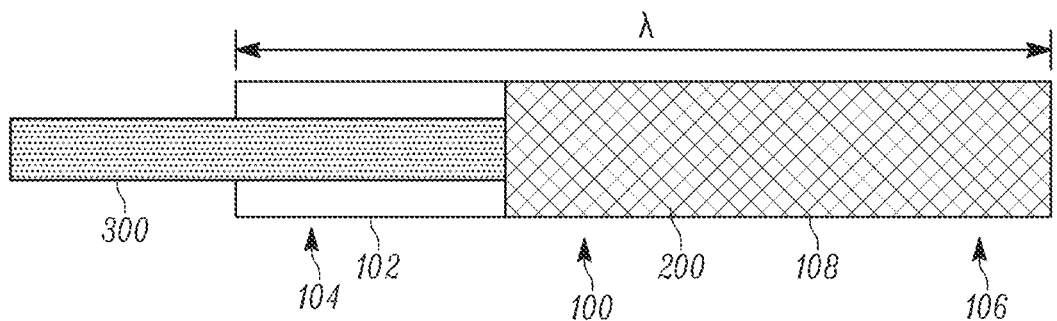

FIG. 6 illustrates a device 100 to collect the maternal microbiota, which includes a housing 102 designed to be inserted into the vagina of the expecting mother prior to delivery of the infant. The housing 102 has a proximal end 104 and a distal end 106 and can enclose a cavity 108. The cavity 108 can hold an absorbent material 200 which can be deployed into the vagina to collect the maternal vaginal fluids, and/or the maternal vaginal microbiota. The distance between the proximal and distal ends 104,106 can describe a housing length λ.

In an embodiment, the proximal end 104 of the housing 102 can have a deployment/retrieval element 300 to deploy the absorbent material 200 once the housing 102 is placed in the vagina, and it can be deployed out of the distal end 106. In certain embodiments, the deployment/retrieval element 300 is slidable along at least a part of the housing length λ. This includes the ability to be slidable within the cavity 108. The deployment/retrieval element 300 can also be removable from the housing 102.

One embodiment, the deployment/retrieval element 300 can deploy the absorbent material 200 followed by the removal of the housing 102. The absorbent material 200 can then be removed with a second device, having a second housing/cavity or by a medical professional (e.g., surgeon) prior to the delivery of the baby. In other aspects, the absorbent material 200 is deployed and after a predetermined amount of time, the absorbent material 200 is retrieved by the same device 100. In certain embodiments, the device 100 can remain inside the vagina for the duration of the collection of the maternal vaginal fluids, and/or the maternal vaginal microbiota or can be removed after deployment of the absorbent material 200 and reintroduced to retrieve the absorbent material 200.

The above situations lead to different embodiment of the device 100 and its elements. In an example, the one or more of the device 100, housing 102, absorbent material 200, deployment/retrieval element 300 and cavity 108, and portions thereof, can be sterilized. This can be as simple as sterilizing the device in an autoclave prior to use or factory sterilization and sterile packaging. Other embodiments can include a seal 112 that seals the cavity 108, and/or the proximal 104 and distal 106 ends. In certain embodiments, the seal 112 makes just those sections (e.g., 108, 104, and 106) sterile environments.

Figure 7A:
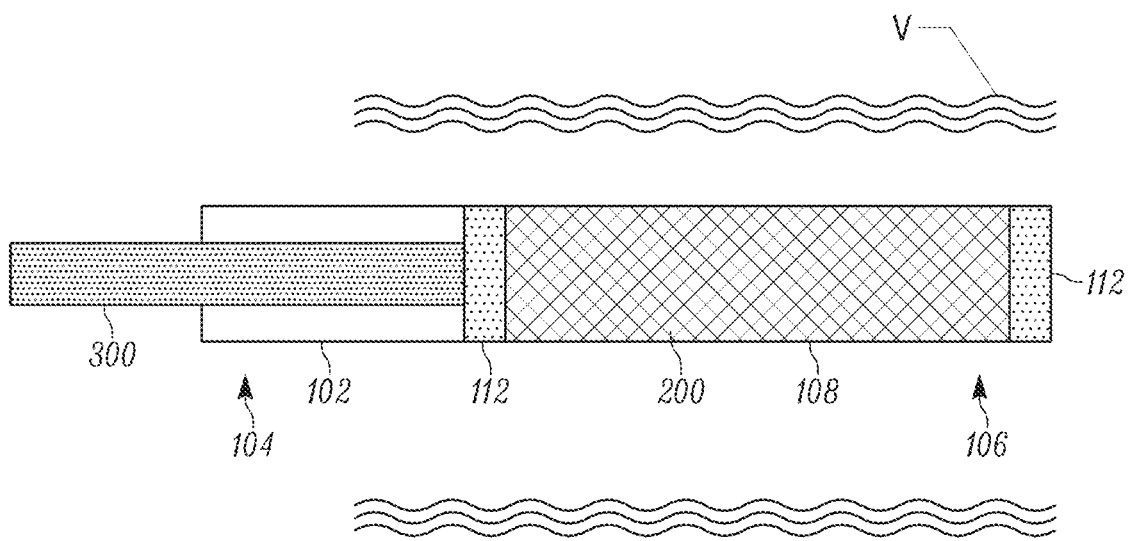
FIGS. 7A-7C. Illustrates the deployment of the absorbent material.
Figure 7B:
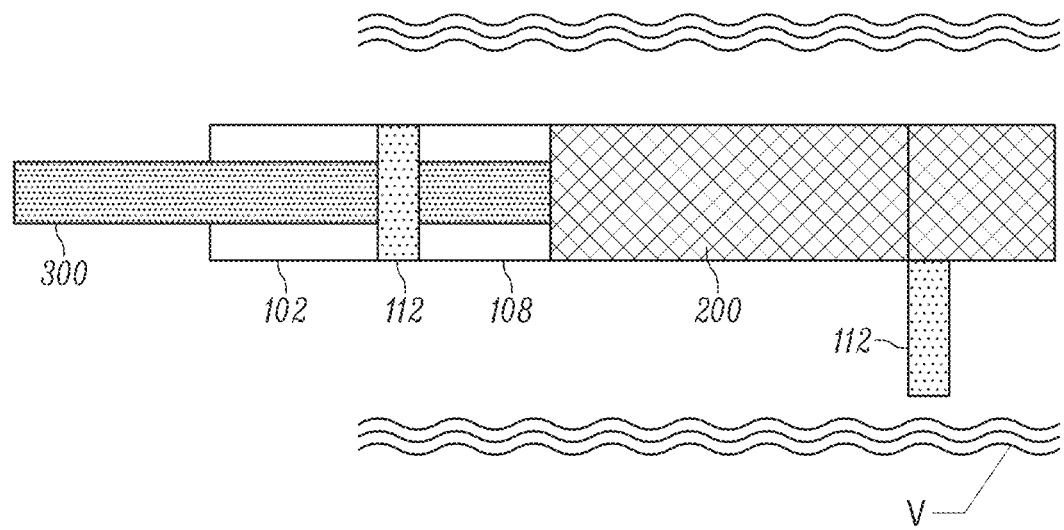
Figure 7C:
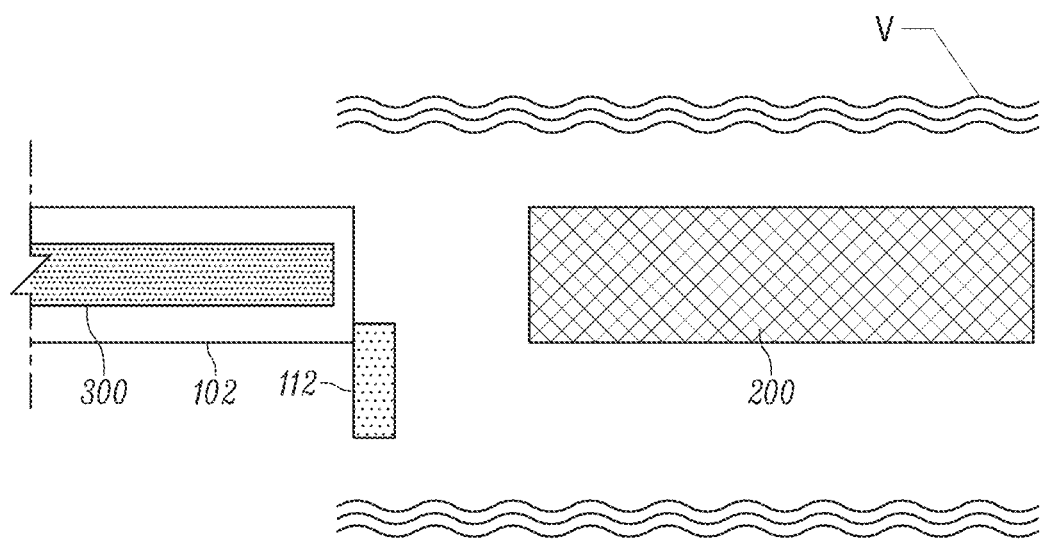

In FIG. 7A it is illustrated that the cavity 108 containing the absorbent material 200 is sealed 112 at both ends. The cavity 108 can be a sterile environment or the absorbent material 200 can be in sterile wrapping and the seals 112 are surrounding the absorbent material 200. Once the housing 102 is inserted into the vagina the absorbent material 200 can be deployed. The act of deployment can break the seal(s) 112 so the absorbent material 200 is sterile as it enters the vagina. This can be caused by the pressure of the absorbent material 200 against the seal(s) 112 as it is being deployed or a feature of the deployment element 300 that breaks the seal 112 prior to, or as, the absorbent material 200 is being deployed. FIG. 7B illustrates this deployment and FIG. 7C illustrates the fully deployed absorbent material 200 and the partial removal of the housing 102. In some examples, the delivery device 100 can be designed to deliver the absorbent material 200 no farther than the lower third of the vaginal canal V.

Figure 8A:
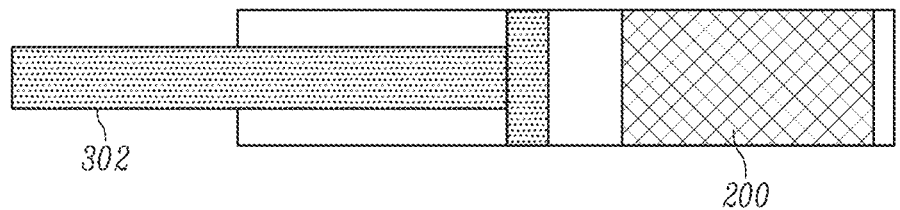
FIGS. 8A-8H. Illustrates multiple examples of the deployment and retrieval devices.
Figure 8B:
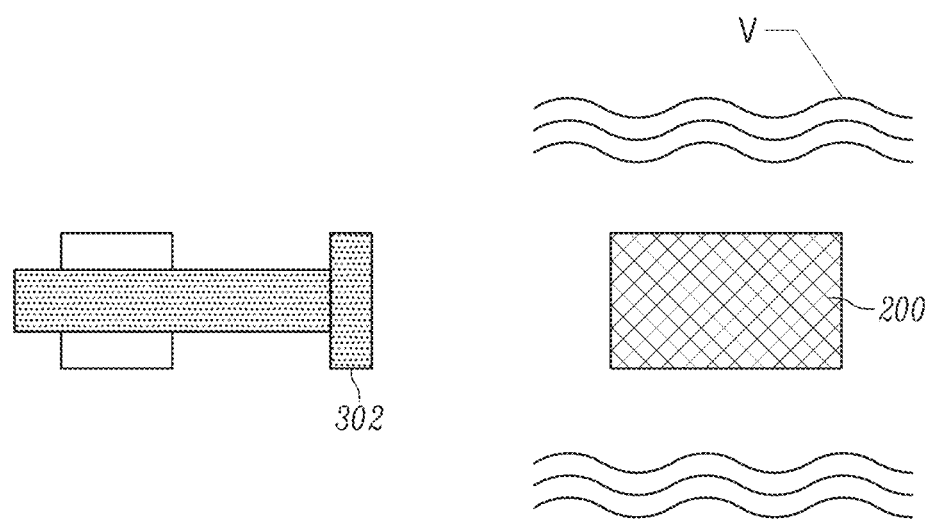
Figure 8C:
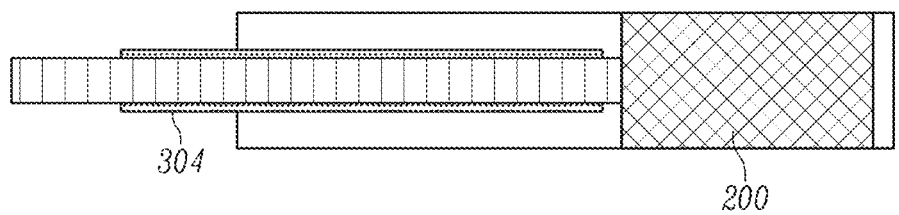
Figure 8D:
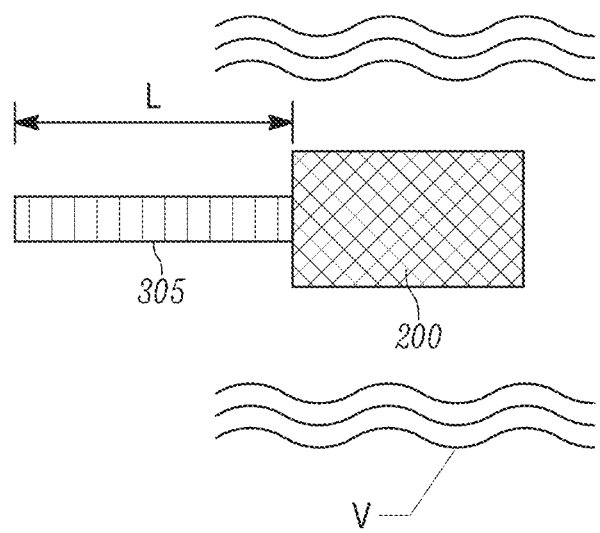

There are many embodiments of the deployment element 300. As illustrated in FIGS. 8A-8B, the deployment element 300 can be as simple as a plunger-type device 302 which is partially exposed outside the distal end 106. In certain embodiments, as the user pushes on the plunger 302, it is moved into the cavity 108 to displace the absorbent material 200 and forces it out the proximal end 104. Other embodiments can have the deployment element 300 also retrieve the absorbent material 200. For example, deployment/retrieval element 304 can be tethered to the absorbent material 200 so that operation of the element 304 can pull the absorbent material 200 back into the cavity for retrieval and removal from the vagina. As illustrated in FIGS. 8C and 8D, this can be tether 305.

Figure 8E:
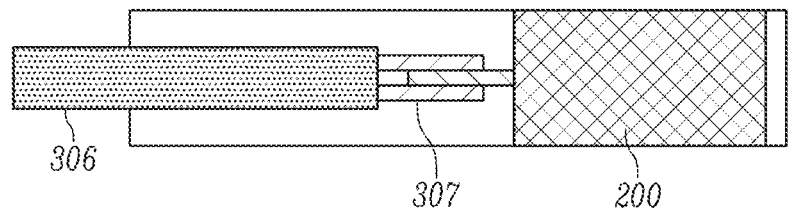
Figure 8F:
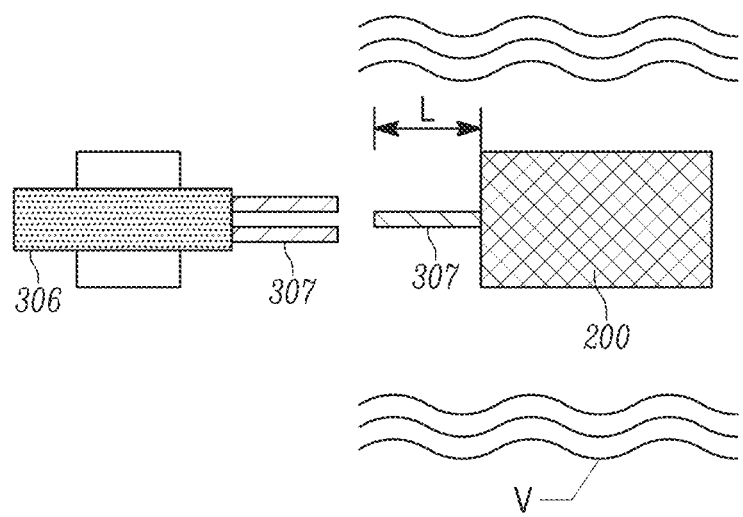

Other deployment and retrieval elements 306 can be unattached to the absorbent material 200 but designed to grab or capture the material through the use of a reattachable interface 307. The reattachable interface can be, for example, mating hook and loop material on each of the element 306 and the absorbent material 200, attractive magnets, or a particular male/female locking point. See FIGS. 8E and 8F.

Figure 8G:
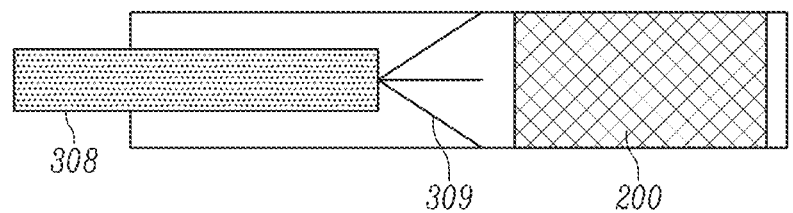
Figure 8H:
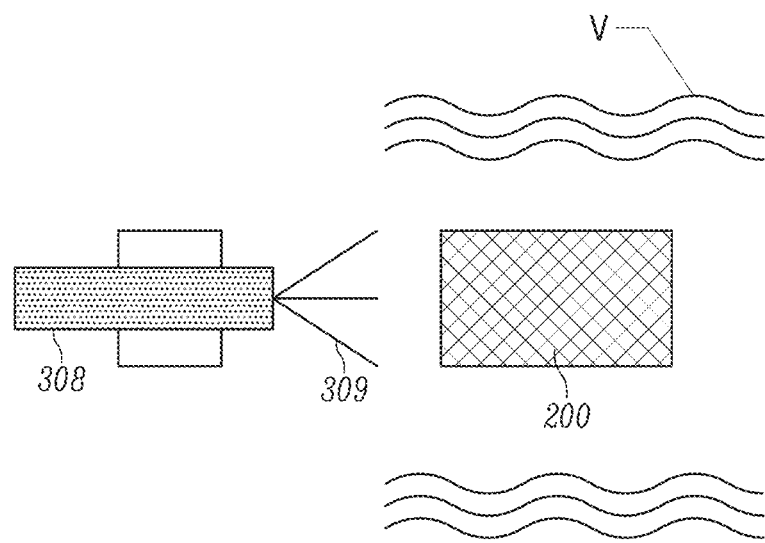

FIGS. 8G and 8H illustrate further deployment and retrieval elements 308. These retrieval devices can have a capture adapter 309 designed to retrieve the absorbent material 200 independent of the structure of the absorbent material 200. Non-limiting embodiments can be hooks, an expandable "claw", and suction.

Note that the deployment and retrieval elements can be in the same housing 102 or from separate devices. In addition, combinations of deployment and retrieval embodiments can be interchanged and/or can be based on the user performing the insertion and removal. For example, if the user is the expectant mother, simplified embodiments of the devices described above and below can be used. If a medical professional is assisting, more complex devices can be deployed. In certain embodiments, the absorbent material can lack a retrieval interface (tether, monofilament plastic line, reattachable interface, etc.) and only a retrieval device can capture and remove the absorbent material.

In further embodiments, the deployment and retrieval elements can have a length L (as illustrated in FIGS. 8D and 8H) and the full length of which can extend outside the vagina. Other embodiments of deployment and retrieval elements can have a full length L that does not extend outside the vagina or vaginal cavity V.

Additionally, the deployment and retrieval elements can be separate elements using the same housing. Thus, the user deploys the absorbent material 200, removes the deployment element from the housing and replaces it with a retrieval element in the same housing. The switch of elements can be performed while the housing is outside or inside the vaginal canal V.

Turning now to the absorbent material 200 it can be in a form of a foam, a solution, liquid, cream, or gel. Alternately or additionally, the absorbent material 200 can be in the form of a gauze, sponge, or tampon like materials. Unlike a tampon, examples of the absorbent material 200 can be designed not to absorb large or significant quantities of fluid. The absorbent material's 200 purpose is to sample small amount/collect the maternal vaginal fluids, and/or the maternal vaginal microbiota. The absorbent material 200 is not designed to stop vaginal discharges.

Absorbency can be measured in units of grams of fluid over grams of material (g/g). As an example, tampons are approximately 7 grams in weight and can absorb between 6 and 18 grams of fluid, depending on their construction (light flow to ultra absorbency), leading to absorbency units of 0.85 to 2.57 g/g of absorbency. Surgical sponges can absorb up to 12.29 g/g. The absorbent material can, in one example, have the absorbency of sterile gauze used for wound dressing. In other embodiment, the absorbent material can have the absorbency less than that of a light flow tampon or can have an absorbency of less than 1.25 g/g or less than 0.85 g/g.

The natural birth of a baby involves the infant passing through the birth canal prior to delivery. Here a large portion of the baby's skin surface is in contact with the birth canal for what may be an extended period of time. In this passing, the infant contacts the maternal vaginal fluids, and/or the maternal vaginal microbiota as noted above. The materials and sampling techniques of this invention attempt to mimic at least partially this "trip".

Thus, collection of the maternal vaginal fluids, and/or the maternal vaginal microbiota may also include a tissue sampling component. The collection the maternal vaginal fluids, and/or the maternal vaginal microbiota can entail the retrieval of a small amount of tissue from the walls of the vagina, this can be as small as just a number of cell sloughed off the vaginal wall.

The structure of the absorbent material 200 can be selected or engineered as such to have a particular pore size that is conducive to collecting small amounts of vaginal fluid, or a surface roughness to facilitate cell collection. The absorbent material 200 can be further designed or selected to be expandable or swell once deployed.

Figure 9A:
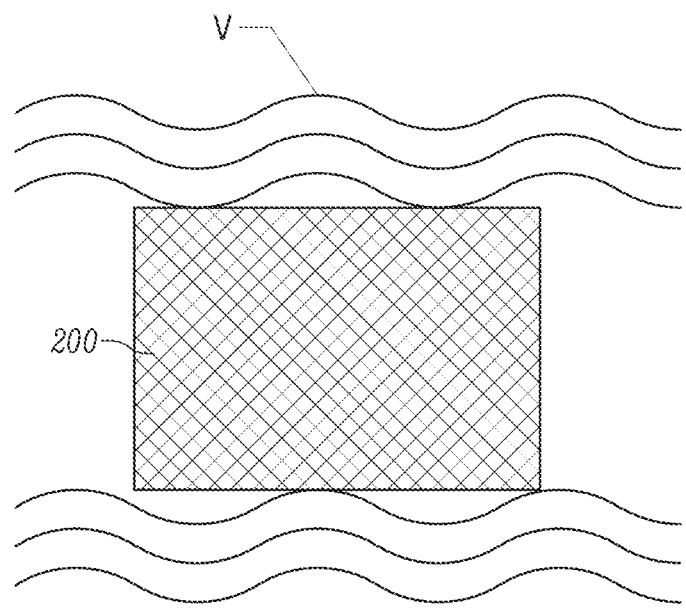
FIGS. 9A-9H. Illustrates multiple examples of the deployment and placement of the absorbent article.

FIGS. 9A-9H illustrate different embodiments of the absorbent material 200. FIG. 9A illustrates absorbent material 200 designed to swell once released from the housing 102. This can be based on the absorption of fluids from the vaginal canal V. The swelling, in certain embodiments, can be enough to fill a portion of the vaginal canal V and have the absorbent material 200 contact the walls of the vaginal canal V.

Figure 9B:
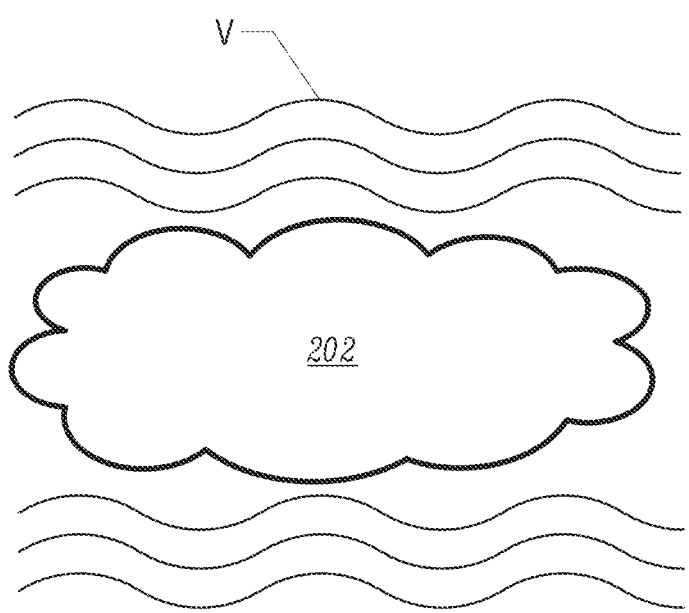
Figure 9C:
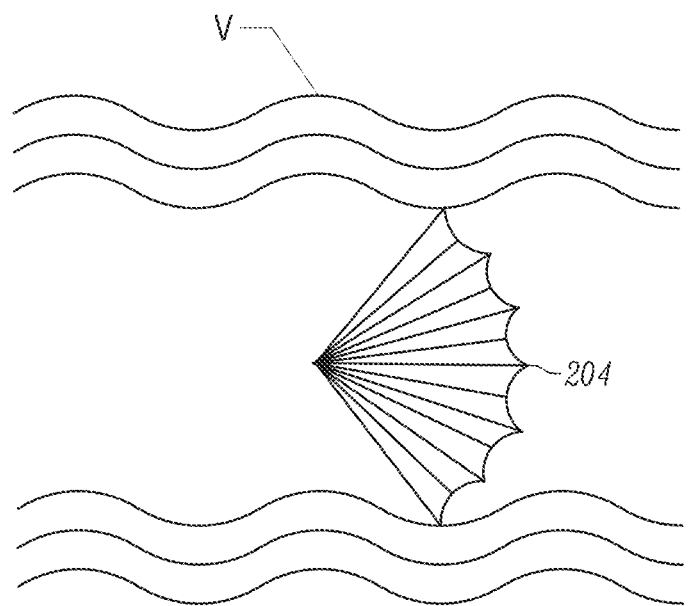

FIG. 9B illustrates the use of a foam or gel 202, which can be designed to swell and even increase its rigidity to allow the whole foam/gel to be retrieved in one collection. In addition, given their nature they can make contact with a large surface area of the birth canal. Materials can also be designed with the same properties, whether structurally or mechanically.

Figure 9D:
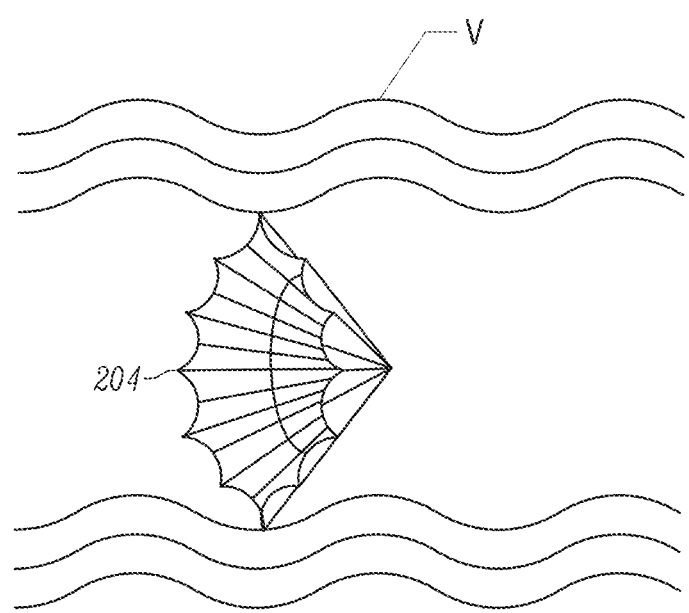

The absorbent material 204 can be a standard material but folded in such a way to one or both of maximize compaction to be as compact as possible in the device 100 prior to vaginal delivery and then to expand or unfold to achieve the maximum surface area contact with the vaginal walls. The absorbent material 204 can be folded or twisted accordingly. Non-limiting examples can be a fan fold (FIG. 9C) and an "umbrella" type fold (FIG. 9D). A "fan fold" is taking the absorbent material 204 and making a first fold a small distance from the edge of the material. The absorbent material 204 is then flipped over and a second fold is made, approximately the same size as the first fold. The material 204 is flipped over again to its original side and a third fold is made, approximately the same size as the first and second folds. This process is repeated until there is no more material to fold. The small distance, in one example, can be an even fraction of the entire length of the material, so as to make each fold of the fan approximately the same size.

Figure 9E:
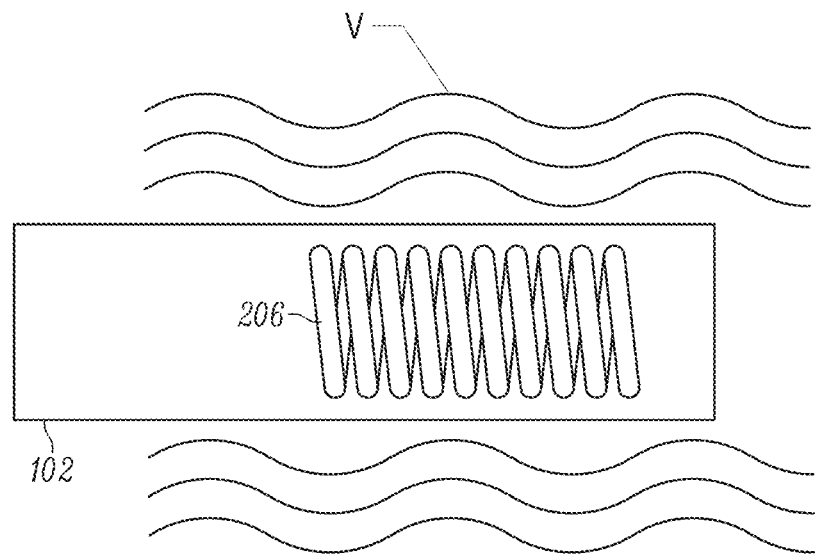
Figure 9F:
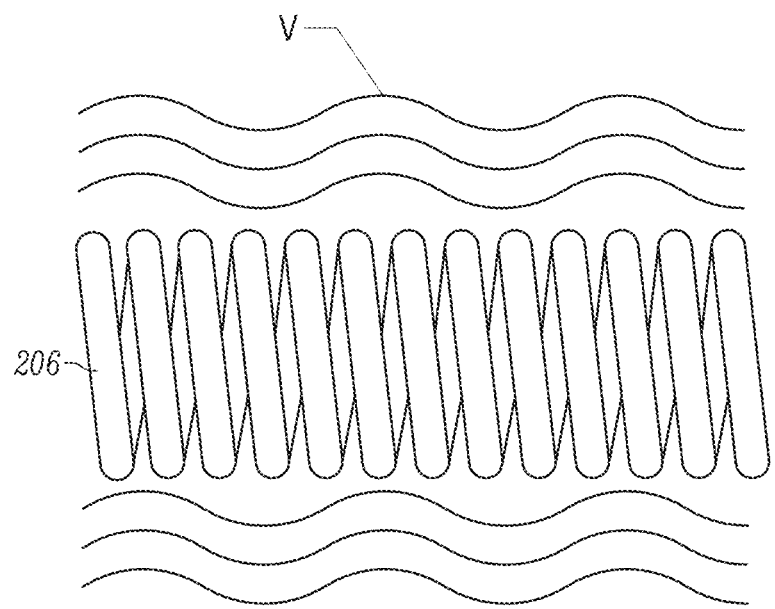
Figure 9G:
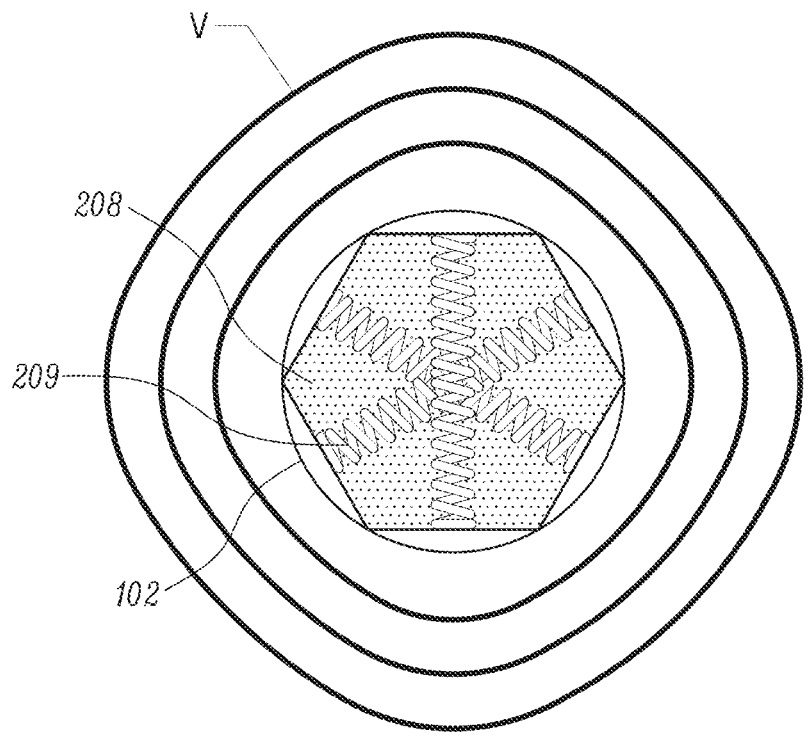
Figure 9H:
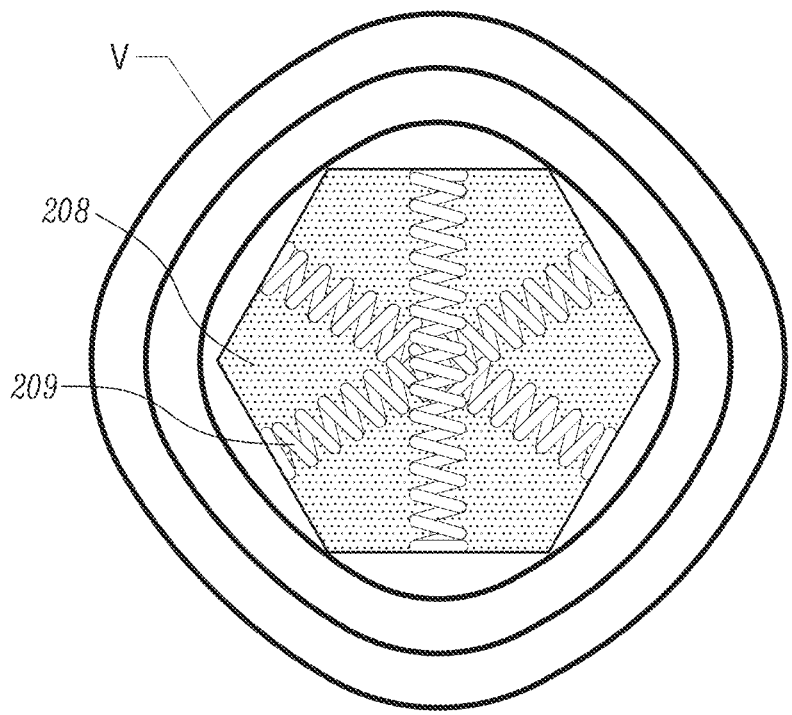

Additionally, the material can be designed to have a "shape memory" where it can be folded to be inserted into the cavity 106, but once deployed, it can take a performed shape. FIGS. 9E and 9F illustrate a shape memory absorbent device 206, first within the housing 102, and compressed into a small profile shape. Next, in FIG. 9F, the shape memory absorbent device 206 can be deployed into the vaginal canal V and expanded to contact the vaginal walls.

A yet another embodiment, the absorbent material 208 allows it to mechanically expand. Like the shape memory absorbent device 206, the mechanically expanding absorbent material 208 has a compact shape in the housing 102 (as seen in longitudinal cross-section, FIG. 9G) and can then expand, using mechanical elements (e.g. a spring) 209, to take its expanded shape (as seen in longitudinal cross-section, FIG. 9H).

The absorbent material 200, 202, 204, 206, 208 can be appropriate natural or synthetic material that functions to capture the vaginal fluids and microbiota. These materials include cotton, sponge, and certain polymers, for example polypropylene/polyglycolic acid (PGA), polypropylene/polylactic acid (PLA), dacron, polyester. In addition, nitinol can be used for shape memory examples, as described above. Further, these materials can be spun, woven, knitted, braded, or manufactured unwoven to provide the necessary surface area for optimal collection. In addition, the absorbent material can be textured if skin cell samples are deemed appropriate for collection as well. However, in at least one example, the material is not designed to absorb enough fluid as to act as a menstrual pad, tampon, or urine pad.

In certain embodiments, the absorbent material 200, 202, 204, 206, 208 can have a retrieval device 305, similar to a tether or anchor (as illustrated in FIG. 8D) that facilitates its retrieval by either a device 100 or a medical professional (e.g., surgeon). The tether 305 can remain internal to the vaginal opening or can extend outside the opening so further insertions into the vagina are not required to retrieve the absorbent material 200, 202, 204, 206, 208.

Retrieval and storage are another aspect of the invention. Embodiments can include non-device retrieval, in which the user (surgeon, expectant mother, or nurse) removes the absorbent material 200, or retrieval can be effected by the same insertion device 100 or a retrieval device. An independent retrieval device can be the same as described above in FIGS. 8C-8H. Once retrieved the absorbent material 200 can be used to swab the infant or can be stored for later use.

Storage, as used herein, can mean relatively soon after retrieval, at a time soon after the delivery of the newborn, and/or at a date in the future. Later or delayed use of the absorbent material 200 leads to examples where the absorbent material 200 can be stored in a container. The sterile container can be a separate container from the deployment/retrieval element 300 or the absorbent material 200 can be drawn back into the device 100, or a second retrieval/storage device. FIG. 1, step 2 illustrates the use of a separate container, which is not used for deployment or retrieval.

As above, storage, for both time and temperature, is dependent on the use. When used "contemporaneously" with the birth of the infant, the adsorbent material is deployed in the mother and removed soon before the c-section. How soon is dependent on the surgical team, but likely within 10 minutes of the start of the procedure. The C-section can take from 10-15 minutes to deliver the infant. After delivery, the infant can be swabbed with the absorbent material. Thus, in an example, "contemporaneous" use can be within an hour of removal of the absorbent material from the vagina. This can be an approximately 1-2 hour window. Longer storage can be contemplated in days, months or years, depending on when the microbiota sample is taken.

A mother may take the sample early if she is aware of circumstances that may cause a change in her natural microbiota before childbirth, but within the pregnancy cycle. A mother may also take a long term or redundant sample for future use with other infants to be born at a future date.

FIGS. 10A to 10E illustrate an example where the absorbent material 200 is retrieved into a deployment/retrieval device 400. This device can be same, or different from, the deployment device described above. The illustrated example uses a tethered version of the absorbent article, but any of the above described retrieval device methods can be used.

Figure 10A:
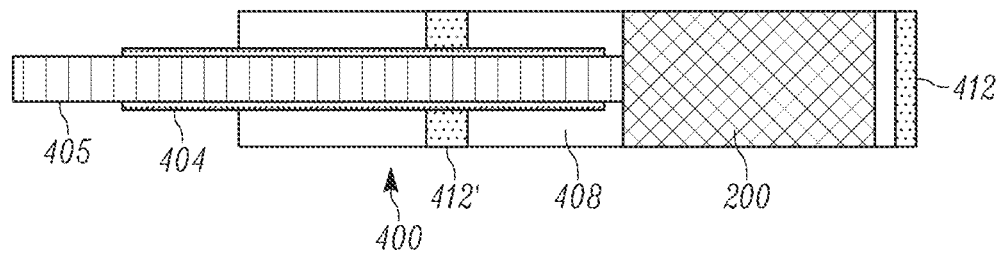
FIGS. 10A-10E. Illustrates an example of a deployment and retrieval of the absorbent material into and removed from the vaginal canal.

FIG. 10A illustrates the loaded deployment/retrieval device 400 having a housing 402 and a deployment/retrieval element 404 tethered to the absorbent material 200. The absorbent material 200 can be any of the embodiments discussed above. A portion of the housing 402 is a sealed cavity 408. The cavity 408 is sealed by sterile seals 412 to maintain the sterility of the absorbent material 200 prior to deployment.

Figure 10B:
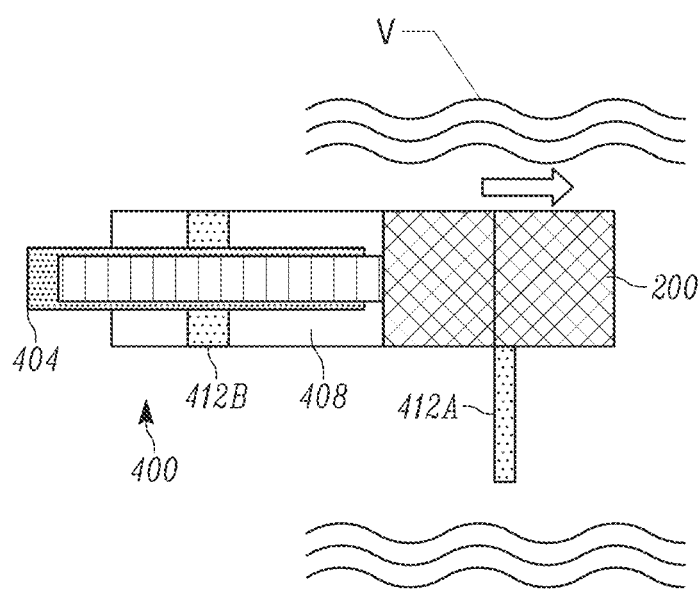
Figure 10C:
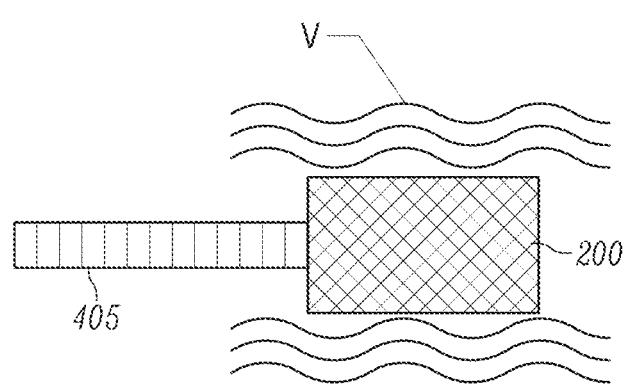

FIGS. 10B and 10C illustrate partial deployment of the absorbent material 200 and its in situ positioning expanded to full size, respectively. In FIG. 10B, at least the front seal 412A is broken as the absorbent material 200 is displaced out of the cavity 408 and in to the vaginal canal V. The rear seals 412B may or may not be compromised when the deployment/retrieval element 404 is displaced to deploy the absorbent material 200. This embodiment illustrates a tether 405 disposed through the deployment/retrieval element 404 so that as the absorbent material 200 is deployed so is the tether 405. However, the tether 405 is designed as such that it extends either a sufficient length down the vaginal canal V or extends outside the vagina to facilitate its use so that its operation can draw back the absorbent material 200 for removal from the vagina. In alternate embodiments, the tether 405 can be coiled inside the cavity 408 and is deployed as the absorbent material 200 is deployed. The proximal end of the tether 405 can be such that it cannot pass through the distal end of the housing 402. In this way, once the housing 402 is removed, the remaining tether is uncoiled and can be extended to its full length. Once the housing 402 clears the vagina the tether can be separated to allow the housing to be removed completely.

As noted above, the absorbent material 200 can remain in the vaginal canal V for a set amount of time, from minutes or hours, to adequately absorb the maternal vaginal microbiota. During the wait time, the deployment/retrieval device 400 can be prepared for removal of the absorbent material 200 or a separate device can be used. Here, the deployment/retrieval element 404 can either be removed, or used to facilitate the "threading" of the tether 405 back into the device 400 through the cavity 408. The cavity 408 itself can be resterilized and/or coated with substances 416 that can maintain/support the maternal vaginal microbiota.

Figure 10D:
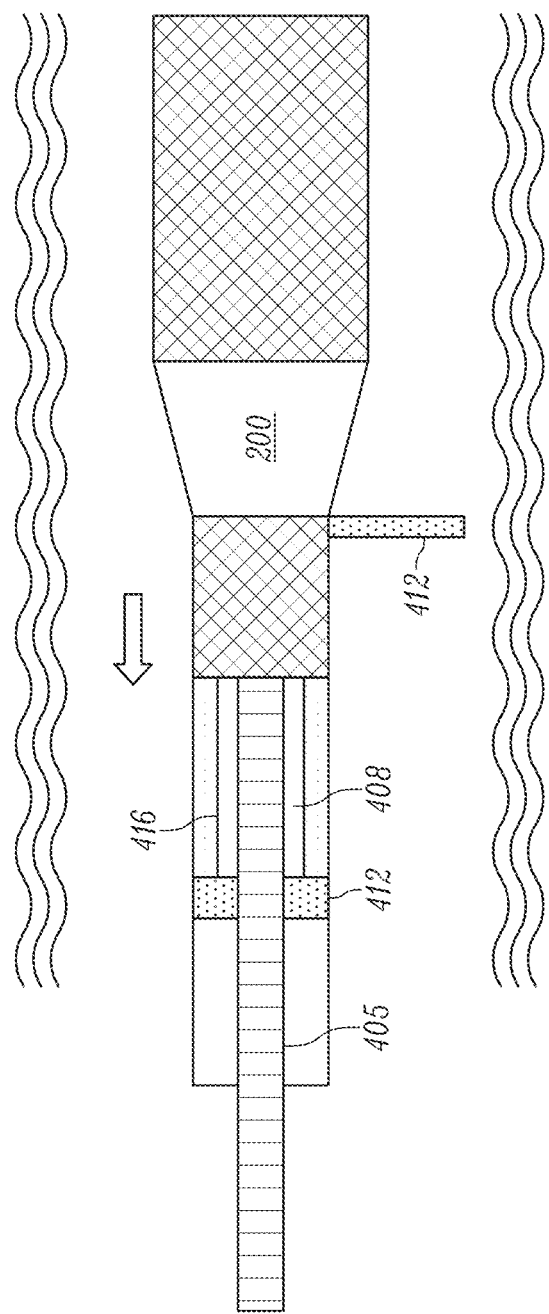
Figure 10E:
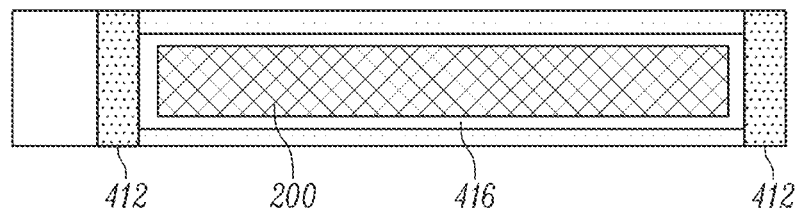

At the appropriate time for removal, the deployment/retrieval device 400 can be reintroduced into the vaginal canal V. The tether 405 can be threaded back through the deployment/retrieval device 400 and the absorbent material 200 can begin to be retrieved into the cavity 408, which is now acting like a sterile container. FIG. 10D illustrates the partial capture of the absorbent material 200 into the cavity 408. FIG. 10E illustrates an embodiment of the final retrieval step in which the absorbent material 200 can be stored in a sealed container, which is, in this embodiment, the cavity 408, until use.

Figure 10F:
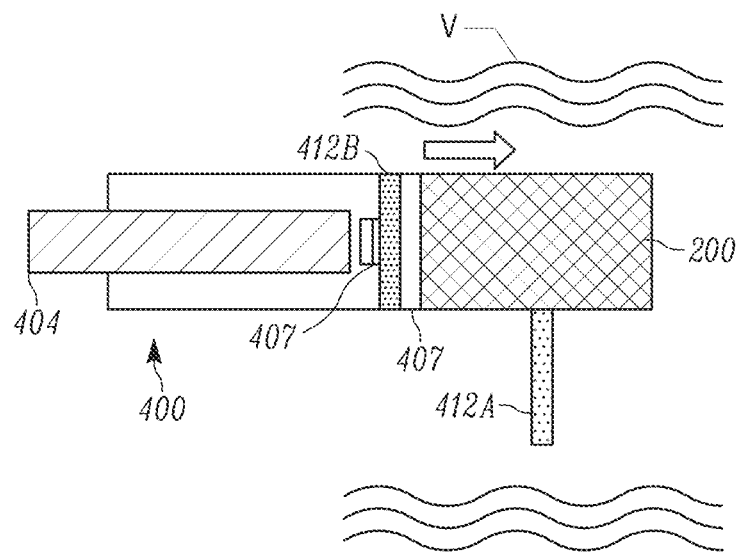
FIGS. 10F-10G. Illustrate a variant example of a deployment and retrieval of the absorbent material into and removed from the vaginal canal.
Figure 10G:
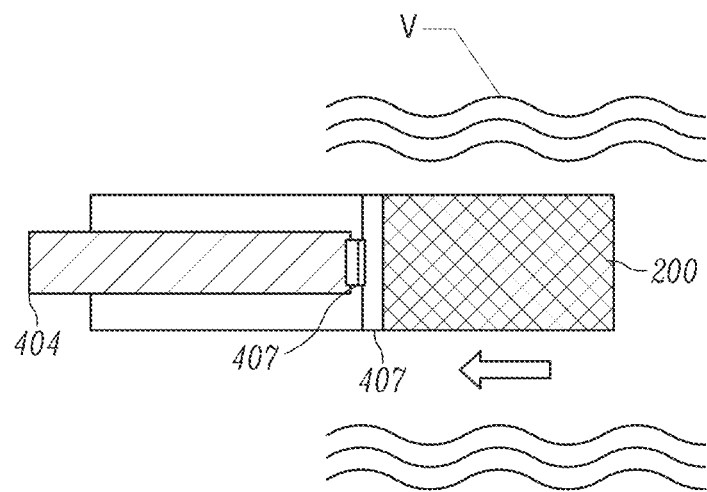

In another embodiment, the absorbent material 200 can be wrapped in sterile packaging and the cavity 408 may not sterile. The seal 412A can be a distal end of the sterile packaging designed to be frangible/tearable/breakable upon pressure from the deployment/retrieval element 404 as it displaces the absorbent material 200 into the vaginal canal V. The absorbent material 200 can have a reattachable interface 407 with matching interface on the deployment/retrieval element 404. The rear seal 412B acts as a barrier between the interfaces 407 during deployment so the absorbent material 200 can be deployed without having to disengage the interfaces. Once the sterile packaging is removed from the housing 102, the reattachable interfaces 407 can now engage when the absorbent material 200 is being retrieved. See, for example, FIGS. 10F and 10G.

The container 400 can, in certain embodiments, just be a sterile vessel. In other embodiments, it can have substances that can maintain/support the maternal vaginal microbiota. The substances can, in certain embodiments, control pH, provided growth media, inhibit "bad" microbiota, and/or stabilize the maternal vaginal microbiota for long term storage, e.g. freeze drying.

A kit can be available with all of the elements necessary to collect, retrieve, dispense to the infant, and store maternal vaginal fluids, and/or the maternal vaginal microbiota This kit can include one or more of the element above, combined together and packaged together for ease of use.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

The invention provides the following Examples in which newborns born by C-section were exposed to a gauze that had been previously introduced in the maternal vagina for one hour prior to the surgical procedure. The gauze was obtained from healthy mothers with acidic, *Lactobacillus* dominant, Group B *Streptococcus*-negative vaginas. Newborns were immediately exposed to the gauze at birth, passing the gauze first through the mouth, then the rest of the face and body. Swabs from oral, skin, and anal regions were taken from the baby and the mother (from whom vaginal swabs were also obtained). Sampling was done at 6 time points during the first month of life, starting at the day of birth. Bacterial DNA was extracted and the V4 region of the 16S rRNA gene was sequenced using an Illumina sequencing instrument. The bacterial microbiota from the multiple body sites was analyzed using QIIME. Details of the materials and study designs, as well as the results, are provided as follows.

Example 1: Transferring Maternal Vaginal Microbiome to Infants Under C-Section Deliveries Materials and Methods Study Design and Enrollment Criteria The study protocol was approved by the Institutional Review Board of the University of Puerto Rico Recinto de Ciencias Medicas and Rio Piedras campus. Mothers were consented during their 3rd trimester control OBGYN control visit. There were three groups of mothers, by delivery and newborn exposure, and they included vaginal, C-section and C-section with exposure to maternal vaginal contents. Inclusion criteria included healthy mothers over 21 years of age, with uncomplicated pregnancies. C-sections were all scheduled, mostly due to previous C-section or maternal choice. For the C-section with exposure to maternal vaginal fluids group, mothers had to have vaginal pH<4 at the time of birth (as measured with a vaginal swab on pH paper). 18 mothers were recruited for this preliminary study, 7 of which gave birth vaginally and 11 by scheduled C-section, of which 4 newborns were exposed at birth to their mother's vaginal contents (Table 2).

TABLE 2

Mode and location of delivery of the 20 mothers of the study

| Family # | Mode of delivery | Birth Location | GBS | Perinatal antibiotics |
|---|---|---|---|---|
| 1 | Vaginal | Home | − | − |
| 15 | Vaginal | Hospital | + | + |
| 16 | Vaginal | Hospital | − | − |
| 19 | Vaginal | Hospital | − | − |
| 20 | Vaginal | Hospital | − | − |
| 21 | Vaginal | Home | − | − |
| 22 | Vaginal | Hospital | − | − |
| 2 | Cesarean | Hospital | − | + |
| 3 | Cesarean | Hospital | − | + |
| 4 | Cesarean | Hospital | − | + |
| 5 | Cesarean | Hospital | − | + |
| 6 | Cesarean | Hospital | − | + |
| 8 | Cesarean | Hospital | − | + |
| 9 | Cesarean | Hospital | − | + |
| 10 | Cesarean | Hospital | + | + |
| 11 | Cesarean | Hospital | + | + |
| 13 | Cesarean + Exposure | Hospital | − | + |
| 14 | Cesarean + Exposure | Hospital | − | + |
| 17 | Cesarean + Exposure | Hospital | − | + |
| 18 | Cesarean + Exposure | Hospital | − | + |

Procedure of Gauze Exposure in C-Section Babies

Figure 3:
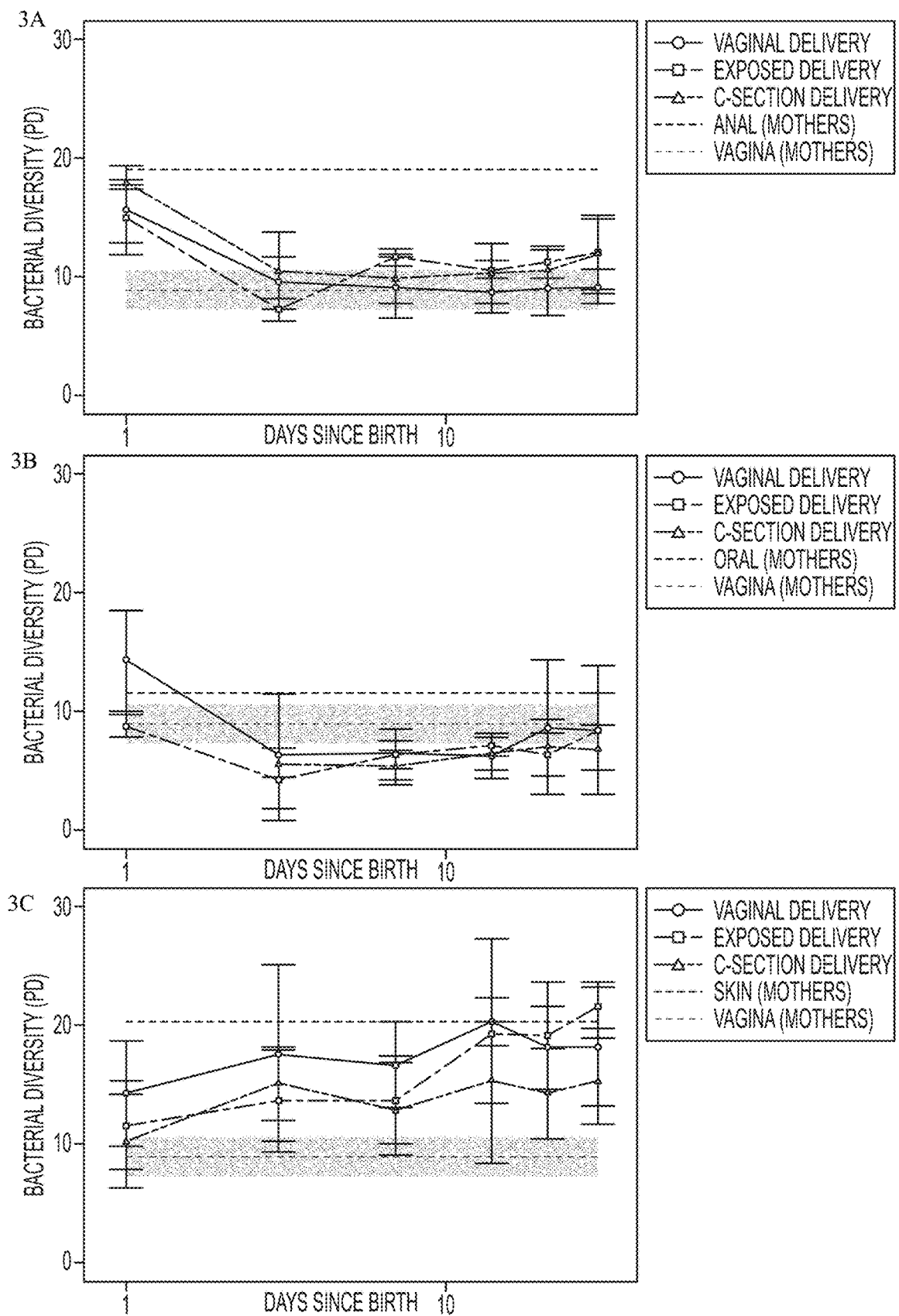
FIGS. 3A-3C. Alpha diversity of baby oral (a), anal (b) and skin (forehead, arm and foot; c) samples, in relation to maternal sites, during the first 30 days of life of the baby. At birth, the bacterial diversity in baby's mouth and anus (but not in the skin) is higher than the maternal vagina diversity (green area), but during the first week, it decreases to values below or similar to vaginal diversity, remaining low during the period of strict lactation (about 3 months).

Mothers were sampled before the C-section prophylactic antibiotics administration. A pair of vaginal swabs were taken, one to measure fluid pH using pH strip paper (Lab Mikro Hydrion™ pH Test Paper, Fisher 13-640-508). By the time the mother is administered the preventive antibiotics (1 g Penicillin-family antibiotics), a medium sterile pad gauze (J&J, 7.6×76 cm) folded like a fan and then in half, was wet with sterile saline solution and introduced in the maternal birth canal in the hour prior to the C-section, at the time antibiotics were administered. The surgeon extracted the gauze right before the procedure, and it was used to swab the infant just after birth (FIG. 3).

Sample Collection

Pre-labeled swabs—in duplicate—were taken from 5 body sites of mother and baby (oral mucosa, forehead, right volar arm, right foot, and anal) plus two additional from the mother (right aureole, vagina; Table 3).

TABLE 3

Number of samples from mothers and infants

| Body site | N swabs | C-section Mother | C-section Infant | Cesarean + Exposure Mother | Cesarean + Exposure Infant | Vaginal Mother | Vaginal Infant | Total |
|---|---|---|---|---|---|---|---|---|
| Vaginal | 78 | 32 | — | 15 | — | 31 | — | 78 |
| Aureole | 98 | 39 | — | 17 | — | 42 | — | 98 |
| skin | 548 | 168 | 104 | 60 | 30 | 93 | 93 | 548 |
| anal | 226 | 33 | 34 | 14 | 50 | 62 | 33 | 226 |
| oral | 185 | 42 | 44 | 15 | 35 | 30 | 19 | 185 |
| Total | 1057 | 282 | 182 | 106 | 115 | 227 | 145 | 1057 |

Samples were collected from the mother before birth, and after birth at each timepoint of the mother-baby pair sampling, namely at ~day 1, 3, 7, and weekly thereafter to the first month (Table 2). Vials were maintained cold and frozen at ultralow temperature (−70 Celsius or below) within the following 2 hours of collection.

At each time point at which samples were collected information survey was applied, and information about mother and baby health, dietary changes and medications was collected. 16S rRNA sequencing and analyses Bacterial DNA was extracted from the 1057 swabs, and the V4 region of the 16S rRNA was amplified and sequenced using Illumina HiSeq as previously described (43). Alpha and beta diversity were estimated using Qiime (33). Linear Discriminant Analysis Effect Size (LEfSe) (44) with default parameters was used to determine taxa that was overrepresented in each baby group in relation to another.

Results

Samples from 18 infants and their mothers (Table 1) were analyzed, including 7 born vaginally and 11 delivered by scheduled cesarean, of which 4 were exposed to the maternal vaginal fluids at birth, using a sterile gauze (Table 1). After transferring the maternal vaginal microbiota to the newborn, the infant microbiota of the exposed group was compared with those from infants born by C-section without exposure, during the first month of life. Briefly, the procedure involved incubating a gauze in the maternal vagina, for the hour preceding the C-section, in mothers that complied with inclusion criteria (scheduled C-section, negative results for GBS, HIV, *Chlamydia*; vaginal pH<4.5 as measured with a vaginal swab sample on a pH paper strip). Within the first few minutes after birth (1-3 min) of these cesarean-delivered infants, the newborns were exposed to their mother's vaginal contents swabbing the newborn body, mouth first, then face and rest of the body (FIG. 1). Of the 14 mothers whose infants were not exposed to the gauze, 3 were GBS positive, 2 delivering by C-section and 1 delivering vaginally. All mothers who underwent Cesarean section received perinatal antibiotics, and the one GBS positive mother who delivered vaginally.

A total of 1072 swabs from multiple body sites were obtained from the 18 babies and mothers, during the first month of life (at 1, 3, 7, 14, 21 and 30 days after the birth). Bacterial communities were characterized by Illumina sequencing of the V4 region of 16S rRNA gene. Samples that had >1,000 sequences (n=1016) were further analyzed. A total of 6,515,724 sequences were obtained (mean 6,(32) 3±4,593, median 5,360 sequences), and assigned to taxa using open reference operational taxonomic unit (OTU) picking using Qiime (33).

Figure 2:
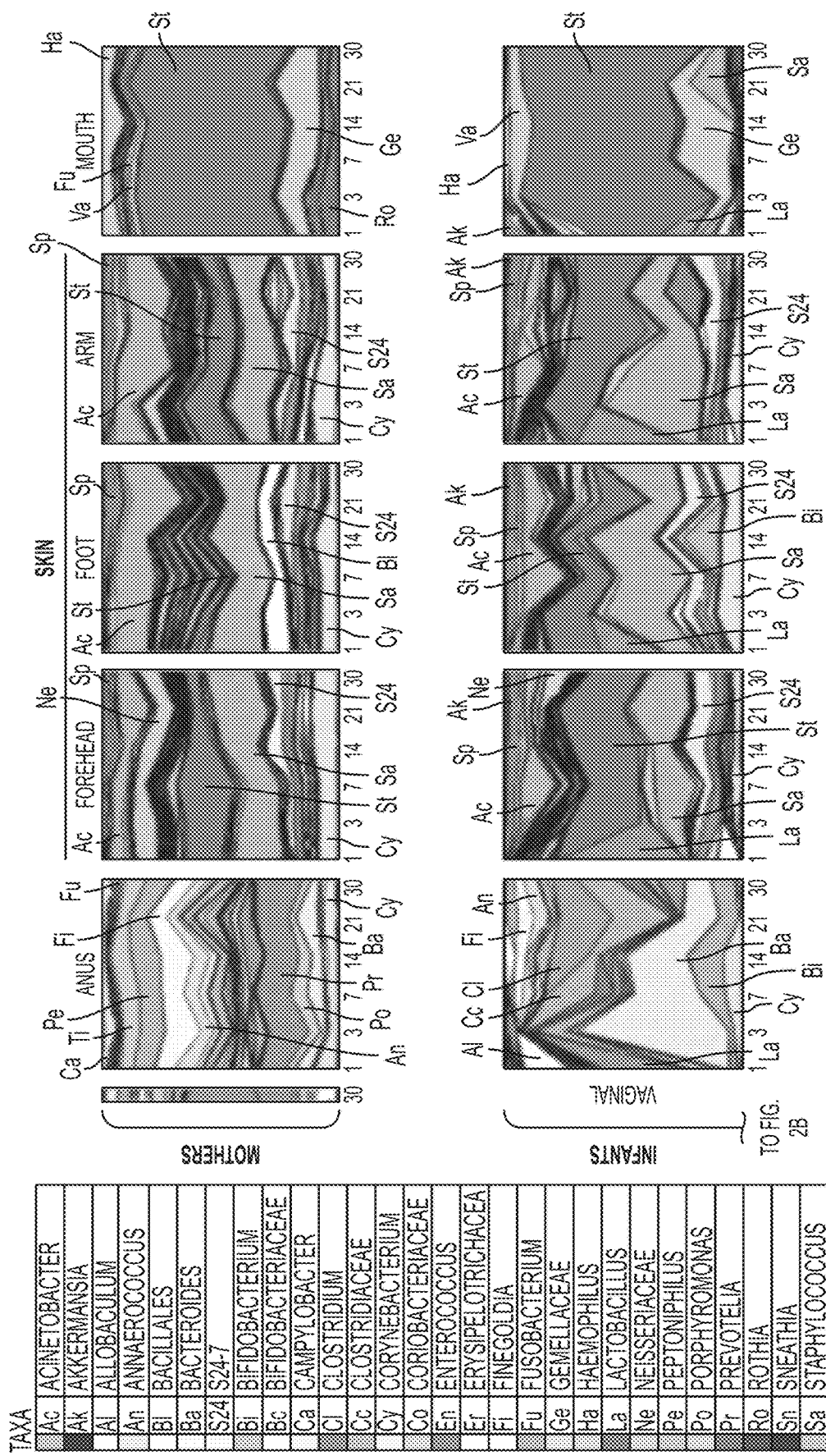
FIG. 2. Mean relative abundance of predominant bacteria (>1% in any sample) in mothers and babies of each delivery group, during the first month of life of the baby. Taxa are reported at the lowest identifiable level.
Figure 2:
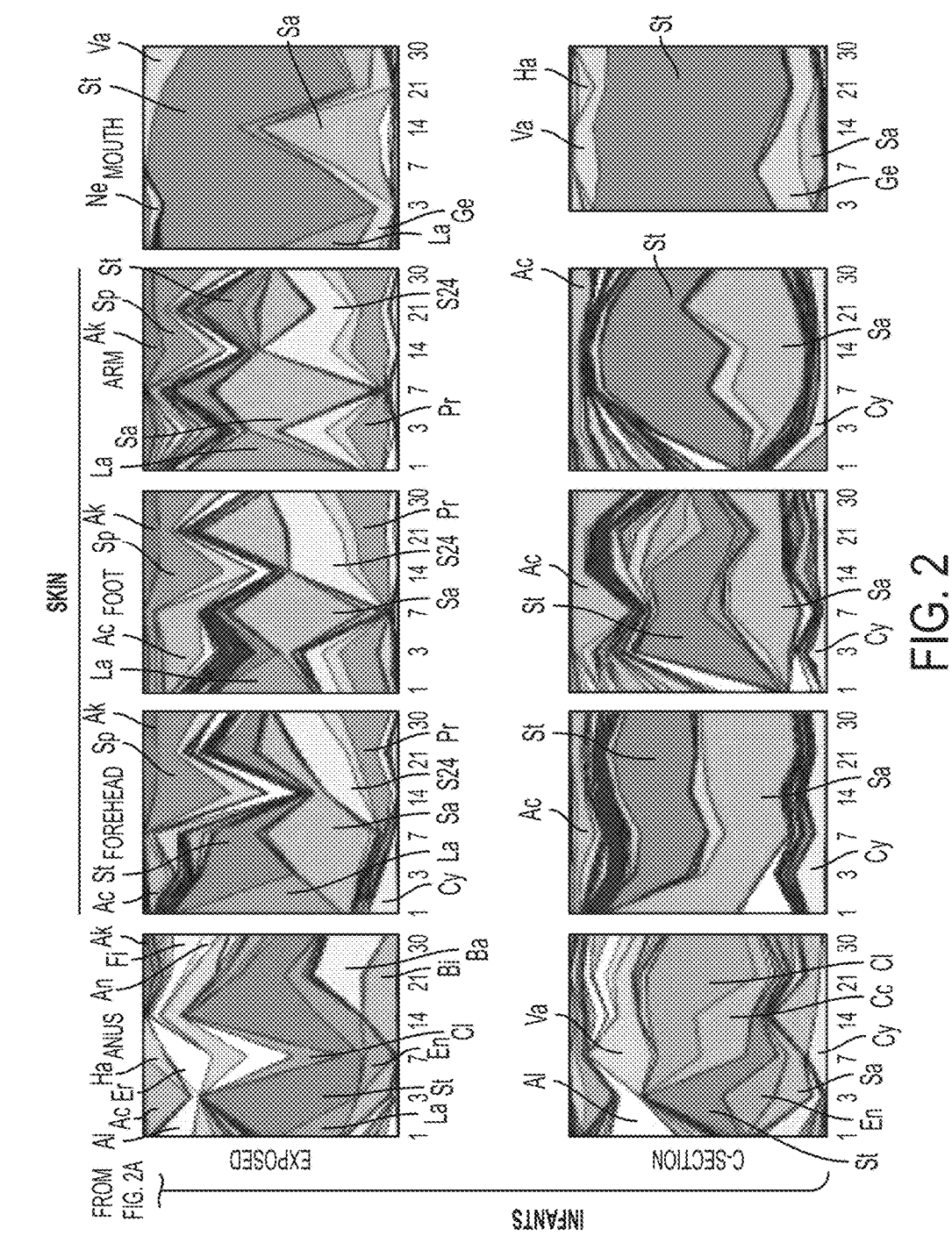
Figure 4:
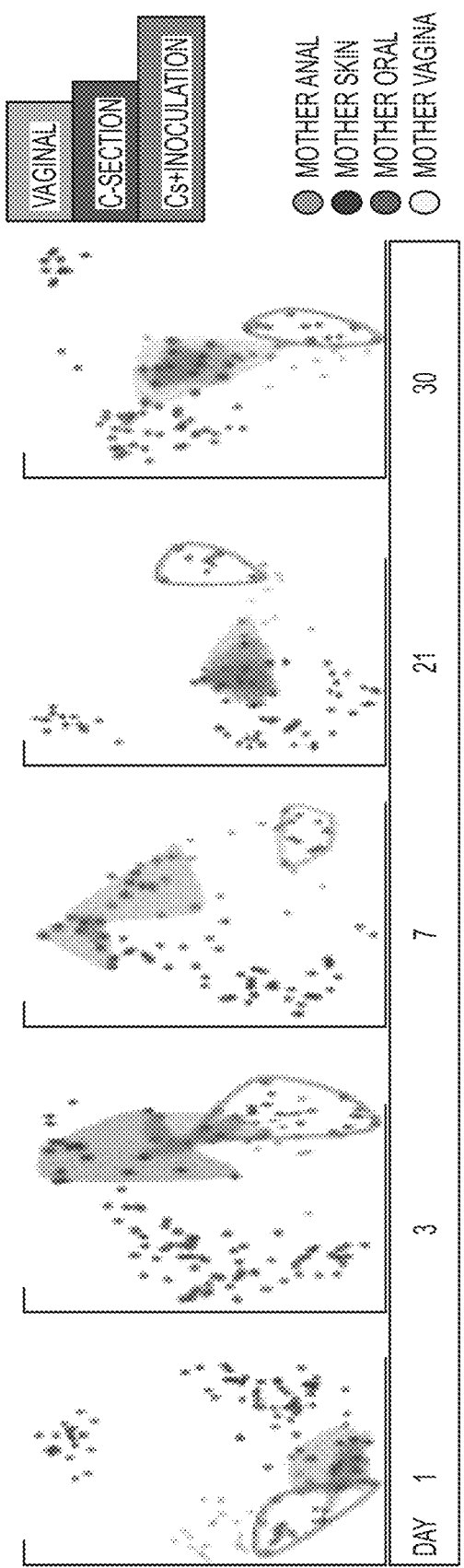
FIG. 4. PCoA of the infant anal and skin microbiota during the first month of life, in relation to maternal sites. The anal microbiota from C-section-inoculated newborns cluster close to that in vaginally delivered babies at day 1. Non inoculated C-section babies cluster separately until the first week of life.
Figure 5:
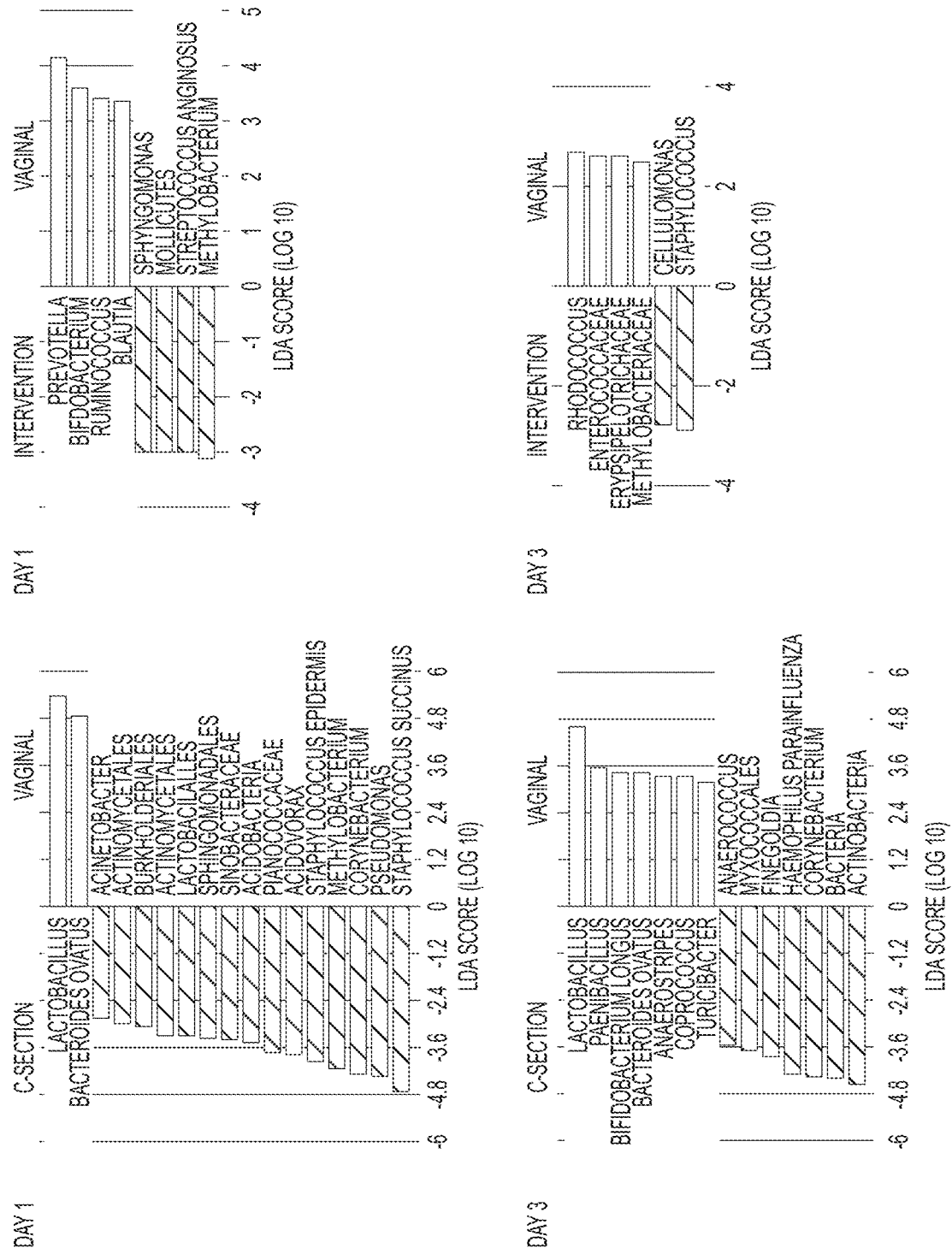
FIG. 5. Lefse analyses depicting overrepresented taxa in the skin forehead of infants by mode of delivery at different times after birth FIG. 6. An example of a device to collect maternal vaginal microbiota.
Figure 5:
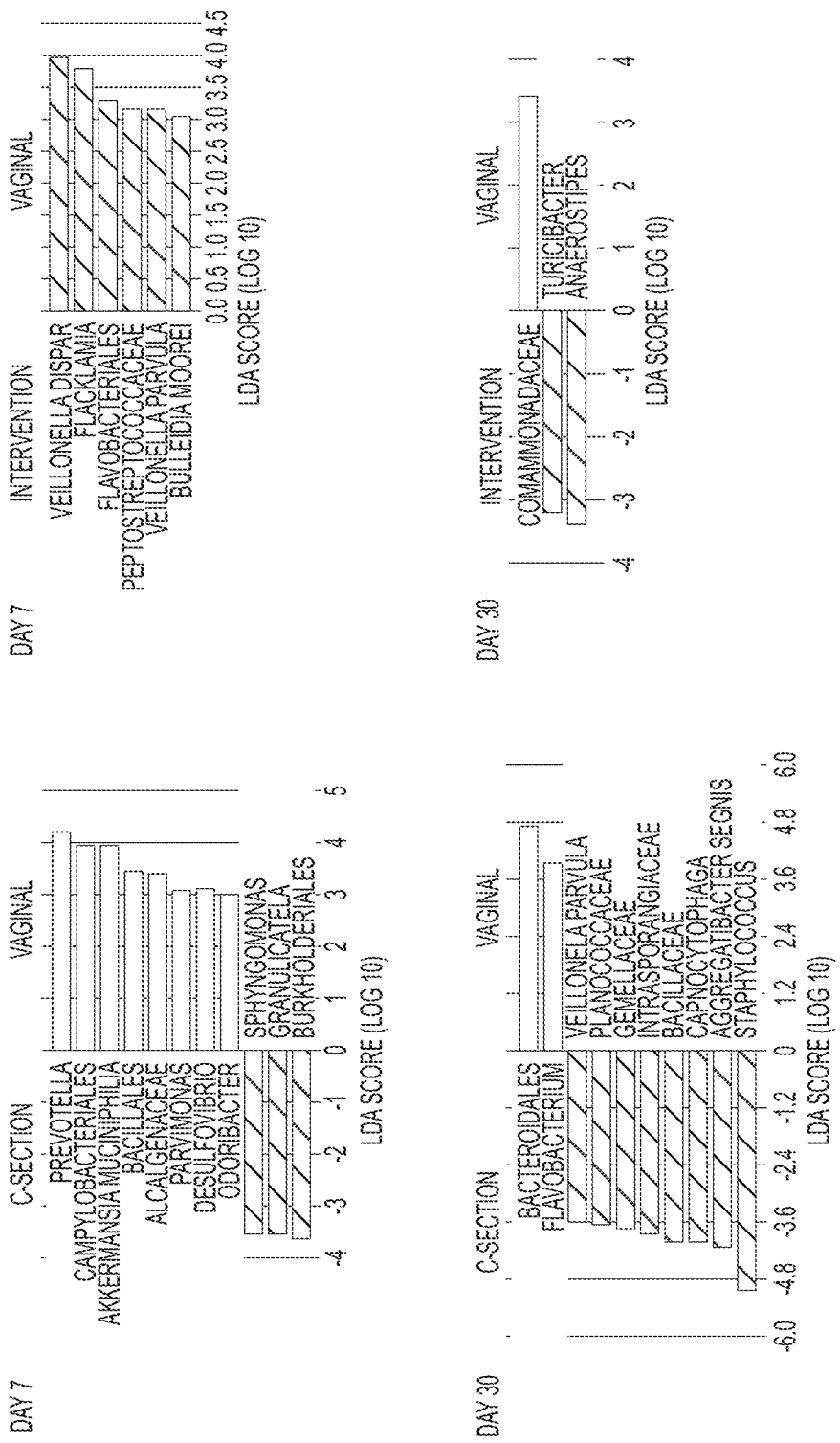

Body site differentiation of colonized sites in newborns occurred in as few as 3 days for skin and mouth, but not for in the whole first month for anal communities (FIG. 2). Regardless of exposure or birth mode, oral and anal—but not skin—sites showed the highest bacterial diversity at birth, and alpha diversity decreased soon after birth (by day 3) in oral and anal sites, and remained relative stable during the first month of life (FIGS. 3 & 4), when communities seem to converge (FIG. 5). Despite convergence in whole community structure, major differences segregate apart the microbiota of infants, by mode of delivery and exposure.

The major bacterial markers of delivery present in vaginally born and not in unexposed Cesarean-delivered infants were i) *Lactobacillus*, present in maternal vagina and in all infant sites at birth, showing a reduction concomitantly with the reduction in site alpha diversity, during the first 3 days after birth (FIGS. 2 & 6); ii) *Bacteroides*, *Clostridium* and *Bifidobacterium* in anal swabs; *Streptococcus* and *Staphylococcus* in skin and mouth; S24-7 and *Stenotrophomonas* in skin and oral *Veillonella* and *Gemellaceae*, which bloomed during the first week of the baby life and remained relatively stable throughout the first month, only in vaginally born infants (FIG. 2). In contrast, unexposed C-section born babies had overrepresented anal *Veillonella* (FIG. 2).

To identify more specifically bacterial species present in vaginally born and not in unexposed Cesarean-delivered infants, DNA was extracted and the V4 region of 16S rRNA gene was sequenced in Illumina. Sequences were assigned to taxa using BLASTN (web-based blastn site, NCBI) using OTU picking algorithm, 97% identity to the Greengenes database (v13_8), in QIIME (Caporaso et al., 2010, Nat. Methods, 7(5): 335-336). To further confirm taxonomies, the 16S rRNA sequences of each OTU were used in BLASTN (web-based blastn suite, NCBI) using 97% identity to the Genbank 16S rRNA sequence database (May 2016). The results are shown in Table 4.

TABLE 4

Species-Level Ideintification of Bacteria Differentially Observed in Infants by Exposure at Birth

| Taxonomic info | Genus species | BLASTN Identity (%) |
|---|---|---|
| p__Proteobacteria; c__Gammaproteobacteria; o__Pseudomonadales; f__Moraxellaceae; g__Acinetobacter; s__ | *Acinetobacter baumannii* | 100 |
| p__Proteobacteria; c__Gammaproteobacteria; o__Pseudomonadales; f__Moraxellaceae; g__Acinetobacter; s__ | *Acinetobacter gerneri* | 100 |
| p__Proteobacteria; c__Gammaproteobacteria; o__Pseudomonadales; f__Moraxellaceae; g__Acinetobacter; s__johnsonii | *Acinetobacter johnsonii* | 98.42 |
| p__Proteobacteria; c__Gammaproteobacteria; o__Pseudomonadales; f__Moraxellaceae; g__Acinetobacter; s__ | *Acinetobacter radioresistens* | 99.6 |
| p__Proteobacteria; c__Gammaproteobacteria; o__Pseudomonadales; f__Moraxellaceae; g__Acinetobacter; s__ | *Acinetobacter schindleri* | 98.42 |
| p__Proteobacteria; c__Gammaproteobacteria; o__Pseudomonadales; f__Moraxellaceae; g__Acinetobacter; s__rhizosphaerae | *Acinetobacter seifertii* | 99.6 |
| p__Proteobacteria; c__Gammaproteobacteria; o__Pseudomonadales; f__Moraxellaceae; g__Acinetobacter; s__ | *Acinetobacter variabilis* | 100 |
| p__Actinobacteria; c__Actinobacteria; o__Actinomycetales; f__Actinomycetaceae; g__Actinomyces; s__europaeus | *Actinomyces europaeus* | 100 |
| p__Actinobacteria; c__Actinobacteria; o__Actinomycetales; f__Actinomycetaceae; g__Actinomyces; s__ | *Actinomyces neuii* | 100 |
| p__Firmicutes; c__Bacilli; o__Lactobacillales; f__Aerococcaceae; g__Aerococcus; s__ | *Aerococcus christensenii* | 99.21 |
| p__Actinobacteria; c__Actinobacteria; o__Bifidobacteriales; f__Bifidobacteriaceae; g__; s__ | *Alloscardovia omnicolens* | 100 |
| p__Firmicutes; c__Clostridia; o__Clostridiales; f__[Tissierellaceae]; g__Anaerococcus; s__ | *Anaerococcus lactolyticus* | 100 |
| p__Firmicutes; c__Clostridia; o__Clostridiales; f__[Tissierellaceae]; g__Anaerococcus; s__ | *Anaerococcus murdochii* | 100 |
| p__Firmicutes; c__Clostridia; o__Clostridiales; f__[Tissierellaceae]; g__Anaerococcus; s__ | *Anaerococcus obesiensis* | 100 |
| p__Firmicutes; c__Clostridia; o__Clostridiales; f__[Tissierellaceae]; g__Anaerococcus; s__ | *Anaerococcus octavius* | 100 |
| p__Firmicutes; c__Clostridia; o__Clostridiales; f__[Tissierellaceae]; g__Anaerococcus; s__ | *Anaerococcus prevotii* | 100 |
| p__Firmicutes; c__Clostridia; o__Clostridiales; f__[Tissierellaceae]; g__Anaerococcus; s__ | *Anaerococcus provenciensis* | 100 |
| p__Firmicutes; c__Clostridia; o__Clostridiales; f__[Tissierellaceae]; g__Anaerococcus; s__ | *Anaerococcus vaginalis* | 100 |
| p__Firmicutes; c__Clostridia; o__Clostridiales; f__Lachnospiraceae; g__; s__ | *Anaerostipes hadrus* | 99.21 |
| p__Firmicutes; c__Bacilli; o__Bacillales; f__Bacillaceae; g__Anoxybacillus; s__kestanbolensis | *Anoxybacillus flavithermus* | 100 |
| p__Proteobacteria; c__Alphaproteobacteria; o__Caulobacterales; f__Caulobacteraceae; g__Asticcacaulis; s__ | *Asticcacaulis excentricus* | 97.23 |
| p__Actinobacteria; c__Coriobacteriia; o__Coriobacteriales; f__Coriobacteriaceae; g__Atopobium; s__ | *Atopobium deltae* | 99.61 |
| p__Actinobacteria; c__Coriobacteriia; o__Coriobacteriales; f__Coriobacteriaceae; g__; s__ | *Atopobium vaginae* | 100 |
| p__Firmicutes; c__Bacilli; o__Bacillales; f__Bacillaceae; g__Bacillus; s__ | *Bacillus vireti* | 100 |
| p__Bacteroidetes; c__Bacteroidia; o__Bacteroidales; f__Bacteroidaceae; g__Bacteroides; s__ | *Bacteroides finegoldii* | 98.42 |
| p__Bacteroidetes; c__Bacteroidia; o__Bacteroidales; f__Bacteroidaceae; g__Bacteroides; s__ | *Bacteroides vulgatus* | 100 |
| p__Actinobacteria; c__Actinobacteria; o__Bifidobacteriales; f__Bifidobacteriaceae; g__Bifidobacterium; s__ | *Bifidobacterium breve* | 100 |
| p__Actinobacteria; c__Actinobacteria; o__Bifidobacteriales; f__Bifidobacteriaceae; g__Bifidobacterium; s__ | *Bifidobacterium pseudolongum* | 98.81 |
| p__Proteobacteria; c__Alphaproteobacteria; o__Sphingomonadales; f__Sphingomonadaceae; g__; s__natatoria | *Blastomonas natatoria* | 100 |
| p__Proteobacteria; c__Alphaproteobacteria; o__Rhizobiales; f__Bradyrhizobiaceae; g__; s__ | *Bradyrhizobium lupini* | 100 |
| p__Actinobacteria; c__Actinobacteria; | *Brevibacterium* | 99.21 |

TABLE 4-continued

Species-Level Ideintification of Bacteria Differentially
Observed in Infants by Exposure at Birth

| Taxonomic info | Genus species | BLASTN Identity (%) |
|---|---|---|
| o_Actinomycetales; f_Brevibacteriaceae; g_Brevibacterium; s_paucivorans | *paucivorans* | |
| p_Proteobacteria; c_Epsilonproteobacteria; o_Campylobacterales; f_Campylobacteraceae; g_Campylobacter; s_ | *Campylobacter coli* | 100 |
| p_Proteobacteria; c_Epsilonproteobacteria; o_Campylobacterales; f_Campylobacteraceae; g_Campylobacter; s_ | *Campylobacter hominis* | 100 |
| p_Proteobacteria; c_Epsilonproteobacteria; o_Campylobacterales; f_Campylobacteraceae; g_Campylobacter; s_ | *Campylobacter ureolyticus* | 100 |
| p_Actinobacteria; c_Actinobacteria; o_Actinomycetales; f_Microbacteriaceae | *Clavibacter michiganensis* | 98.42 |
| p_Bacteroidetes; c_Flavobacteriia; o_Flavobacteriales; f_[Weeksellaceae]; g_Cloacibacterium; s_ | *Cloacibacterium rupense* | 99.21 |
| p_Firmicutes; c_Clostridia; o_Clostridiales; f_Lachnospiraceae; g_; s_ | *Clostridium clostridioforme* | 100 |
| p_Firmicutes; c_Clostridia; o_Clostridiales; f_Clostridiaceae; g_Clostridium; s_perfringens | *Clostridium perfringens* | N/A |
| p_Proteobacteria; c_Betaproteobacteria; o_Burkholderiales; f_Comamonadaceae; g_; s_ | *Comamonas serinivorans* | 99.21 |
| p_Proteobacteria; c_Betaproteobacteria; o_Burkholderiales; f_Comamonadaceae; g_Comamonas; s_ | *Comamonas testosteroni* | 100 |
| p_Actinobacteria; c_Actinobacteria; o_Actinomycetales; f_Corynebacteriaceae; g_Corynebacterium; s_ | *Corynebacterium amycolatum* | 98.43 |
| p_Actinobacteria; c_Actinobacteria; o_Actinomycetales; f_Corynebacteriaceae; g_Corynebacterium; s_ | *Corynebacterium appendicis* | 100 |
| p_Actinobacteria; c_Actinobacteria; o_Actinomycetales; f_Corynebacteriaceae; g_Corynebacterium; s_ | *Corynebacterium argentoratense* | 99.21 |
| p_Actinobacteria; c_Actinobacteria; o_Actinomycetales; f_Corynebacteriaceae; g_Corynebacterium; s_ | *Corynebacterium aurimucosum* | 100 |
| p_Actinobacteria; c_Actinobacteria; o_Actinomycetales; f_Corynebacteriaceae; g_Corynebacterium; s_ | *Corynebacterium canis* | 99.61 |
| p_Actinobacteria; c_Actinobacteria; o_Actinomycetales; f_Corynebacteriaceae; g_Corynebacterium; s_ | *Corynebacterium casei* | 97.24 |
| p_Actinobacteria; c_Actinobacteria; o_Actinomycetales; f_Corynebacteriaceae; g_Corynebacterium; s_ | *Corynebacterium coyleae* | 100 |
| p_Actinobacteria; c_Actinobacteria; o_Actinomycetales; f_Corynebacteriaceae; g_Corynebacterium; s_ | *Corynebacterium freneyi* | 100 |
| p_Actinobacteria; c_Actinobacteria; o_Actinomycetales; f_Corynebacteriaceae; g_Corynebacterium; s_ | *Corynebacterium imitans* | 98.82 |
| p_Actinobacteria; c_Actinobacteria; o_Actinomycetales; f_Corynebacteriaceae; g_Corynebacterium; s_ | *Corynebacterium jeikeium* | 100 |
| p_Actinobacteria; c_Actinobacteria; o_Actinomycetales; f_Corynebacteriaceae; g_Corynebacterium; s_kroppenstedtii | *Corynebacterium kroppenstedtii* | 100 |
| p_Actinobacteria; c_Actinobacteria; o_Actinomycetales; f_Corynebacteriaceae; g_Corynebacterium; s_ | *Corynebacterium lactis* | 100 |
| p_Actinobacteria; c_Actinobacteria; o_Actinomycetales; f_Corynebacteriaceae; g_Corynebacterium; s_ | *Corynebacterium matruchotii* | 99.21 |
| p_Actinobacteria; c_Actinobacteria; o_Actinomycetales; f_Corynebacteriaceae; g_Corynebacterium; s_ | *Corynebacterium mycetoides* | 98.31 |
| p_Actinobacteria; c_Actinobacteria; o_Actinomycetales; f_Corynebacteriaceae; g_Corynebacterium; s_ | *Corynebacterium mycetoides* | 99.61 |
| p_Actinobacteria; c_Actinobacteria; o_Actinomycetales; f_Corynebacteriaceae; g_Corynebacterium; s_ | *Corynebacterium pilbarense* | 100 |
| p_Actinobacteria; c_Actinobacteria; | *Corynebacterium* | 100 |

TABLE 4-continued

Species-Level Ideintification of Bacteria Differentially
Observed in Infants by Exposure at Birth

| Taxonomic info | Genus species | BLASTN Identity (%) |
|---|---|---|
| o__Actinomycetales; f__Corynebacteriaceae; g__Corynebacterium; s__ | *pyruviciproducens* | |
| p__Actinobacteria; c__Actinobacteria; o__Actinomycetales; f__Corynebacteriaceae; g__Corynebacterium; s__ | *Corynebacterium spheniscorum* | 100 |
| p__Actinobacteria; c__Actinobacteria; o__Actinomycetales; f__Corynebacteriaceae; g__Corynebacterium; s__ | *Corynebacterium striatum* | 100 |
| p__Actinobacteria; c__Actinobacteria; o__Actinomycetales; f__Corynebacteriaceae; g__Corynebacterium; s__ | *Corynebacterium terpenotabidum* | 99.21 |
| p__Actinobacteria; c__Actinobacteria; o__Actinomycetales; f__Corynebacteriaceae; g__Corynebacterium; s__ | *Corynebacterium thomssenii* | 100 |
| p__Actinobacteria; c__Actinobacteria; o__Actinomycetales; f__Corynebacteriaceae; g__Corynebacterium; s__ | *Corynebacterium tuberculostearicum* | 100 |
| p__Actinobacteria; c__Actinobacteria; o__Actinomycetales; f__Corynebacteriaceae; g__Corynebacterium; s__ | *Corynebacterium tuscaniense* | 99.61 |
| p__Actinobacteria; c__Actinobacteria; o__Actinomycetales; f__Dermabacteraceae; g__Dermabacter; s__ | *Dermabacter hominis* | 99.6 |
| p__Actinobacteria; c__Actinobacteria; o__Actinomycetales; f__Dermabacteraceae | *Devriesea agamarum* | 97.63 |
| p__Firmicutes; c__Clostridia; o__Clostridiales; f__Veillonellaceae; g__Dialister; s__ | *Dialister micraerophilus* | 100 |
| p__Firmicutes; c__Clostridia; o__Clostridiales; f__Veillonellaceae; g__Dialister; s__ | *Dialister propionicifaciens* | 100 |
| p__Firmicutes; c__Clostridia; o__Clostridiales; f__Veillonellaceae; g__Dialister; s__ | *Dialister succinatiphilus* | 97.62 |
| p__Firmicutes; c__Clostridia; o__Clostridiales; f__Lachnospiraceae; g__[Ruminococcus]; s__gnavus | *Dorea longicatena* | 99.61 |
| p__Firmicutes; c__Bacilli; o__Lactobacillales; f__Enterococcaceae; g__Enterococcus; s__ | *Enterococcus hirae* | 100 |
| p__Firmicutes; c__Bacilli; o__Lactobacillales; f__Aerococcaceae; g__Facklamia; s__ | *Eremococcus coleocola* | 100 |
| p__Firmicutes; c__Erysipelotrichi; o__Erysipelotrichales; f__Erysipelotrichaceae; g__; s__ | *Erysipelatoclostridium ramosum* | 100 |
| p__Proteobacteria; c__Gammaproteobacteria; o__Enterobacteriales; f__Enterobacteriaceae; g__; s__ | *Escherichia marmotae* | 100 |
| p__Firmicutes; c__Clostridia; o__Clostridiales; f__[Tissierellaceae]; g__1-68; s__ | *Ezakiella peruensis* | 100 |
| p__Firmicutes; c__Bacilli; o__Lactobacillales; f__Aerococcaceae; g__Facklamia; s__ | *Facklamia hominis* | 99.21 |
| p__Firmicutes; c__Bacilli; o__Lactobacillales; f__Aerococcaceae; g__Facklamia; s__ | *Facklamia ignava* | 100 |
| p__Firmicutes; c__Clostridia; o__Clostridiales; f__Clostridiaceae; g__Clostridium; s__ | *Fastidiosipila sanguinis* | 99.21 |
| p__Firmicutes; c__Clostridia; o__Clostridiales; f__[Tissierellaceae]; g__WAL_1855D; s__ | *Fenollaria massiliensis* | 100 |
| p__Firmicutes; c__Clostridia; o__Clostridiales; f__[Tissierellaceae]; g__Finegoldia; s__ | *Finegoldia magna* | 100 |
| p__Fusobacteria; c__Fusobacteriia; o__Fusobacteriales; f__Fusobacteriaceae; g__Fusobacterium; s__ | *Fusobacterium equinum* | 100 |
| p__Fusobacteria; c__Fusobacteriia; o__Fusobacteriales; f__Fusobacteriaceae; g__Fusobacterium; s__ | *Fusobacterium nucleatum* | 100 |
| p__Fusobacteria; c__Fusobacteriia; o__Fusobacteriales; f__Fusobacteriaceae; g__Fusobacterium; s__ | *Fusobacterium periodonticum* | 97.22 |
| p__Fusobacteria; c__Fusobacteriia; o__Fusobacteriales; f__Fusobacteriaceae; g__Fusobacterium; s__ | *Fusobacterium simiae* | 100 |
| p__Actinobacteria; c__Actinobacteria; o__Bifidobacteriales; f__Bifidobacteriaceae | *Gardnerella vaginalis* | 100 |
| p__Firmicutes; c__Bacilli; o__Gemellales; f__Gemellaceae; g__Gemella; s__ | *Gemella asaccharolytica* | 99.6 |
| p__Firmicutes; c__Bacilli; o__Gemellales; f__Gemellaceae; g__; s__ | *Gemella taiwanensis* | 100 |
| p__Proteobacteria; c__Gammaproteobacteria; o__Pasteurellales; f__Pasteurellaceae; g__Aggregatibacter; s__ | *Haemophilus pittmaniae* | 100 |

TABLE 4-continued

Species-Level Ideintification of Bacteria Differentially
Observed in Infants by Exposure at Birth

| Taxonomic info | Genus species | BLASTN Identity (%) |
|---|---|---|
| p__Firmicutes; c__Clostridia; o__Clostridiales; f__[Tissierellaceae]; g__Helcococcus; s__ | Helcococcus sueciensis | 100 |
| p__Proteobacteria; c__Betaproteobacteria; o__Burkholderiales; f__Oxalobacteraceae | Herbaspirillum chlorophenolicum | 100 |
| p__Synergistetes; c__Synergistia; o__Synergistales; f__Dethiosulfovibrionaceae; g__Jonquetella; s__anthropi | Jonquetella anthropi | 100 |
| p__Actinobacteria; c__Actinobacteria; o__Actinomycetales; f__Micrococcaceae; g__Microbispora; s__rosea | Kocuria flava strain HO-9041 | 98.42 |
| p__Actinobacteria; c__Actinobacteria; o__Actinomycetales; f__Micrococcaceae; g__; s__ | Kocuria kristinae strain DSM 20032 | 100 |
| p__Actinobacteria; c__Actinobacteria; o__Actinomycetales; f__Intrasporangiaceae | Kytococcus schroeteri strain Muenster 2000 | 99.53 |
| p__Firmicutes; c__Bacilli; o__Lactobacillales; f__Lactobacillaceae; g__Lactobacillus; s__ | Lactobacillus coleohominis | 100 |
| p__Firmicutes; c__Bacilli; o__Lactobacillales; f__Lactobacillaceae; g__Lactobacillus; s__ | Lactobacillus crispatus | 100 |
| p__Firmicutes; c__Bacilli; o__Lactobacillales; f__Lactobacillaceae; g__Lactobacillus; s__ | Lactobacillus hominis | 100 |
| p__Firmicutes; c__Bacilli; o__Lactobacillales; f__Lactobacillaceae; g__Lactobacillus; s__iners | Lactobacillus iners | 100 |
| p__Firmicutes; c__Bacilli; o__Lactobacillales; f__Lactobacillaceae; g__Lactobacillus; s__ | Lactobacillus intestinalis | 100 |
| p__Firmicutes; c__Bacilli; o__Lactobacillales; f__Lactobacillaceae; g__Lactobacillus; s__ | Lactobacillus jensenii | 100 |
| p__Firmicutes; c__Bacilli; o__Lactobacillales; f__Lactobacillaceae; g__Lactobacillus; s__ | Lactobacillus psittaci | 98.81 |
| p__Firmicutes; c__Bacilli; o__Lactobacillales; f__Lactobacillaceae; g__Lactobacillus; s__ | Lactobacillus reuteri | 99.6 |
| p__Firmicutes; c__Bacilli; o__Lactobacillales; f__Lactobacillaceae; g__Lactobacillus; s__ | Lactobacillus rodentium | 97.23 |
| p__Firmicutes; c__Bacilli; o__Lactobacillales; f__Streptococcaceae; g__Lactococcus; s__ | Lactococcus lactis | 99.6 |
| p__Firmicutes; c__Clostridia; o__Clostridiales; f__[Tissierellaceae]; g__ph2; s__ | Levyella massiliensis | 100 |
| p__Proteobacteria; c__Betaproteobacteria; o__Methylophilales; f__Methylophilaceae | Methylobacillus flagellatus | 100 |
| p__Proteobacteria; c__Alphaproteobacteria; o__Rhizobiales; f__Methylobacteriaceae; g__Methylobacterium | Methylobacterium aerolatum | 100 |
| p__Proteobacteria; c__Alphaproteobacteria; o__Rhizobiales; f__Methylobacteriaceae; g__Methylobacterium; s__ | Methylobacterium phyllostachyos | 99.6 |
| p__Actinobacteria; c__Actinobacteria; o__Actinomycetales; f__Micrococcaceae; g__Micrococcus; s__ | Micrococcus aloeverae strain AE-6 | 100 |
| p__Actinobacteria; c__Actinobacteria; o__Actinomycetales; f__Actinomycetaceae; g__Mobiluncus; s__ | Mobiluncus curtisii | 100 |
| p__Tenericutes; c__Mollicutes; o__Mycoplasmatales; f__Mycoplasmataceae; g__Mycoplasma; s__ | Mycoplasma hominis | 100 |
| p__Firmicutes; c__Clostridia; o__Clostridiales; f__Veillonellaceae | Negativicoccus succinicivorans | 100 |
| p__Actinobacteria; c__Actinobacteria; o__Actinomycetales; f__Bogoriellaceae; g__Georgenia; s__ | Oceanitalea nanhaiensis | 98.42 |
| p__Bacteroidetes; c__Bacteroidia; o__Bacteroidales; f__Porphyromonadaceae; g__Parabacteroides; s__ | Parabacteroides faecis | 98.42 |
| p__Bacteroidetes; c__Bacteroidia; o__Bacteroidales; f__Porphyromonadaceae; g__Parabacteroides; s__ | Parabacteroides merdae | 100 |
| p__Proteobacteria; c__Alphaproteobacteria; o__Rhodobacterales; f__Rhodobacteraceae; g__; s__ | Paracoccus communis | 98.81 |
| p__Firmicutes; c__Clostridia; o__Clostridiales; f__[Tissierellaceae]; g__Parvimonas; s__ | Parvimonas micra | 97.62 |
| p__Proteobacteria; c__Betaproteobacteria; o__Burkholderiales; f__Alcaligenaceae; g__; s__ | Pelistega indica | 99.61 |
| p__Firmicutes; c__Clostridia; o__Clostridiales; f__Peptococcaceae; g__Peptococcus; s__ | Peptococcus niger | 98.81 |
| p__Firmicutes; c__Clostridia; o__Clostridiales; f__[Tissierellaceae]; g__Peptoniphilus; s__ | Peptoniphilus coxii | 100 |
| p__Firmicutes; c__Clostridia; o__Clostridiales; | Peptoniphilus | 100 |

TABLE 4-continued

Species-Level Ideintification of Bacteria Differentially
Observed in Infants by Exposure at Birth

| Taxonomic info | Genus species | BLASTN Identity (%) |
|---|---|---|
| f_[Tissierellaceae]; g_Peptoniphilus; s_ | duerdenii | |
| p_Firmicutes; c_Clostridia; o_Clostridiales; f_[Tissierellaceae]; g_Peptoniphilus; s_ | Peptoniphilus grossensis | 100 |
| p_Firmicutes; c_Clostridia; o_Clostridiales; f_[Tissierellaceae]; g_Peptoniphilus; s_ | Peptoniphilus koenoeneniae | 99.6 |
| p_Firmicutes; c_Clostridia; o_Clostridiales; f_[Tissierellaceae]; g_Peptoniphilus; s_ | Peptoniphilus lacrimalis | 100 |
| p_Firmicutes; c_Clostridia; o_Clostridiales; f_[Tissierellaceae]; g_Peptoniphilus; s_ | Peptoniphilus obesi strain ph1 | 98.02 |
| p_Firmicutes; c_Clostridia; o_Clostridiales; f_[Tissierellaceae]; g_Peptoniphilus; s_ | Peptoniphilus senegalensis | 97.12 |
| p_Firmicutes; c_Clostridia; o_Clostridiales; f_[Tissierellaceae]; g_Peptoniphilus; s_ | Peptoniphilus tyrrelliae | 100 |
| p_Firmicutes; c_Clostridia; o_Clostridiales; f_Peptostreptococcaceae; g_Peptostreptococcus; s_anaerobius | Peptostreptococcus anaerobius | 100 |
| p_Proteobacteria; c_Betaproteobacteria; o_Burkholderiales; f_Comamonadaceae | Polaromonas sp | 99.21 |
| p_Bacteroidetes; c_Bacteroidia; o_Bacteroidales; f_Porphyromonadaceae; g_Porphyromonas; s_ | Porphyromonas bennonis | 99.21 |
| p_Bacteroidetes; c_Bacteroidia; o_Bacteroidales; f_Porphyromonadaceae; g_Porphyromonas; s_ | Porphyromonas somerae | 100 |
| p_Bacteroidetes; c_Bacteroidia; o_Bacteroidales; f_Porphyromonadaceae; g_Porphyromonas; s_ | Porphyromonas uenonis | 99.6 |
| p_Bacteroidetes; c_Bacteroidia; o_Bacteroidales; f_Prevotellaceae; g_Prevotella; s_ | Prevotella amnii | 99.6 |
| p_Bacteroidetes; c_Bacteroidia; o_Bacteroidales; f_Prevotellaceae; g_Prevotella; s_ | Prevotella bergensis | 100 |
| p_Bacteroidetes; c_Bacteroidia; o_Bacteroidales; f_Prevotellaceae; g_Prevotella; s_ | Prevotella bivia | 100 |
| p_Bacteroidetes; c_Bacteroidia; o_Bacteroidales; f_Prevotellaceae; g_Prevotella; s_ | Prevotella buccalis | 99.6 |
| p_Bacteroidetes; c_Bacteroidia; o_Bacteroidales; f_Prevotellaceae; g_Prevotella; s_copri | Prevotella copri | 100 |
| p_Bacteroidetes; c_Bacteroidia; o_Bacteroidales; f_Prevotellaceae; g_Prevotella; s_ | Prevotella corporis | 100 |
| p_Bacteroidetes; c_Bacteroidia; o_Bacteroidales; f_Prevotellaceae; g_Prevotella; s_ | Prevotella disiens | 100 |
| p_Bacteroidetes; c_Bacteroidia; o_Bacteroidales; f_Prevotellaceae; g_Prevotella; s_ | Prevotella timonensis | 100 |
| p_Actinobacteria; c_Actinobacteria; o_Actinomycetales; f_Microbacteriaceae; g_Pseudoclavibacter; s_bifida | Pseudoclavibacter bifida strain IAM 14848 | 99.21 |
| p_Proteobacteria; c_Gammaproteobacteria; o_Pseudomonadales; f_Pseudomonadaceae; g_; s_ | Pseudomonas brenneri | 100 |
| p_Proteobacteria; c_Gammaproteobacteria; o_Pseudomonadales; f_Pseudomonadaceae; g_Pseudomonas; s_ | Pseudomonas helmanticensis | 99.6 |
| p_Proteobacteria; c_Gammaproteobacteria; o_Pseudomonadales; f_Pseudomonadaceae; g_Pseudomonas; s_ | Pseudomonas lini | 100 |
| p_Proteobacteria; c_Gammaproteobacteria; o_Pseudomonadales; f_Pseudomonadaceae; g_Pseudomonas; s_ | Pseudomonas syringae | 99.21 |
| p_Actinobacteria; c_Actinobacteria; o_Actinomycetales; f_Micrococcaceae; g_; s_ | Rothia amarae strain J18 | 97.23 |
| p_Actinobacteria; c_Actinobacteria; o_Actinomycetales; f_Micrococcaceae; g_Rothia; s_mucilaginosa | Rothia mucilaginosa | 98.82 |
| p_Actinobacteria; c_Rubrobacteria; o_Rubrobacterales; f_Rubrobacteraceae; g_Rubrobacter; s_ | Rubrobacter calidifluminis | 98.42 |
| p_Firmicutes; c_Clostridia; o_Clostridiales; f_Ruminococcaceae; g_Ruminococcus; s_ | Ruminococcus bromii | 98.43 |
| p_Firmicutes; c_Clostridia; o_Clostridiales; f_Lachnospiraceae; g_[Ruminococcus]; s_gnavus | Ruminococcus gnavus | 100 |
| p_Fusobacteria; c_Fusobacteriia; o_Fusobacteriales; f_Leptotrichiaceae; g_Sneathia; s_ | Sneathia sanguinegens | 100 |
| p_Proteobacteria; c_Alphaproteobacteria; o_Sphingomonadales; f_Sphingomonadaceae; g_Sphingobium; s_ | Sphingobium yanoikuyae | 100 |
| p_Proteobacteria; c_Alphaproteobacteria; o_Sphingomonadales; f_Sphingomonadaceae; | Sphingopyxis macrogoltabida | 99.6 |

TABLE 4-continued

Species-Level Ideintification of Bacteria Differentially
Observed in Infants by Exposure at Birth

| Taxonomic info | Genus species | BLASTN Identity (%) |
|---|---|---|
| g__Sphingopyxis; s__ | | |
| p__Firmicutes; c__Bacilli; o__Bacillales; f__Planococcaceae; g__; s__ | Staphylococcus carnosus | 100 |
| p__Firmicutes; c__Bacilli; o__Bacillales; f__Staphylococcaceae; g__Staphylococcus | Staphylococcus chromogenes | 97.23 |
| p__Firmicutes; c__Bacilli; o__Bacillales; f__Staphylococcaceae; g__Staphylococcus; s__ | Staphylococcus petrasii | 100 |
| p__Firmicutes; c__Bacilli; o__Bacillales; f__Staphylococcaceae; g__Staphylococcus | Staphylococcus pseudintermedius | 97.23 |
| p__Firmicutes; c__Bacilli; o__Bacillales | Staphylococcus saprophyticus | 100 |
| p__Proteobacteria; c__Gammaproteobacteria; o__Xanthomonadales ; f__Xanthomonadaceae; g__Stenotrophomonas; s__ | Stenotrophomonas maltophilia | 98.81 |
| p__Firmicutes; c__Bacilli; o__Lactobacillales; f__Streptococcaceae; g__Streptococcus; s__agalactiae | Streptococcus agalactiae | N/A |
| p__Firmicutes; c__Bacilli; o__Lactobacillales; f__Streptococcaceae; g__Streptococcus; s__ | Streptococcus agalactiae | 100 |
| p__Firmicutes; c__Bacilli; o__Lactobacillales; f__Streptococcaceae; g__Streptococcus; s__anginosus | Streptococcus anginosus | 100 |
| p__Firmicutes; c__Bacilli; o__Lactobacillales; f__Streptococcaceae; g__Streptococcus; s__anginosus | Streptococcus constellatus | 97.62 |
| p__Firmicutes; c__Bacilli; o__Lactobacillales; f__Streptococcaceae; g__Streptococcus; s__ | Streptococcus dentisani | 100 |
| p__Firmicutes; c__Bacilli; o__Lactobacillales; f__Streptococcaceae; g__Streptococcus; s__ | Streptococcus lactarius | 99.6 |
| p__Firmicutes; c__Bacilli; o__Lactobacillales; f__Streptococcaceae; g__Streptococcus; s__ | Streptococcus thermophilus | 99.21 |
| p__Proteobacteria; c__Betaproteobacteria; o__Burkholderiales; f__Alcaligenaceae; g__Sutterella; s__ | Sutterella stercoricanis | 99.6 |
| p__Tenericutes; c__Mollicutes; o__Mycoplasmatales; f__Mycoplasmataceae; g__Ureaplasma; s__ | Ureaplasma urealyticum | 100 |
| p__Actinobacteria; c__Actinobacteria; o__Actinomycetales; f__Actinomycetaceae; g__Varibaculum; s__ | Varibaculum cambriense | 100 |
| p__Firmicutes; c__Clostridia; o__Clostridiales; f__Veillonellaceae; g__Veillonella; s__dispar | Veillonella dispar | 100 |
| p__Firmicutes; c__Clostridia; o__Clostridiales; f__Veillonellaceae; g__Veillonella; s__ | Veillonella ratti | 99.6 |
| p__Firmicutes; c__Clostridia; o__Clostridiales; f__[Tissierellaceae]; g__1-68; s__ | | |
| p__Firmicutes; c__Clostridia; o__Clostridiales; f__Veillonellaceae; g__Megasphaera; s__ | | |
| p__Fusobacteria; c__Fusobacteriia; o__Fusobacteriales; f__Leptotrichiaceae; g__Leptotrichia; s__ | | |
| p__Proteobacteria; c__Alphaproteobacteria; o__Sphingomonadales; f__Sphingomonadaceae; g__Novosphingobium; s__ | | |
| p__Proteobacteria; c__Betaproteobacteria; o__Neisseriales; f__Neisseriaceae; g__; s__ | | |
| p__Proteobacteria; c__Gammaproteobacteria; o__Xanthomonadales; f__Xanthomonadaceae; g__Stenotrophomonas; s__ | | |

Example 2: Restoration by Exposure to Vaginal Fluids in C-Section Delivered Infants Since Cesarean-delivered infants were exposed to vaginal fluids through the use of sterile gauzes, the similarity of the microbiota of the gauzes to samples obtained from maternal body sites at day 1 was determined. The gauzes contained vaginal bacteria such as *Lactobacillus, Prevotella, Garnerella*, and in less proportion by *Atopobium, Sneathia, Fusobacterium*, and *Ureoplasma*, and were more similar to the microbiota of maternal vagina, than to that in other body sites (ANOVA p<0.01).

Vaginal gauze exposure lead to an infant microbiota closer to that typical of vaginal than C-section delivery, with partially restored vaginal markers that were lacking in C-section infants (FIG. 2, FIG. 6, Table 5). Major restored bacteria included *Lactobacillus* in all infant sites and the early bloom of gut *Bacteroides*, oral *Gemella*, and skin *Bacteroidales* S24-7 and *Stenotrophomonas*. However, these gauze-exposed C-section babies also showed some markers of C-section delivery, such as high anal *Streptococcus* (FIG. 2, Table 5). Random Forest predictions indicated that mode of delivery could be predicted using oral or skin microbes. C section birthing was more accurately predicted than vaginal delivery, and mode of delivery of babies born by C-section with gauze exposure could not be predicted, indicating an intermediate composition.

TABLE 5

Bacteria differentially observed in infants by exposure at birth

| Bacterial genus | Delivery mode | Vaginal | Cesarean | |
|---|---|---|---|---|
| | Vaginal exposure at birth | + | + | − |
| | Infant body site | | | |
| *Lactobacillus* | All | + | + | − |
| *Bacteroides* | Anal | + | + | − |
| *Clostridium* | Anal | + | − | − |
| *Bifidobacterium* | Anal | + | − | − |
| *Streptococcus* | Skin and mouth | + | − | − |
| *Staphylococcus* | Skin and mouth | + | − | − |
| *Bacteroidales* S24-7 | Skin | + | + | − |
| *Stenotrophomonas* | Skin | + | + | − |
| *Gemellaceae* | Mouth | + | + | − |
| *Streptococcus* | Anal | − | − | + |
| *Veillonella* | Anal | − | − | + |

These results demonstrate that babies born vaginally showed a highly variable microbiota in all body sites (high inter-individual Unifrac distances), while C-section babies showed a microbiota with lower variability, similar to that in maternal skin. C-section babies exposed to maternal inoculum showed communities resembling more those of the maternal vagina, with intermediate variability in relation to the other two groups. By day 30, oral and skin (but not fecal) microbiota clusters with the corresponding maternal site. Therefore, exposing babies delivered by C-section to the vaginal microbiota of their mothers partially restores normal microbial colonization patterns to resemble vaginally delivered infants.

The invention thus provides that newborns exposed to the vaginal canal or gauze, acquire their mother's vaginal bacterial populations. Blooms of bacteria that occur in newborns are still associated with maternal bacteria and with feeding mode. Babies are born with a bacterial diversity that is higher than mother's vagina, and decreases sharply after birth, presumably due to the selective pressure of milk. Babies that are breastfed have oral and skin (forehead and arm) bacterial communities closer to their mother's (aureole). Feeding mode (breastfed or formula fed) can be predicted based on the closeness of baby (oral, forehead skin) and mother's (aureole) bacterial communities. Formula allows higher colonization of several bacteria such as *Leptotrichia*.

It is demonstrated herein that disruption of the natural birth or feeding process alters significantly the microbiota of babies, in a crucial developmental stage. Babies born by C-section can normalize their microbiota (e.g., resemble vaginally delivered babies) at birth, by being exposed to their mother's vaginal inoculum. The newborn bacterial diversity of the mouth and anal microbiota decreases soon after birth, and is maintained remarkably low during the first month of life. Breast feeding maintains closer baby-mother microbiota.

Example 3: Determine the Bacteria that Normalizes the Immune and Metabolic Development in Mice The goal of the study is to determine if microbiota of C-section born infants leads to higher inflammatory response and is more obesogenic.

Transfer of whole natural microbiota or mixed or pure isolates (i) from human maternal vagina or (ii) from meconium/feces from babies born vaginally are used to determine immune profile and metabolic responses in GF mice, and are compared to GF mice who received a transfer of microbiota (iii) from meconium/feces from babies delivered by C-section.

The aim is to determine the microbial taxa responsible for the observed differences, and to optimize for restoring healthy phenotypes, i.e., minimizing the differences in responses of C-section related exposures, in relation to the vaginal control group. The final desired outcome is the alleviation of exposures that increase the risks of C-section associated disorders, using microbial exposures natural to mammals.

Example 4: Sequences

Sequences were obtained for region V4 of the 16S rRNA gene and compared to the bacterial database "Greenhenes". Taxa were identified with an identity of >97%. OTUs grouped sequences sharing more than 97% identity. The data is provided in Table 6.

TABLE 6

| OTU | Time (weeks) | Site | Test-Statistic | p | Group | VD_1W_mean | CS_1W_mean | Taxonomy | Representative sequence | SEQ ID NO |
|---|---|---|---|---|---|---|---|---|---|---|
| 4393532 | 1 | Baby anal | 3.75 | 0.052807511 | VD | 1.4 | 0 | k_Bacteria; p_Actinobacteria; c_Coriobacteriia; o_Coriobacteriales; f_Coriobacteriaceae; g_Eggerthella; s_lenta | TACGTAGGGAGC GAGCGTTATCCG GATTCATTGGGC GTAAAGAGCGC GTAGGCGCCTC TCAAGCGGATC TCTAATCGAGG GCTCAACCCCGA GCCGGATCCCGA ACTGGGAGGCTC GAGTTCGTAGA GGCAGGCCGAA TTCCCGTGTAG CGGTGGAATGCG CAGATATCGGGA AGAACACCGAT GGCGAAGGCAG CCTGCTGGCCG CAACTGACGCTG AGGCGCGAAAG CTAGGGGAGCG AACAGG | 1 |
| 947112 | 1 | Baby anal | 3.71559633 | 0.053906366 | VD | 10 | 0 | k_Bacteria; p_Actinobacteria; c_Actinobacteria; o_Actinomycetales; f_Corynebacteriaceae; g_Corynebacterium; s_ | TACGTAGGGTGC GAGCGTTGTCCG GAATTACTGGGC GTAAAGAGCTCG TAGGTGGTTTGT CCGCTGCTCTGT GAAATTCCGGGG CTTAACTCCGGG CCGTGCAGCGAT ACCGGCATAACT TGAGTACTGTAG GGGAGACTGGA AATTCCTGGTGTA GCCGTGAAATGC GCAGATATCAGG AGGAACACCGG TGGCGAAGGCG GGTCTCTGGGCA GTAACTGACGCT GACGAGCGAAA GCATGGGGAGC GAACAGG | 2 |
| 4468234 | 1 | Baby anal | 3.71559633 | 0.053906366 | VD | 17.4 | 0 | k_Bacteria; p_ | TACGGAGGATCC GAGCGTTATCCG | 3 |

TABLE 6-continued

| OTU | Time (weeks) | Site | Test-Statistic | p | Group | VD_1W_mean | CS_1W_mean | Taxonomy | Representative sequence | SEQ ID NO |
|---|---|---|---|---|---|---|---|---|---|---|
| | | | | | | | | Bacteroidetes; c_Bacteroidia; o_Bacteroidales; f_Bacteroidaceae; g_Bacteroides; s_ | GATTTATTGGGT TTAAGGGAGC GTAGATGATGT TTAAGTCAGTTG TGAAAGTTTGCG GCTCAACCGTAA AATTGCAGTTGA TACTGGATGTCT TGAGTGCAGTTG AGGCAGGCGA ATTCGTGTGTA GCGGTGAAATGC TTAGATATCACG AAGAACTCCGAT TGCGAAGGCAG CCTGCTAGGCTG CAACTGACATTG AGGCTCGAAAGT GTGGGTATCAAA CAGG | |
| 4376828 | 1 | Baby anal | 3.71559633 | 0.053906366 | VD | 1.2 | 0 | k_Bacteria; p_Actinobacteria; c_Actinobacteria; o_Bifidobacteriales; f_Bifidobacteriaceae; g_Bifidobacterium; s_ | TACGTAGGGCGC AAGCGTTATCCG GATTTATTGGGC GTAAAGGGCTCG TAGGCGGCTCGT CCGTCCGGTGT GAAAGTCCATCG CTTAACGGTGGA TCTGCCCGGGT ACGGGCGGGCTT GAGTGCGGTAG GGGAGACTGGA ATTCCCGGTGTA ACGGTGGAATGT GTAGATATCGGG AAGAACACCAA TGGCGAAGGCA GGTCTCTGGGCC GTTACTGACGCT GAGGAGCGAAA GCGTGGGGAGC GAACAGG | 4 |
| 578016 | 1 | Baby anal | 3.71559633 | 0.053906366 | VD | 14.2 | 0 | k_Bacteria; p_Bacteroidetes; c_Bacteroidia; o_Bacteroidales; f_ | TACGGAGGATCC GAGCGTTATCCG GATTTATTGGGT TTAAGGGTGCG TAGGCGGCCTTT TAAGTCAGCGGT | 5 |

TABLE 6-continued

| OTU | Time (weeks) | Site | Test-Statistic | p | Group | VD_1W_mean | CS_1W_mean | Taxonomy | Representative sequence | SEQ ID NO |
|---|---|---|---|---|---|---|---|---|---|---|
| 495067 | 1 | Baby anal | 3.37155963 | 0.053906366 | VD | 19.4 | 0 | Porphyro-monadaceae; g_Parabacteroides; s_distasonis | GAAAGTCTGTGG CTCAACCATAGA ATTGCCCTTGAA ACTGGGGGGCTT GAGTATGTTTGA GGCAGGCGGAA TGCGTGGTGTAG CGGTGAAATGCT TAGATATCACGC AGAACCCGATT GCGAAGGCAGC CTGCCAAGCCAT GACTGACCGCTGA TGCACGAAAGC GTGGGGATCAA ACAGG | |
| 495067 | 1 | Baby anal | 3.37155963 | 0.053906366 | VD | 19.4 | 0 | k_Bacteria; p_Actinobacteria; c_Actinobacteria; o_Actinomycetales; f_Coryne-bacteriaceae; g_Corynebacterium; s_ | TACGTAGGGTGC GAGCGTTGTCCG GAATTACTGGGC GTAAAGAGCTCG TAGGCGGTTTGT CACGTCGTCTGT GAAATCCTAGGG CTTAACCCTAGGA CGTGCAGGCGAT ACGGGCTGACTT GAGTACTACAGG GGAGACTGAA TTTCTGGTGTAG CGGTGGAATGCA CAGATATCAGGA AGAACACCGAT GGCGAAGGCAG GTCTCTGGGTAG TAACTGACGCTG AGGAGCGAAAG CATGGGTAGCGA ACAGG | 6 |
| 114510 | 1 | Baby anal | 3.71559633 | 0.053906366 | VD | 4.8 | 0 | k_Bacteria; p_Proteobacteria; c_Gammapro-teobacteria; o_Enterobacteriales; f_Enterobacteriaeae; g_; s_ | TACGGAGGGTGC AAGCGTTAATCG GAATTACTGGGC GTAAAGCGCAC GCAGGCGGTTTG TTAAGTCAGATG TGAAATCCCCGG GCTCAACCTGGG AACTGCATCTGA TACTGGCAAGCT | 7 |

TABLE 6-continued

| OTU | Time (weeks) | Site | Test-Statistic | p | Group | VD_1W_mean | CS_1W_mean | Taxonomy | Representative sequence | SEQ ID NO |
|---|---|---|---|---|---|---|---|---|---|---|
| 526804 | 4 | Baby anal | 4.4 | 0.035938931 | VD | 1.6 | 0 | k_Bacteria; p_Firmicutes; c_Bacilli; o_Lactobacillales; f_Streptococcaceae; g_Streptococcus; s_ | TGAGTCTCGTAG AGGGGGTAGA ATTCCAGTGTA GCGGTGAAATGC GTAGAGATCTGG AGGAATACCGGT GGCGAAGGCGG TACGTAGGTCCC GAGCGTTATCCG GATTTATTGGGC GTAAAGCGAGC GCAGGCGGTTAG ATAAGTCTGAAG TTAAAGCTGTG GCTTAACCATAG TACGCTTTGGAA ACTGTTTAACTT GAGTGCAGAAG GGGAGAGTGGA ATTCCATGTGTA GCGGTGAAATGC GTAGATATATGG AGGAACACCGG TGCGAAGCG GCTCTCTGGTCT GTAACTGACGCT GAGGCTCGAAA GCGTGGGGAGC GAACAGG | 8 |
| 1082607 | 4 | Baby anal | 4.367647059 | 0.036627535 | VD | 2.4 | 0 | k_Bacteria; p_Actinobacteria; c_Actinobacteria; o_Actinomycetales; f_Corynebacteriaceae; g_Corynebacterium; s_ | TACGTAGGGTGC GAGCGTTGTCCG GAATTACTGGGC GTAAAGAGCTCG TAGGCGTTTGT CACGTCGTCTGT GAAATCCTAGGG CTTAACCCTGA CGTGCAGGCGAT ACGGGCTGACTT GAGTACTACAGG GGAGACTGGAA TTTCTGGTGTAG CGGTGGAATGCA CAGATATCAGGA AGAACACCGAT GGCGAAGGCAG GTCTCTGGGTAG TAACTGACGCTG | 9 |

TABLE 6-continued

| OTU | Time (weeks) | Site | Test-Statistic | p | Group | VD_1W_mean | CS_1W_mean | Taxonomy | Representative sequence | SEQ ID NO |
|---|---|---|---|---|---|---|---|---|---|---|
| 495067 | 4 | Baby anal | 4.367647059 | 0.036627535 | VD | 22 | 0 | k_Bacteria; p_Actinobacteria; c_Actinobacteria; o_Actinomycetales; f_Corynebacteriaceae; g_Corynebacterium; s_ | AGGAGCGAAAG CATGGGAGCG AACAGG TACGTAGGGTGC GAGCGTTGTCCG GAATTACTGGGC GTAAAGAGCTCG TAGGCGGTTTGT CACGTCGTCTGT GAAATCCTAGGG CTTAACCCTGGA CGTGCAGGCGAT ACGGGCTGACTT GAGTACTACAGG GGAGACTGGAA TTTCTGGTGTAG CGGTGGAATGCA CAGATATCAGGA AGAACACCGAT GGCGAAGGCAG GTCTCTGGGTAG TAACTGACGCTG AGGAGCGAAAG CATGGGTAGCGA ACAGG | 10 |
| 4425214 | 4 | Baby anal | 3.348554033 | 0.067264075 | VD | 32.6 | 11 | k_Bacteria; p_Firmicutes; c_Bacilli; o_Lactobacillales; f_Streptococcaceae; g_Streptococcus; s_ | TACGTAGGTCCC GAGCGTTGTCCG GATTTATTGGGC GTAAAGCGAGC GCAGGCGGTTTG ATAAGTCTGAAG TTAAAGGCTGTG GCTCAACCATAG TTCGCTTTGGAA ACTGTCAAACTT GAGTGCAGAAG GGGAGAGTGGA ATTCCATGTGTA GCGGTGAAATGC GTAGATATATGG AGGAACACCGG TGGCGAAAGCG GCTCTCTGGTCT GTAACTGACGCT GAGGCTCGAAA GCGTGGGGAGC GAACAGG | 11 |

TABLE 6-continued

| OTU | Time (weeks) | Site | Test-Statistic | p | Group | VD_1W_mean | CS_1W_mean | Taxonomy | Representative sequence | SEQ ID NO |
|---|---|---|---|---|---|---|---|---|---|---|
| 4429335 | 4 | Baby anal | 2.879528986 | 0.08971226 | VD | 8.2 | 0.833333333 | k_Bacteria; p_Firmicutes; c_Clostridia; o_Clostridiales; f_[Tissierellaceae]; g_Peptoniphilus; s_ | TACGTAGGGGC TAGCGTTGTCCG GAATCACTGGGC GTAAAGGGTTCG CAGGCGAAAT GCAAGTCAGGTG TAAAAGGCAGT AGCTTAACTACT GTAAGCATTTGA AACTGCATATCT TGAGAAGAGTA GAGGTAAGTGG AATTTTTAGTGT AGCGGTGAAAT GCGTAGATATTA AAAGAATACC GGTGGCGAAGG CGACTACTGGG CTCATTCTGACG CTGAGGAACGA AAGCGTGGGTA GCAAACAGG | 12 |

REFERENCES

1. M. G. Dominguez-Bello, E. K. Costello, M. Contreras, M. Magris, G. Hidalgo, N. Fierer, R. Knight, Delivery mode shapes the acquisition and structure of the initial microbiota across multiple body habitats in newborns. Proc Natl Acad Sci USA 107, 11971-11975 (2010); published online EpubJun 29 (1002601107 [pii]10.1073/pnas.1002601107).
2. M. Mshvildadze, J. Neu, J. Shuster, D. Theriaque, N. Li, V. Mai, Intestinal microbial ecology in premature infants assessed with non-culture-based techniques. The Journal of pediatrics 156, 20-25 (2010); published online EpubJan (10.1016/j.jpeds.2009.06.063).
3. K. Aagaard, J. Ma, K. M. Antony, R. Ganu, J. Petrosino, J. Versalovic, The placenta harbors a unique microbiome. Science translational medicine 6, 237ra265 (2014); published online EpubMay 21 (10.1126/scitranslmed.3008599).
4. K. Aagaard, K. Riehle, J. Ma, N. Segata, T. A. Mistretta, C. Coarfa, S. Raza, S. Rosenbaum, I. Van den Veyver, A. Milosavljevic, D. Gevers, C. Huttenhower, J. Petrosino, J. Versalovic, A metagenomic approach to characterization of the vaginal microbiome signature in pregnancy. Plos One 7, e36466 (2012)10.1371/journal.pone.0036466).
5. O. Koren, J. K. Goodrich, T. C. Cullender, A. Spor, K. Laitinen, H. K. Backhed, A. Gonzalez, J. J. Werner, L. T. Angenent, R. Knight, F. Backhed, E. Isolauri, S. Salminen, R. E. Ley, Host remodeling of the gut microbiome and metabolic changes during pregnancy. Cell 150, 470-480 (2012); published online EpubAug 3 (10.1016/j.cell.2012.07.008).
6. A. S. Neish, Microbes in gastrointestinal health and disease. Gastroenterology 136, 65-80 (2009); published online EpubJan (10.1053/j.gastro.2008.10.080).
7. C. Palmer, E. M. Bik, D. B. Digiulio, D. A. Relman, P. O. Brown, Development of the Human Infant Intestinal Microbiota. Plos Biol 5, e177 (2007)07-PLBI-RA-0129 [pii] 10.1371/journal.pbio.0050177).
8. H. R. Gaskins, J. A. Croix, N. Nakamura, G. M. Nava, Impact of the intestinal microbiota on the development of mucosal defense. Clinical Infectious Diseases 46, S80-86 (2008).
9. R. A. Dimmitt, E. M. Staley, G. Chuang, S. M. Tanner, T. D. Soltau, R. G. Lorenz, Role of Postnatal Acquisition of the Intestinal Microbiome in the Early Development of Immune Function. J Pediatr Gastroenterol Nutr, (2010); published online EpubJul 14 (10.1097/MPG.0b013e3181e1a114).
10. J. E. Koenig, A. Spor, N. Scalfone, A. D. Fricker, J. Stombaugh, R. Knight, L. T. Angenent, R. E. Ley, Succession of microbial consortia in the developing infant gut microbiome. P Natl Acad Sci USA 108 Suppl 1, 4578-4585 (2011); published online EpubMar 15 (10.1073/pnas.1000081107).
11. J. F. Bach, The effect of infections on susceptibility to autoimmune and allergic diseases. The New England journal of medicine 347, 911-920 (2002)
12. N. T. Mueller, E. Bakacs, J. Combellick, Z. Grigoryan, M. G. Dominguez-Bello, The infant microbiome development: mom matters. Trends in molecular medicine 21, 109-117 (2015); published online EpubFeb (10.1016/j.molmed.2014.12.002).
13. D. J. Barker, Human growth and chronic disease: a memorial to Jim Tanner. Annals of human biology 39, 335-341 (2012); published online EpubSep (10.3109/03014460.2012.712717).
14. S. Thavagnanam, J. Fleming, A. Bromley, M. D. Shields, C. R. Cardwell, A meta-analysis of the association between Caesarean section and childhood asthma. Clinical and experimental allergy: journal of the British Society for Allergy and Clinical Immunology 38, 629-633 (2008); published online EpubApr (10.1111/j.1365-2222.2007.02780.x).
15. H. Renz-Polster, M. R. David, A. S. Buist, W. M. Vollmer, E. A. O'Connor, E. A. Frazier, M. A. Wall, Caesarean section delivery and the risk of allergic disorders in childhood. Clinical and experimental allergy: journal of the British Society for Allergy and Clinical Immunology 35, 1466-1472 (2005); published online EpubNov (10.1111/j.1365-2222.2005.02356.x).
16. C. Roduit, S. Scholtens, J. C. de Jongste, A. H. Wijga, J. Gerritsen, D. S. Postma, B. Brunekreef, M. O. Hoekstra, R. Aalberse, H. A. Smit, Asthma at 8 years of age in children born by caesarean section. Thorax 64, 107-113 (2009); published online EpubFeb (10.1136/thx.2008.100875).
17. M. Pistiner, D. R. Gold, H. Abdulkerim, E. Hoffman, J. C. Celedon, Birth by cesarean section, allergic rhinitis, and allergic sensitization among children with a parental history of atopy. The Journal of allergy and clinical immunology 122, 274-279 (2008); published online EpubAug (10.1016/j.jaci.2008.05.007).
18. S. Hakansson, K. Kallen, Caesarean section increases the risk of hospital care in childhood for asthma and gastroenteritis. Clinical and experimental allergy: journal of the British Society for Allergy and Clinical Immunology 33, 757-764 (2003)
19. A. Sevelsted, J. Stokholm, K. Bonnelykke, H. Bisgaard, Cesarean section and chronic immune disorders. Pediatrics 135, e92-98 (2015); published online EpubJan (10.1542/peds.2014-0596).
20. J. Couzin-Frankel, Bacteria and asthma: untangling the links. Science 330, 1168-1169 (2010); published online EpubNov 26 (330/6008/1168 [pii]10.1126/science.330.6008.1168).
21. J. Kero, M. Gissler, M. M. Gronlund, P. Kero, P. Koskinen, E. Hemminki, E. Isolauri, Mode of delivery and asthma—is there a connection? Pediatr Res 52, 6-11 (2002); published online EpubJul (10.1203/00006450-200207000-00004).
22. P. Bager, J. Simonsen, N. M. Nielsen, M. Frisch, Cesarean section and offspring's risk of inflammatory bowel disease: a national cohort study. Inflammatory bowel diseases 18, 857-862 (2012); published online EpubMay (10.1002/ibd.21805).
23. K. Marild, O. Stephansson, S. Montgomery, J. A. Murray, J. F. Ludvigsson, Pregnancy outcome and risk of celiac disease in offspring: a nationwide case-control study. Gastroenterology 142, 39-45 e33 (2012); published online EpubJan (10.1053/j.gastro.2011.09.047).
24. E. Decker, G. Engelmann, A. Findeisen, P. Gerner, M. Laass, D. Ney, C. Posovszky, L. Hoy, M. W. Hornef, Cesarean delivery is associated with celiac disease but not inflammatory bowel disease in children. Pediatrics 125, e1433-1440 (2010); published online EpubJun (10.1542/peds.2009-2260).
25. N. T. Mueller, R. Whyatt, L. Hoepner, S. Oberfield, M. G. Dominguez-Bello, E. M. Widen, A. Hassoun, F. Perera, A. Rundle, Prenatal exposure to antibiotics, cesarean section and risk of childhood obesity. Int J Obes (Lond), (2014); published online EpubNov 11 (10.1038/ijo.2014.180).

26. D. N. Mesquita, M. A. Barbieri, H. A. Goldani, V. C. Cardoso, M. Z. Goldani, G. Kac, A. A. Silva, H. Bettiol, Cesarean Section Is Associated with Increased Peripheral and Central Adiposity in Young Adulthood: Cohort Study. Plos One 8, e66827 (2013)10.1371/journal-.pone.0066827).
27. L. M. Cox, M. J. Blaser, Pathways in microbe-induced obesity. Cell metabolism 17, 883-894 (2013); published online EpubJun 4 (10.1016/j.cmet.2013.05.004).
28. L. M. Cox, S. Yamanishi, J. Sohn, A. V. Alekseyenko, J. M. Leung, I. Cho, S. G. Kim, H. Li, Z. Gao, D. Mahana, J. G. Zarate Rodriguez, A. B. Rogers, N. Robine, P. Loke, M. J. Blaser, Altering the intestinal microbiota during a critical developmental window has lasting metabolic consequences. Cell 158, 705-721 (2014); published online EpubAug 14 (10.1016/j.cell.2014.05.052).
29. I. Cho, S. Yamanishi, L. Cox, B. A. Methe, J. Zavadil, K. Li, Z. Gao, D. Mahana, K. Raju, I. Teitler, H. Li, A. V. Alekseyenko, M. J. Blaser, Antibiotics in early life alter the murine colonic microbiome and adiposity. Nature 488, 621-626 (2012); published online EpubAug 30 (10.1038/nature11400).
30. L. M. Cox, M. J. Blaser, Antibiotics in early life and obesity. Nature reviews. Endocrinology, (2014); published online EpubDec 9 (10.1038/nrendo.2014.210).
31. C. Finger, Caesarean section rates skyrocket in Brazil. Many women are opting for caesareans in the belief that it is a practical solution. Lancet 362, 628 (2003)
32. T. A. Ajslev, C. S. Andersen, M. Gamborg, T. I. A. Sorensen, T. Jess, Childhood overweight after establishment of the gut microbiota: the role of delivery mode, pre-pregnancy weight and early administration of antibiotics. International Journal of Obesity. 35, 522-529 (2011).
33. J. G. Caporaso, J. Kuczynski, J. Stombaugh, K. Bittinger, F. D. Bushman, E. K. Costello, N. Fierer, A. G. Pena, J. K. Goodrich, J. I. Gordon, G. A. Huttley, S. T. Kelley, D. Knights, J. E. Koenig, R. E. Ley, C. A. Lozupone, D. McDonald, B. D. Muegge, M. Pirrung, J. Reeder, J. R. Sevinsky, P. J. Turnbaugh, W. A. Walters, J. Widmann, T. Yatsunenko, J. Zaneveld, R. Knight, QIIME allows analysis of high-throughput community sequencing data. Nature methods 7, 335-336 (2010); published online EpubMay (nmeth.f.303 [pii]10.1038/nmeth.f.303).
34. H. Ochman, M. Worobey, C. H. Kuo, J. B. Ndjango, M. Peeters, B. H. Hahn, P. Hugenholtz, Evolutionary relationships of wild hominids recapitulated by gut microbial communities. Plos Biol 8, e1000546 (2010)10.1371/journal.pbio.1000546).
35. P. Soares, L. Ermini, N. Thomson, M. Mormina, T. Rito, A. Rohl, A. Salas, S. Oppenheimer, V. Macaulay, M. B. Richards, Correcting for purifying selection: an improved human mitochondrial molecular clock. American journal of human genetics 84, 740-759 (2009); published online EpubJun (10.1016/j.ajhg.2009.05.001).
36. I. G. Pantoja-Feliciano, J. C. Clemente, E. K. Costello, M. E. Perez, M. J. Blaser, R. Knight, M. G. Dominguez-Bello, Biphasic assembly of the murine intestinal microbiota during early development. The ISME journal 7, 1112-1115 (2013); published online EpubJun (10.1038/ismej.2013.15).
37. OECD, "Health at a Glance 2011: OECD indicators," (OECD Publishing, 2011).
38. M. J. Ege, M. Mayer, A. C. Normand, J. Genuneit, W. O. Cookson, C. Braun-Fahrlander, D. Heederik, R. Piarroux, E. von Mutius, Exposure to environmental microorganisms and childhood asthma. The New England journal of medicine 364, 701-709 (2011); published online EpubFeb 24 (10.1056/NEJMoa1007302).
39. C. S. Algert, A. McElduff, J. M. Morris, C. L. Roberts, Perinatal risk factors for early onset of Type 1 diabetes in a 2000-2005 birth cohort. Diabet Med 26, 1193-1197 (2009); published online EpubDec (10.1111/j.1464-5491.2009.02878.x).
40. A. Aumeunier, F. Grela, A. Ramadan, L. Pham Van, E. Bardel, A. Gomez Alcala, P. Jeannin, S. Akira, J. F. Bach, N. Thieblemont, Systemic Toll-like receptor stimulation suppresses experimental allergic asthma and autoimmune diabetes in NOD mice. Plos One 5, e11484 (2010) 10.1371/journal.pone.0011484).
41. S. Y. Huh, S. L. Rifas-Shiman, C. A. Zera, J. W. Edwards, E. Oken, S. T. Weiss, M. W. Gillman, Delivery by caesarean section and risk of obesity in preschool age children: a prospective cohort study. Arch Dis Child 97, 610-616 (2012); published online EpubJul (10.1136/archdischild-2011-301141).
42. J. Blustein, T. Attina, M. Liu, A. Ryan, L. Cox, M. Blaser, L. Trasande, Association of caesarean delivery with child adiposity from age 6 weeks to 15 years. International Journal of Obesity 37, 900-906 (2013).
43. J. G. Caporaso, C. L. Lauber, W. A. Walters, D. Berg-Lyons, J. Huntley, N. Fierer, S. M. Owens, J. Betley, L. Fraser, M. Bauer, N. Gormley, J. A. Gilbert, G. Smith, R. Knight, Ultra-high-throughput microbial community analysis on the Illumina HiSeq and MiSeq platforms. The ISME journal 6, 1621-1624 (2012); published online EpubAug (10.1038/ismej.2012.8).
44. N. Segata, J. Izard, L. Waldron, D. Gevers, L. Miropolsky, W. S. Garrett, C. Huttenhower, Metagenomic biomarker discovery and explanation. Genome biology 12, R60 (2011)10.1186/gb-2011-12-6-r60).

1. A method for restoring normal microbiota in an infant delivered by Cesarean section, said method comprising administering to said infant at the time of birth and/or within the first 4 months of life an effective amount of a vaginal microbiota inoculum, wherein said inoculum is obtained from the subject's mother or from a donor during the third trimester of pregnancy before or at the time of giving birth.

2. The method of item 1, wherein the vaginal microbiota inoculum is administered to the infant within the first 24 hours of life.

3. A method for restoring normal microbiota in a pre-term infant, said method comprising administering to said infant at the time of birth and/or within the first 4 months of life an effective amount of a vaginal microbiota inoculum, wherein said inoculum is obtained from the subject's mother or from a donor during the third trimester of pregnancy before or at the time of giving birth.

4. The method of item 3, wherein the vaginal microbiota inoculum is administered to the newborn subject within the first hour of life.

5. A method for treating a disease in a subject associated with the subject's delivery by Cesarean section or with the subject's pre-term birth, said method comprising administering to said subject at the time of birth and/or within the first 4 months of life a therapeutically effective amount of a vaginal microbiota inoculum, wherein said inoculum is obtained from the subject's mother or from a donor during the third trimester of pregnancy before or at the time of giving birth.

6. The method of item 5, wherein said disease is an inflammatory or an autoimmune disorder.

7. The method of item 5, wherein said disease is selected from the group consisting of autoimmune diseases, allergic diseases, infectious diseases, and rejection in organ transplantations.

8. The method of item 5, wherein said disease is selected from the group consisting of asthma, allergy, celiac disease, type 1 diabetes, obesity, necrotizing enterocolitis, inflammatory bowel disease (IBD), ulcerative colitis, Crohn's disease, sprue, autoimmune arthritis, rheumatoid arthritis, multiple sclerosis, graft vs. host disease following bone marrow transplantation, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, and atherosclerosis.

9. The method of any one of items 1-8, wherein the vaginal microbiota inoculum is delivered to the mouth, nose, and/or skin of the infant.

10. The method of any one of items 1-8, wherein the vaginal microbiota inoculum is administered to the infant by a route selected from the group consisting of oral, topical, rectal, mucosal, sublingual, nasal, and via naso/oro-gastric gavage.

11. The method of any one of items 1-10, wherein the vaginal microbiota inoculum is administered to the infant by placing it on the maternal breast and/or chest.

12. The method of any one of items 1-11, wherein the vaginal microbiota inoculum is delivered to the infant in a form of a liquid, foam, cream, spray, powder, or gel.

13. The method of any one of items 1-11, wherein the vaginal microbiota inoculum is delivered to the infant in a form of a composition which comprises (i) a carrier and/or excipient and/or (ii) one or more prebiotic agents which stimulate growth and/or activity of one or more bacteria present in the composition.

14. The method of item 13, wherein the composition comprises a buffering agent to adjust pH to the natural vaginal pH at the time of labor or to a pH of 3.5 to 7.

15. The method of item 13 or 14, wherein the composition comprises an excipient or a carrier that optimizes the seeding of the transferred microbiota.

16. The method of any one of items 1-15, wherein the vaginal microbiota inoculum is obtained and/or delivered using an absorbent material or device.

17. The method of item 16, wherein the absorbent material or device is selected from the group consisting of gauze, sponge, and tampon.

18. The method of item 16 or 17, wherein the vaginal microbiota inoculum is transferred to said absorbent material or device by introducing said absorbent material or device in vagina prior to the birth or at the time of Cesarean section.

19. The method of item 18, wherein said absorbent material or device is introduced in the vagina for at least 5 minutes.

20. The method of any one of items 1-19, wherein said vaginal microbiota inoculum, after it is obtained from the subject's mother or the donor, is stored in a frozen form.

21. The method of any one of items 1-20, wherein said vaginal microbiota inoculum, after it is obtained from the subject's mother or the donor, is processed to isolate desired bacteria as single or mixed cultures and such mixed or single cultures are then administered to the infant.

22. The method of any one of items 1-21, wherein said vaginal microbiota inoculum is lyophilized after it is obtained from the subject's mother or the donor and reconstituted prior to the administration to the infant.

23. The method of any one of items 1-12, wherein prior to obtaining vaginal microbiota inoculum from the newborn's mother or the donor, it is verified that said mother or donor does not have Group B *Streptococcus* (GBS), human immunodeficiency virus (HIV), and/or *Chlamydia*.

24. The method of any one of items 1-23, wherein prior to obtaining vaginal microbiota inoculum from the newborn's mother or the donor, it is verified that said mother or donor does not have sexually transmitted diseases.

25. The method of any one of items 1-24, wherein prior to obtaining vaginal microbiota from the newborn's mother or the donor, it is verified that said mother's or donor's vaginal pH is less than 4.5.

26. The method of any one of items 1-25, wherein the newborn's mother or the donor has not been administered antibiotic compounds at least one month prior to the collection of the microbiota, has body mass index (BMI) between 18.5 and 24.9, and does not have irritable bowel disease, Crohn's disease, ulcerative colitis, irritable bowel syndrome, celiac disease, colorectal cancer, and a family history of these diseases.

27. The method of any one of items 1-26, further comprising monitoring the infant's microbiota after the administration of the vaginal microbiota inoculum by:
(a) determining a relative abundance of one or more bacterial taxa in a microbiota sample obtained from the infant, and
(b) comparing the relative abundance(s) determined in step (a) to (i) a predetermined standard value or (ii) to the abundance(s) of the same taxa in a control subject or (iii) to the average value of abundances of the same taxa in several control subjects.

28. The method of item 27, wherein the infant's microbiota sample is isolated from feces, skin, oral mucosa, conjunctive mucosa, or nasal mucosa.

29. The method of item 27 or item 28, wherein the control subject is a vaginally delivered full-term healthy infant.

30. The method of item 29, wherein the control subject is born to a mother who has not been administered antibiotic compounds at least one month prior to giving birth, has body mass index (BMI) between 18.5 and 24.9, and does not have irritable bowel disease, Crohn's disease, ulcerative colitis, irritable bowel syndrome, celiac disease, colorectal cancer, and a family history of these diseases.

31. The method of any one of items 27-30, wherein determining the relative abundance of the bacterial taxa comprises a method selected from the group consisting of quantitative polymerase chain reaction (qPCR), sequencing of bacterial 16S rRNA, shotgun metagenome sequencing, and metabolomics.

32. The method of any one of items 27-31, wherein the bacterial taxa comprise one or more taxa selected from the group consisting of *Lactobacillus, Bacteriodales, Bacteroides, Parabacteroides, Bacteroidacea, Porphyromonadaceae, Coriobacteriales, Bifidobacterium, Clostridiaceae, Stenotrophomonas*, and *Gemella*.

33. The method of item 30, wherein *Bacteriodales* is S24-7.

34. The method of any one of items 27-31, wherein the bacterial taxa comprise one or more taxa recited in Table 1A.

35. The method of any one of items 27-31, wherein the bacterial taxa comprise one or more species recited in Table 1B.

36. The method of any one of items 27-31, wherein the bacterial taxa comprise family Neisseriaceae.

37. A method for restoring normal microbiota in an infant delivered by Cesarean section, said method comprising administering to said infant at the time of birth and/or within the first 4 months of life an effective amount of a probiotic composition, wherein said probiotic composition (i) stimulates growth and/or activity of bacteria which are under-represented in microbiota of said infant as compared to vaginally delivered full-term infants, and/or (ii) inhibits growth and/or activity of bacteria which are over-represented in microbiota of said infant as compared to vaginally delivered full-term infants.

38. A method for restoring normal microbiota in a pre-term infant, said method comprising administering to said infant at the time of birth and/or within the first 4 months of life an effective amount of a probiotic composition, wherein said probiotic composition (i) stimulates growth and/or activity of bacteria which are under-represented in microbiota of said infant as compared to vaginally delivered full-term infants, and/or (ii) inhibits growth and/or activity of bacteria which are over-represented in microbiota of said infant as compared to vaginally delivered full-term infants.

39. A method for treating a disease in a subject associated with the subject's delivery by Cesarean section or with the subject's pre-term birth, said method comprising administering to said subject at the time of birth and/or within the first 4 months of life a therapeutically effective amount of a probiotic composition, wherein said probiotic composition (i) stimulates growth and/or activity of bacteria which are under-represented in microbiota of said infant as compared to vaginally delivered full-term infants, and/or (ii) inhibits growth and/or activity of bacteria which are over-represented in microbiota of said infant as compared to vaginally delivered full-term infants.

40. The method of item 39, wherein said disease is an inflammatory or an autoimmune disorder.

41. The method of item 39, wherein said disease is selected from the group consisting of autoimmune diseases, allergic diseases, infectious diseases, and rejection in organ transplantations.

42. The method of item 39, wherein said disease is selected from the group consisting of asthma, allergy, celiac disease, type 1 diabetes, obesity, necrotizing enterocolitis, inflammatory bowel disease (IBD), ulcerative colitis, Crohn's disease, sprue, autoimmune arthritis, rheumatoid arthritis, multiple sclerosis, graft vs. host disease following bone marrow transplantation, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, and atherosclerosis.

43. The method of any one of items 37-42, wherein said probiotic composition comprises one or more bacterial strains from one or more taxa selected from the group consisting of *Lactobacillus, Bacteriodales, Bacteroides, Parabacteroides, Bacteroidacea, Porphyromonadaceae, Coriobacteriales, Bifidobacterium, Clostridiaceae, Stenotrophomonas*, and *Gemella*.

44. The method of item 43, wherein *Bacteriodales* is S24-7.

45. The method of any one of items 37-42, wherein said probiotic composition comprises one or more bacterial strains from one or more taxa recited in Table 1A.

46. The method of any one of items 37-42, wherein said probiotic composition comprises one or more bacterial strains recited in Table 1B.

47. The method of any one of items 37-42, wherein said probiotic composition comprises one or more bacterial strains from the family Neisseriaceae.

48. The method of any one of items 37-47, wherein said probiotic composition comprises one or more bacterial strains which can be found in a healthy vaginal microbiota from a pregnant woman in the third trimester of pregnancy before or at the time of giving birth.

49. The method of item 48, wherein the woman has not been administered antibiotic compounds within at least one month prior to isolation of bacteria, has body mass index (BMI) between 18.5 and 24.9, does not have Group B *Streptococcus* (GBS), human immunodeficiency virus (HIV), *Chlamydia*, and/or sexually transmitted diseases, has vaginal pH less than 4.5, and does not have irritable bowel disease, Crohn's disease, ulcerative colitis, irritable bowel syndrome, celiac disease, colorectal cancer and a family history of these diseases.

50. The method of any one of items 37-49, wherein said probiotic composition comprises live bacterial cells.

51. The method of any one of items 37-49, wherein said probiotic composition comprises one or more components selected from the group consisting of conditionally lethal bacterial cells, inactivated bacterial cells, killed bacterial cells, spores, recombinant carrier strains, cell extract, and bacterially-derived products.

52. The method of item 51, wherein the bacterially-derived product is a bacterial antigen or a bacterial metabolic product.

53. The method of any one of items 37-52, wherein said probiotic composition comprises (i) a carrier and/or excipient and/or (ii) one or more prebiotic agents which stimulate growth and/or activity of one or more bacteria present in the composition.

54. The method of any one of items 37-53, wherein said probiotic composition is reconstituted from a lyophilized preparation.

55. The method of any one of items 37-54, wherein the probiotic composition comprises a buffering agent to adjust pH to the natural vaginal pH at the time of labor or to a pH of 3.5 to 7.

56. The method of item 53, wherein the probiotic composition comprises an excipient or a carrier that optimizes the seeding of one or more bacterial strains contained in said probiotic composition.

57. The method of any one of items 37-56, wherein the probiotic composition is delivered to the mouth, nose, and/or skin of the infant and/or by placing it on the maternal breast and/or chest.

58. The method of any one of items 37-56, wherein the probiotic composition is administered to the infant by a route selected from the group consisting of oral, topical, rectal, mucosal, sublingual, nasal, and via naso/oro-gastric gavage.

59. The method of any one of items 37-58, wherein the probiotic composition is delivered to the infant in a form of a liquid, foam, cream, spray, powder, or gel.

60. The method of any one of items 37-59, wherein the probiotic composition is delivered using an absorbent material or device.

61. The method of item 60, wherein the absorbent material or device is selected from the group consisting of gauze, sponge, and tampon.

62. The method of any one of items 37-60, wherein the probiotic composition comprises a buffering agent.

63. The method of item 62, wherein the buffering agent comprises sodium bicarbonate, infant formula or sterilized human milk.

64. The method of any one of items 37-63, wherein the probiotic composition is administered conjointly with a prebiotic which stimulates growth and/or activity of one or more bacteria contained in the probiotic composition.

65. The method of item 64, wherein the prebiotic is selected from the group consisting of fructooligosaccharides (FOS), galactooligosaccharides (GO S), human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, arabinose, maltose, lactose, sucrose, cellobiose, amino acids, alcohols, resistant starch (RS), and any mixtures thereof.

66. The method of item 64, wherein the prebiotic is derived from microorganisms that show stimulation by human milk components.

67. The method of any one of items 64-66, wherein the probiotic and prebiotic are administered in one composition, or simultaneously as two separate compositions, or sequentially.

68. A method for diagnosing an abnormal microbiota development in an infant, comprising:
(a) determining a relative abundance of one or more bacterial taxa in a microbiota sample obtained from the infant, and
(b) comparing the relative abundance(s) determined in step (a) to (i) a predetermined standard value or (ii) to the abundance(s) of the same taxa in a control subject or (iii) to the median value of abundances of the same taxa in several control subjects, wherein the control subject is a vaginally delivered full-term healthy infant.

69. The method of item 68, wherein determining the relative abundance of the bacterial taxa comprises a method selected from the group consisting of quantitative polymerase chain reaction (qPCR), sequencing of bacterial 16S rRNA, shotgun metagenome sequencing, and metabolomics.

70. The method of item 68 or 69, wherein the bacterial taxa comprise one or more taxa selected from the group consisting of *Lactobacillus, Bacteriodales, Bacteroides, Parabacteroides, Bacteroidacea, Porphyromonadaceae, Coriobacteriales Bifidobacterium, Clostridiaceae, Stenotrophomonas,* and *Gemella.*

71. The method of item 70, wherein *Bacteriodales* is S24-7.

72. The method of item 68 or 69, wherein the bacterial taxa comprise one or more taxa present in a healthy vaginal microbiota from a pregnant woman in the third trimester of pregnancy before or at the time of giving birth.

73. The method of item 68 or 69, wherein the bacterial taxa comprise one or more taxa recited in Table 1A.

74. The method of item 68 or 69, wherein the bacterial taxa comprise one or more species recited in Table 1B.

75. The method of item 68 or 69, wherein the bacterial taxa comprise family Neisseriaceae.

76. The method of any one of items 1-75, 103, and 104, wherein the infant or subject is human.

77. A composition comprising (i) a vaginal microbiota inoculum and (ii) a carrier and/or excipient and/or one or more prebiotic agents which stimulate growth and/or activity of one or more bacteria present in the inoculum.

78. A probiotic composition comprising (a) one or more bacterial strains and (b) a carrier and/or excipient and/or one or more prebiotic agents which stimulate growth and/or activity of one or more of said bacterial strains, wherein said probiotic composition (i) stimulates growth and/or activity of bacteria which are under-represented in microbiota of an infant delivered by by Cesarean section or born prematurely as compared to vaginally delivered full-term healthy infants, and/or (ii) inhibits growth and/or activity of bacteria which are over-represented in microbiota of said infant as compared to vaginally delivered full-term healthy infants.

79. The composition of item 78, which comprises two or more different bacterial strains.

80. The composition of any one of items 77-79, which comprises bacteria from one or more taxa selected from the group consisting of *Lactobacillus, Bacteriodales, Bacteroides, Parabacteroides, Bacteroidacea, Porphyromonadaceae, Coriobacteriales, Bifidobacterium, Clostridiaceae, Stenotrophomonas,* and *Gemella.*

81. The composition of item 80, wherein *Bacteriodales* is S24-7.

82. The composition of any one of items 77-79, which comprises bacteria from one or more taxa recited in Table 1A.

83. The composition of any one of items 77-79, which comprises bacteria from one or more species recited in Table 1B.

84. The composition of any one of items 77-79, which comprises bacteria from family Neisseriaceae.

85. The composition of any one of items 77-84, wherein the composition comprises a buffering agent to adjust pH to the natural vaginal pH at the time of labor or to a pH of 3.5 to 7.

86. The composition of any one of items 77-85, wherein the composition comprises an excipient or a carrier that optimizes the seeding of one or more bacterial strains contained in the composition.

87. The composition of any one of items 77-86, wherein said composition is formulated for storage in a frozen form.

88. The composition of any one of items 77-87, wherein said composition is a lyophilized composition.

89. The composition of any one of items 77-88, wherein said composition comprises one or more bacterial strains which can be found in a healthy vaginal microbiota from a pregnant woman in the third trimester of pregnancy before or at the time of giving birth.

90. The composition of item 89, wherein the woman has not been administered antibiotic compounds at least one month prior to isolation of bacteria, has body mass index (BMI) between 18.5 and 24.9, does not have Group B *Streptococcus* (GBS), human immunodeficiency virus (HIV), *Chlamydia,* and/or sexually transmitted diseases, has vaginal pH less than 4.5, and does not have irritable bowel disease, Crohn's disease, ulcerative colitis, irritable bowel syndrome, celiac disease, colorectal cancer or a family history of these diseases.

91. The composition of any one of items 77-90, wherein said composition comprises live bacterial cells.

92. The composition of any one of items 77-90, wherein said composition comprises one or more components selected from the group consisting of conditionally lethal bacterial cells, inactivated bacterial cells, killed bacterial cells, spores, recombinant carrier strains, cell extract, and bacterially-derived products.

93. The composition of item 92, wherein the bacterially-derived product is a bacterial antigen or a bacterial metabolic product.

94. The composition of any one of items 77-93, wherein said composition is formulated for delivery to the mouth, nose, and/or skin of the infant and/or for placing it on the maternal breast and/or chest.

95. The composition of any one of items 77-93, wherein said composition is formulated for delivery by a route selected from the group consisting of oral, topical, rectal, mucosal, sublingual, nasal, and via naso/oro-gastric gavage.

96. The composition of any one of items 77-95, wherein the composition is in a form of a liquid, foam, cream, spray, powder, or gel.

97. The composition of any one of items 77-96, wherein the composition comprises a buffering agent.

98. The composition of item 97, wherein the buffering agent comprises sodium bicarbonate, infant formula or sterilized human milk.

99. The composition of any one of items 77-98, wherein the composition comprises a prebiotic which stimulates growth and/or activity of one or more bacteria contained in the composition.

100. The method of item 99, wherein the prebiotic is selected from the group consisting of fructooligosaccharides (FOS), galactooligosaccharides (GO S), human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, arabinose, maltose, lactose, sucrose, cellobiose, amino acids, alcohols, resistant starch (RS), and any mixtures thereof.

101. An absorbent material or device comprising the composition of any one of items 77-100.

102. The material or device of item 101, wherein the material or device is selected from the group consisting of gauze, sponge, and tampon.

103. A method for restoring normal microbiota in an infant delivered by Cesarean section, said method comprising administering to said infant at the time of birth and/or within the first 4 months of life an effective amount of the composition of any one of items 77-100.

104. A method for restoring normal microbiota in a pre-term infant, said method comprising administering to said infant at the time of birth and/or within the first 4 months of life an effective amount of the composition of any one of items 77-100.

105. A method for treating a disease in a subject associated with the subject's delivery by Cesarean section or with the subject's pre-term birth, said method comprising administering to said subject at the time of birth and/or within the first 4 months of life a therapeutically effective amount of the composition of any one of items 77-100.

106. The method of item 105, wherein the subject is human.

107. The method of any one of items 1-76, 103 and 104, wherein the infant is a newborn.

108. A device to collect maternal vaginal microbiota from the vaginal canal of a patient, comprising:
a housing forming a cavity;
an absorbent material disposed within the cavity; and
a deployment element disposed in the housing and movable along a length of the housing;
wherein the movement of the deployment element displaces the absorbent material out of the cavity and into the vaginal canal.

109. The device of item 108, wherein the absorbent material comprises a material that cannot be used as at least one of a menstrual pad, tampon, or urine pad.

110. The device of any one of items 108-109, wherein the housing and the deployment elements are sized to deliver the absorbent material within the lower ⅓ of the vaginal canal.

111. The device of any one of items 108-110, wherein the absorbent material lacks a retrieval interface.

112. The device of any one of items 108-110, wherein the absorbent material comprises a retrieval interface.

113. The device of item 112, wherein the retrieval interface is a tether, monofilament plastic line, or reattachable interface.

114. The device of any one of items 112-113, wherein the retrieval interface has a length and wherein at a full length the retrieval interface does not exit the vaginal canal.

115. The device of any one of items 112-113, wherein the retrieval interface has a length and wherein at a full length the retrieval interface does exit the vaginal canal.

116. The device of any one of items 108-115, further comprising a retrieval element.

117. The device of any one of item 116, wherein the retrieval element captures a deployed absorbent material and removes the delivered absorbent material from the vaginal canal.

118. The device of any one of items 108-117, wherein the deployment element acts as the retrieval element.

119. The device of any one of items 108-110 and 112-118, wherein the absorbent material comprises a retrieval interface and wherein the retrieval element captures the deployed absorbent material by interacting with the retrieval interface.

120. The device of any one of items 116-119, wherein the retrieval element is disposed within the housing and captures the deployed absorbent material and returns the absorbent material to the cavity for the removal of the absorbent material from the vaginal canal.

121. The device of any one of items 108-120, further comprising a second housing forming a second cavity;
wherein a retrieval element is disposed within the second housing and captures the deployed absorbent material and returns the absorbent material to the second cavity for the removal of the absorbent material from the vaginal canal.

122. The device of any one of items 108-121, wherein at least one of the housing, the cavity, the absorbent material and the deployment element are sterile.

123. The device of any one of items 108-122, wherein the housing further comprises a seal around at least one of the cavity and the absorbent material to maintain sterility.

124. The device of item 123, wherein the deployment element breaks the seal when deploying the absorbent material.

125. A method for collecting vaginal microbiota using the device of any one of items 108-124.

126. The method of item 125, wherein the vaginal microbiota is stored.

127. The method of item 125 or 126, wherein the vaginal microbiota is processed to isolate desired bacteria.

128. The method of item 126, wherein the vaginal microbiota is processed to isolate desired bacteria after being stored.

129. The method of item 126, wherein the vaginal microbiota is processed to isolate desired bacteria prior to being stored.

130. A method for collecting and administering vaginal microbiota using the device of any one of items 108-124.

131. The method of item 130, wherein the vaginal microbiota is stored.

132. The method of item 130 or 131, wherein the vaginal microbiota is processed to isolate desired bacteria.

133. The method of item 131, wherein the vaginal microbiota is processed to isolate desired bacteria after being stored.

134. The method of item 131, wherein the vaginal microbiota is processed to isolate desired bacteria prior to being stored.

135. The method of any one of items 130-134, wherein the vaginal microbiota is administered to an infant delivered by Cesarean section or born prematurely.

136. The method of any one of items 130-135, wherein the vaginal microbiota is administered at the time of birth and/or within the first 4 months of life.

137. The method of any one of items 125-136, wherein the vaginal microbiota is obtained from the subject's mother or from a donor during the third trimester of pregnancy before or at the time of giving birth.

138. The method of any one of items 130-137, wherein a therapeutically effective amount of vaginal microbiota is administered to treat a disease associated with an inflammatory or an autoimmune disorder.

139. The method of any one of items 130-138, wherein a therapeutically effective amount of vaginal microbiota is administered to restore normal microbiota colonization patterns in an infant.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A device to collect vaginal microbiota from the vaginal canal of a patient, comprising:
a housing forming a cavity;
an absorbent material disposed within the cavity;
a deployment element disposed in the housing and movable along a length of the housing,
wherein the movement of the deployment element removably displaces the absorbent material out of the cavity and into the vaginal canal; and
a retrieval element separate from the deployment element and configured to capture a deployed absorbent material and remove the deployed absorbent material from the vaginal canal,
wherein the deployed absorbent material is configured such that a proximal end of the deployed absorbent material does not extend beyond a distal end of the retrieval element during removal of the deployed absorbent material.

2. The device of claim 1, wherein the housing and the deployment element are sized to removably deliver the absorbent material within the lower ⅓ of the vaginal canal.

3. The device of claim 1, wherein the absorbent material lacks a retrieval interface.

4. The device of claim 1, wherein the absorbent material comprises a retrieval interface having a length, and at a full length the retrieval interface does not exit the vaginal canal.

5. The device of claim 1, further comprising a reattachable interface,
wherein the retrieval element is configured to capture the deployed absorbent material via the reattachable interface.

6. The device of claim 1, wherein the retrieval element is disposed within the housing and is configured to capture the deployed absorbent material and return the absorbent material to the cavity for the removal of the absorbent material from the vaginal canal.

7. The device of claim 1, further comprising a second housing forming a second cavity;
wherein the retrieval element is disposed within the second housing and is configured to capture the deployed absorbent material and return the absorbent material to the second cavity for the removal of the absorbent material from the vaginal canal.

8. The device of claim 1, wherein at least one of the housing, the cavity, the absorbent material and the deployment element are sterile.

9. The device of claim 8, wherein the housing further comprises a seal around at least one of the cavity and the absorbent material to maintain sterility.

10. The device of claim 9, wherein the deployment element is configured to break the seal when deploying the absorbent material.

11. A method comprising:
Collecting vaginal microbiota using the device of claim 1.

12. The device of claim 5, wherein:
the reattachable interface comprises a first component disposed on the proximal end of the deployed absorbent material and a second component disposed on the distal end of the retrieval element, and
the first and second components are configured to engage during removal of the deployed absorbent material.

13. The device of claim 12, wherein the first and second components comprise one or more magnets.

14. The device of claim 12, wherein the first and second components comprise one or more hooks and/or loops.

15. The device of claim 1, wherein the retrieval element is configured to remove the deployed absorbent material from the vaginal canal via suction.

* * * * *

SEQUENCE LISTING

```
<160> NUMBER OF SEQ ID NOS: 12

<210> SEQ ID NO 1
<211> LENGTH: 252
<212> TYPE: DNA
<213> ORGANISM: Eggerthella lenta

<400> SEQUENCE: 1
tacgtaggga gcgagcgtta tccggattca ttgggcgtaa agagcgcgta ggcggcctct      60
caagcgggat ctctaatccg agggctcaac ccccggccgg atcccgaact gggaggctcg     120
agttcggtag aggcaggcgg aattcccggt gtagcggtgg aatgcgcaga tatcgggaag     180
aacaccgatg gcgaaggcag cctgctgggc cgcaactgac gctgaggcgc gaaagctagg     240
ggagcgaaca gg                                                        252

<210> SEQ ID NO 2
<211> LENGTH: 254
<212> TYPE: DNA
<213> ORGANISM: Corynebacterium sp.

<400> SEQUENCE: 2
tacgtagggt gcgagcgttg tccggaatta ctgggcgtaa agagctcgta ggtggtttgt      60
cgcgtcgtct gtgaaattcc ggggcttaac tccgggcgtg caggcgatac gggcataact     120
tgagtactgt aggggagact ggaattcctg gtgtagcggt gaaatgcgca gatatcagga     180
ggaacaccgg tggcgaaggc gggtctctgg gcagtaactg acgctgagga gcgaaagcat     240
ggggagcgaa cagg                                                      254

<210> SEQ ID NO 3
<211> LENGTH: 253
<212> TYPE: DNA
<213> ORGANISM: Bacteroides sp.

<400> SEQUENCE: 3
tacggaggat ccgagcgtta tccggattta ttgggtttaa agggagcgta gatggatgtt      60
taagtcagtt gtgaaagttt gcggctcaac cgtaaaattg cagttgatac tggatgtctt     120
gagtgcagtt gaggcaggcg gaattcgtgg tgtagcggtg aaatgcttag atatcacgaa     180
gaactccgat tgcgaaggca gcctgctagg ctgcaactga cattgaggct cgaaagtgtg     240
ggtatcaaac agg                                                       253
```

<210> SEQ ID NO 4
<211> LENGTH: 253
<212> TYPE: DNA
<213> ORGANISM: Bifidobacterium sp.

<400> SEQUENCE: 4

```
tacgtagggc gcaagcgtta tccggattta ttgggcgtaa agggctcgta ggcggctcgt      60
cgcgtccggt gtgaaagtcc atcgcttaac ggtggatctg cgccgggtac gggcgggctt     120
gagtgcggta ggggagactg gaattcccgg tgtaacggtg aatgtgtag atatcgggaa      180 gaacaccaat ggcgaaggca ggtctctggg ccgttactga cgctgaggag cgaaagcgtg     240
gggagcgaac agg                                                        253
```

<210> SEQ ID NO 5
<211> LENGTH: 253
<212> TYPE: DNA
<213> ORGANISM: Parabacteroides distasonis

<400> SEQUENCE: 5

```
tacggaggat ccgagcgtta tccggattta ttgggtttaa agggtgcgta ggcggccttt      60
taagtcagcg gtgaaagtct gtggctcaac catagaattg ccgttgaaac tgggggggctt    120 gagtatgttt gaggcaggcg gaatgcgtgg tgtagcggtg aaatgcttag atatcacgca     180
gaaccccgat tgcgaaggca gcctgccaag ccatgactga cgctgatgca cgaaagcgtg     240
gggatcaaac agg                                                        253
```

<210> SEQ ID NO 6
<211> LENGTH: 253
<212> TYPE: DNA
<213> ORGANISM: Corynebacterium sp.

<400> SEQUENCE: 6

```
tacgtagggt gcgagcgttg tccggaatta ctgggcgtaa agagctcgta ggcggttttgt     60 cacgtcgtct gtgaaatcct agggcttaac cctggacgtg caggcgatac gggctgactt    120
gagtactaca ggggagactg gaatttctgg tgtagcggtg aatgcacag atatcaggaa      180 gaacaccgat ggcgaaggca ggtctctggg tagtaactga cgctgaggag cgaaagcatg     240
ggtagcgaac agg                                                        253
```

<210> SEQ ID NO 7
<211> LENGTH: 201
<212> TYPE: DNA
<213> ORGANISM: Unknown
<220> FEATURE:
<223> OTHER INFORMATION: Description of Unknown: Enterobacteriaceae
      polynucleotide

<400> SEQUENCE: 7

```
tacggagggt gcaagcgtta atcggaatta ctgggcgtaa agcgcacgca ggcggtttgt      60
taagtcagat gtgaaatccc cgggctcaac ctgggaactg catctgatac tggcaagctt    120
gagtctcgta gagggggta gaattccagg tgtagcggtg aaatgcgtag agatctggag      180
gaataccggt ggcgaaggcg g                                               201
```

<210> SEQ ID NO 8
<211> LENGTH: 252
<212> TYPE: DNA
<213> ORGANISM: Streptococcus sp.

```
<400> SEQUENCE: 8
tacgtaggtc ccgagcgtta tccggattta ttgggcgtaa agcgagcgca ggcggttaga      60
taagtctgaa gttaaaggct gtggcttaac catagtacgc tttggaaact gtttaacttg     120
agtgcagaag gggagagtgg aattccatgt gtagcggtga aatgcgtaga tatatggagg     180
aacaccggtg gcgaaagcgg ctctctggtc tgtaactgac gctgaggctc gaaagcgtgg     240
ggagcgaaca gg                                                         252

<210> SEQ ID NO 9
<211> LENGTH: 253
<212> TYPE: DNA
<213> ORGANISM: Corynebacterium sp.

<400> SEQUENCE: 9
tacgtagggt gcgagcgttg tccggaatta ctgggcgtaa agagctcgta ggcggtttgt      60
cacgtcgtct gtgaaatcct agggcttaac cctggacgtg caggcgatac gggctgactt     120
gagtactaca ggggagactg gaatttctgg tgtagcggtg aatgcacag atatcaggaa      180 gaacaccgat ggcgaaggca ggtctctggg tagtaactga cgctgaggag cgaaagcatg     240
gggagcgaac agg                                                        253

<210> SEQ ID NO 10
<211> LENGTH: 253
<212> TYPE: DNA
<213> ORGANISM: Corynebacterium sp.

<400> SEQUENCE: 10
tacgtagggt gcgagcgttg tccggaatta ctgggcgtaa agagctcgta ggcggtttgt      60
cacgtcgtct gtgaaatcct agggcttaac cctggacgtg caggcgatac gggctgactt     120
gagtactaca ggggagactg gaatttctgg tgtagcggtg aatgcacag atatcaggaa      180 gaacaccgat ggcgaaggca ggtctctggg tagtaactga cgctgaggag cgaaagcatg     240
ggtagcgaac agg                                                        253

<210> SEQ ID NO 11
<211> LENGTH: 252
<212> TYPE: DNA
<213> ORGANISM: Streptococcus sp.

<400> SEQUENCE: 11
tacgtaggtc ccgagcgttg tccggattta ttgggcgtaa agcgagcgca ggcggtttga      60
taagtctgaa gttaaaggct gtggctcaac catagttcgc tttggaaact gtcaacttg      120 agtgcagaag gggagagtgg aattccatgt gtagcggtga aatgcgtaga tatatggagg     180
aacaccggtg gcgaaagcgg ctctctggtc tgtaactgac gctgaggctc gaaagcgtgg     240
ggagcgaaca gg                                                         252

<210> SEQ ID NO 12
<211> LENGTH: 252
<212> TYPE: DNA
<213> ORGANISM: Peptoniphilus sp.

<400> SEQUENCE: 12
tacgtagggg gctagcgttg tccggaatca ctgggcgtaa agggttcgca ggcggaaatg      60
caagtcaggt gtaaaaggca gtagcttaac tactgtaagc atttgaaact gcatatcttg     120
```

-continued

```
agaagagtag aggtaagtgg aatttttagt gtagcggtga aatgcgtaga tattaaaaag    180
aataccggtg gcgaaggcga cttactgggc tcattctgac gctgaggaac gaaagcgtgg    240
gtagcaaaca gg                                                        252
```